(12) United States Patent
Goh et al.

(10) Patent No.: US 11,471,527 B2
(45) Date of Patent: Oct. 18, 2022

(54) VIRUS-LIKE PARTICLES INCLUDING HBS-L ANTIGEN PROTEIN FOR CAUSING IMMUNE RESPONSE AGAINST HBV

(71) Applicant: BEACLE INC., Kyoto (JP)

(72) Inventors: Yasumasa Goh, Kyoto (JP); Yasunori Oda, Kyoto (JP); Chinatsu Ohashi, Kyoto (JP); Kentaro Isotani, Kyoto (JP)

(73) Assignee: BEACLE INC., Kyoto (JP)

( * ) Notice: Subject to any disclaimer, the term of this patent is extended or adjusted under 35 U.S.C. 154(b) by 137 days.

(21) Appl. No.: 16/611,627

(22) PCT Filed: Jun. 5, 2018

(86) PCT No.: PCT/JP2018/021556
§ 371 (c)(1),
(2) Date: Nov. 7, 2019

(87) PCT Pub. No.: WO2018/225731
PCT Pub. Date: Dec. 13, 2018

(65) Prior Publication Data
US 2020/0164062 A1     May 28, 2020

(30) Foreign Application Priority Data

Jun. 5, 2017  (JP) .............................. JP2017-111176

(51) Int. Cl.
*A61K 39/29*     (2006.01)
*C12N 7/00*      (2006.01)
*A61K 39/00*     (2006.01)

(52) U.S. Cl.
CPC .............. *A61K 39/292* (2013.01); *C12N 7/00* (2013.01); *A61K 2039/575* (2013.01); *C12N 2730/10122* (2013.01); *C12N 2730/10123* (2013.01); *C12N 2730/10134* (2013.01)

(58) Field of Classification Search
None
See application file for complete search history.

(56) References Cited

U.S. PATENT DOCUMENTS

| | | |
|---|---|---|
| 2003/0092069 A1 | 5/2003 | Kuroda et al. |
| 2010/0292445 A1 | 11/2010 | Kuroda et al. |

FOREIGN PATENT DOCUMENTS

| | | |
|---|---|---|
| EP | 2 672 991 | 12/2013 |
| JP | 4085231 | 5/2008 |
| JP | 2010-516807 | 5/2010 |
| JP | 4936272 | 5/2012 |
| JP | 2015-530410 | 10/2015 |
| WO | 2008/093976 | 8/2008 |
| WO | 2014/047286 | 3/2014 |

OTHER PUBLICATIONS

International Search Report dated Aug. 7, 2018 in International (PCT) Application No. PCT/JP2018/021556.
Hellström et al., "PreS1 epitope recognition in newborns after vaccination with the third-generation Sci-B-Vac™ vaccine and their relation to the antibody response to hepatitis B surface antigen", Virology Journal, 2009, vol. 6, No. 7, pp. 1-6.
Yamada et al., "Physicochemical and immunological characterization of hepatitis B virus envelope particles exclusively consisting of the entire L (pre-S 1 + pre-S2 + S) protein", Vaccine, 2001, vol. 19, pp. 3154-3163.
Han et al., "Expression, purification and characterization of the Hepatitis B virus entire envelope large protein in *Pichia pastoris*", Protein Expression and Purification, 2006, vol. 49, pp. 168-175.
Yan et al., "Sodium taurocholate cotransporting polypeptide is a functional receptor for human hepatitis B and D virus", eLife, 2012, vol. 13, No. 1, pp. 1-28.
Iwamoto et al., "Evaluation and identification of hepatitis B virus entry inhibitors using HepG2 cells overexpressing a membrane transporter NTCP", Biochemical and Biophysical Research Communications, 2014, vol. 443, pp. 808-813.
Shouval et al., "Enhanced immune response to hepatitis B vaccination through immunization with a Pre-S1/Pre-S2/S Vaccine", Med Microbiol Immunol, 2015, vol. 204, pp. 57-68.
Soulie et al., "Immunogenicity and safety in newborns of a new recombinant hepatitis B vaccine containing the S and pre-S2 antigens", Vaccine, 1991, vol. 9, pp. 545-548.
Suzuki et al., "Safety and efficacy of a recombinant yeast-derived pre-S2 + S-containing hepatitis B vaccine (TGP-943): phase 1, 2 and 3 clinical testing", Vaccine, 1994, vol. 12, No. 12, pp. 1090-1096.
Sunbul et al., "Hepatitis B virus genotypes: Global disuibution and clinical importance", World J Gastroenterol, 2014, vol. 20, No. 18, pp. 5427-5434.
Usuda et al., "Serological detection of hepatitis B virus genotypes by ELISA with monoclonal antibodies to type-specific epitopes in the preS2-region product", Journal of Virological Methods, 1999, vol. 80, No. 1, pp. 97-112.
Zhang et al., "Neutralization epitope responsible for the hepatitis B virus subtype-specific protection in chimpanzees", Proc. Natl. Acad. Sci, 2006, vol. 103, No. 24, pp. 9214-9219.
Hong et al., "In vivo neutralization of hepatitis B virus infection by an anti-preS1 humanized antibody in chimpanzees", Virology, 2004, vol. 318, pp. 134-141.
Akbar et al., "Immune therapy for hepatitis B", Annals of Translational Medicine, 2016, vol. 4, No. 18, pp. 1-10.
Li et al., "Hepatitis B surface antigen (HBsAg) and core antigen (HBcAg) combine CpG oligodeoxynucletides as a novel therapeutic vaccine for chronic hepatitis B infection", Vaccine, 2015, vol. 33, pp. 4247-4254.

(Continued)

*Primary Examiner* — Nicole Kinsey White
(74) *Attorney, Agent, or Firm* — Wenderoth, Lind & Ponack, L.L.P.

(57) ABSTRACT

The present invention provides a virus-like particle comprising several or more types of HBs-L antigen proteins or a virus-like particle composition comprising a combination of the virus-like particles, for the purpose of provision of an antigen that triggers an immune reaction against HBV of various genotypes.

12 Claims, 32 Drawing Sheets
Specification includes a Sequence Listing.

(56) References Cited

OTHER PUBLICATIONS

Kosinska et al., "Therapeutic vaccination and immunomodulation in the treatment of chronic hepatitis B: preclinical studies in the woodchuck", Med Microbiol Immunol, 2015, vol. 204, pp. 103-114.

Al-Mahtab et al., "Therapeutic potential of a combined hepatitis B virus surface and core antigen vaccine inpatients with chronic hepatitis B", Hepatol Int, 2013, vol. 7, pp. 981-989.

Tong et al., "Natural killer cell activation contributes to hepatitis B viral control in a mouse model", Scientific Reports, 2017, vol. 7, No. 314, pp. 1-11.

Yum et al., "Use of Pre-S Protein-Containing Hepatitis B Virus Surface Antigens and a Powerful Adjuvant to Develop an Immune Therapy for Chronic Hepatitis B Virus Infection", Clinical and Vaccine Immunology, 2012, vol. 19, No. 2, pp. 120-127.

Diminsky et al., "Physical, chemical and immunological stability of CHO-derived hepatitis B surface antigen (HBsAg) particles", Vaccine, 2000, vol. 18, pp. 3-17.

Kuroda et al., "Hepatitis B Virus Envelope L Protein Particles, Synthesis and Assembly In *Saccharomyces cerevisiae*, Purification and Characterization", The Journal of Biological Chemistry, 1992, vol. 267, No. 3, pp. 1953-1961.

Okamoto et al., "Typing Hepatitis B Virus by Homology in Nucleotide Sequence: Comparison of Surface Antigen Subtypes", J. gen. Virol., 1988, vol. 69, pp. 2575-2583.

Magnius et al., "Subtypes, Genotypes and Molecular Epidemiology of the Hepatitis B Virus as Reflected by Sequence Variability of the S-Gene", Intervirology, 1995, vol. 38, pp. 24-34.

Usuda et al., "Serological detection of hepatitis B virus genotypes by ELISA with monoclonal antibodies to type-specific epitopes in the preS2-region product", Journal of Virological Methods, 1999, vol. 80, pp. 97-112.

Stuyver et al., "A new genotype of hepatitis B virus: complete genome and phylogenetic relatedness", Journal of General Virology, 2000, vol. 81, pp. 67-74.

Stramer et al., Nucleic Acid Testing to Detect HBV Infection in Blood Donors, The New England Journal of Medicine, 2011, vol. 364, No. 3, pp. 236-247.

Notice of Reasons for Refusal dated Mar. 12, 2019 in corresponding Japanese Patent Application No. 2019-500612, with English translation.

Extended European Search Report dated Mar. 3, 2021 in corresponding European Patent Application No. 18813550.3.

A silver stain

B western blot

A silver stain

B western blot

M: marker
Lc: Lc antigen

A  silver stain

B  western blot

M: marker
Lc: L antigen (Genotype C)
Ld: L antigen (Genotype D)
Lh1: L antigen (Genotype C+D)

SEQUENCE LISTING

<160> NUMBER OF SEQ ID NOS: 66

<210> SEQ ID NO 1
<211> LENGTH: 400
<212> TYPE: PRT
<213> ORGANISM: Hepatitis B virus

<400> SEQUENCE: 1

```
Met Gly Gly Trp Ser Ser Lys Pro His Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Val
        35                  40                  45

Lys Asp His Trp Pro Gln Ala Asn Gln Val Gly Val Gly Ala Phe Gly
    50                  55                  60

Pro Gly Phe Thr Pro Pro His Gly Gly Val Leu Gly Trp Ser Pro Gln
65                  70                  75                  80

Ala Gln Gly Ile Leu Ala Thr Val Pro Ala Val Pro Pro Pro Ala Ser
            85                  90                  95

Thr Asn Arg Gln Ser Gly Arg Gln Pro Thr Pro Ile Ser Pro Pro Leu
            100                 105                 110

Arg Asp Ser His Pro Gln Ala Val Arg Trp Asn Ser Thr Thr Phe His
        115                 120                 125

Gln Thr Leu Gln Asp Pro Arg Val Arg Gly Leu Tyr Leu Pro Ala Gly
    130                 135                 140

Gly Ser Ser Ser Gly Thr Leu Asn Pro Val Pro Asn Ile Ala Ser His
145                 150                 155                 160

Ile Ser Ser Ile Ser Ser Arg Thr Gly Asp Pro Ala Pro Asn Met Glu
                165                 170                 175

Asn Ile Thr Ser Gly Phe Leu Gly Pro Leu Leu Ala Leu Gln Ala Gly
            180                 185                 190

Phe Phe Ser Leu Thr Arg Ile Leu Thr Ile Pro Gln Ser Leu Asp Ser
        195                 200                 205

Trp Trp Thr Ser Leu Asn Phe Leu Gly Gly Ser Pro Val Cys Leu Gly
    210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255
```

```
Phe Leu Phe Ile Leu Leu Leu Cys Leu Ile Phe Leu Leu Val Leu Leu
                260                 265                 270

Asp Tyr Gln Gly Met Leu Pro Val Cys Pro Leu Ile Pro Gly Ser Thr
            275                 280                 285

Thr Thr Ser Thr Gly Pro Cys Lys Thr Cys Thr Thr Pro Ala Gln Gly
        290                 295                 300

Asn Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Val Pro
            340                 345                 350

Phe Val Gln Trp Phe Ala Gly Leu Ser Pro Thr Val Trp Leu Ser Ala
        355                 360                 365

Ile Trp Met Met Trp Tyr Trp Gly Pro Ser Leu Tyr Asn Ile Leu Ser
    370                 375                 380

Pro Phe Ile Pro Leu Leu Pro Ile Phe Leu Cys Leu Trp Val Tyr Ile
385                 390                 395                 400

<210> SEQ ID NO 2
<211> LENGTH: 400
<212> TYPE: PRT
<213> ORGANISM: Hepatitis B virus

<400> SEQUENCE: 2

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Val
        35                  40                  45

Lys Asp His Trp Pro Gln Ala Asn Gln Val Gly Val Gly Ala Phe Gly
    50                  55                  60

Pro Gly Phe Thr Pro Pro His Gly Gly Val Leu Gly Trp Ser Pro Gln
65                  70                  75                  80

Ala Gln Gly Ile Leu Ala Thr Val Pro Ala Val Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Val Lys Trp Asn Ser Thr Thr Phe His
        115                 120                 125

Gln Ala Leu Gln Asp Pro Arg Val Arg Ser Leu Tyr Leu Pro Ala Gly
    130                 135                 140

Gly Ser Ser Ser Gly Thr Leu Asn Pro Val Pro Asn Ile Ala Ser His
145                 150                 155                 160

Ile Ser Ser Ile Ser Ser Arg Thr Gly Asp Pro Ala Pro Asn Met Glu
                165                 170                 175

Asn Ile Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ser Pro Val Cys Leu Gly
    210                 215                 220

Gln Asn Ser Gln Ser Pro Thr Ser Asn His Ser Pro Thr Ser Cys Pro
225                 230                 235                 240
```

```
Pro Ile Cys Pro Gly Tyr Arg Trp Met Cys Leu Arg Arg Phe Ile Ile
            245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Thr
            275                 280                 285

Thr Thr Ser Thr Gly Pro Cys Lys Thr Cys Thr Thr Pro Ala Gln Gly
            290                 295                 300

Asn Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
            325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Ala
            355                 360                 365

Ile Trp Met Met Trp Tyr Trp Gly Arg Ser Leu Tyr Asn Ile Leu Ser
            370                 375                 380

Pro Phe Ile Pro Leu Leu Pro Ile Phe Phe Cys Leu Trp Val Tyr Ile
385                 390                 395                 400

<210> SEQ ID NO 3
<211> LENGTH: 400
<212> TYPE: PRT
<213> ORGANISM: Hepatitis B virus

<400> SEQUENCE: 3

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Ile
            35                  40                  45

Lys Asp His Trp Pro Ala Ala Asn Gln Val Gly Ala Gly Ala Phe Gly
50                  55                  60

Pro Gly Leu Thr Pro Pro His Gly Gly Ile Leu Gly Trp Ser Pro Gln
65                  70                  75                  80

Ala Gln Gly Ile Leu Thr Thr Val Ser Thr Ile Pro Pro Pro Ala Ser
            85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Ala Phe His
            115                 120                 125

Gln Ala Leu Gln Asp Pro Arg Val Arg Gly Leu Tyr Phe Pro Ala Gly
            130                 135                 140

Gly Ser Ser Ser Gly Thr Val Asn Pro Ala Pro Asn Ile Ala Ser His
145                 150                 155                 160

Ile Ser Ser Ile Ser Ala Arg Thr Gly Asp Pro Val Thr Asn Met Glu
            165                 170                 175

Asn Ile Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
            195                 200                 205

Trp Trp Thr Ser Leu Asn Phe Leu Gly Gly Ser Pro Val Cys Leu Gly
```

```
                210                 215                 220
Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Thr
            275                 280                 285

Thr Thr Ser Thr Gly Pro Cys Lys Thr Cys Thr Thr Pro Ala Gln Gly
        290                 295                 300

Asn Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Ala
            355                 360                 365

Ile Trp Met Met Trp Tyr Trp Gly Pro Ser Leu Tyr Ser Ile Val Ser
370                 375                 380

Pro Phe Ile Pro Leu Leu Pro Ile Phe Phe Cys Leu Trp Val Tyr Ile
385                 390                 395                 400

<210> SEQ ID NO 4
<211> LENGTH: 400
<212> TYPE: PRT
<213> ORGANISM: Hepatitis B virus

<400> SEQUENCE: 4

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Ile
        35                  40                  45

Lys Asp His Trp Pro Ala Ala Asn Gln Val Gly Val Gly Ala Phe Gly
50                  55                  60

Pro Gly Leu Thr Pro Pro His Gly Gly Ile Leu Gly Trp Ser Pro Gln
65                  70                  75                  80

Ala Gln Gly Ile Leu Thr Thr Val Ser Thr Ile Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Ala Phe His
        115                 120                 125

Gln Ala Leu Gln Asp Pro Arg Val Arg Gly Leu Tyr Phe Pro Ala Gly
130                 135                 140

Gly Ser Ser Ser Gly Thr Val Asn Pro Ala Pro Asn Ile Ala Ser His
145                 150                 155                 160

Ile Ser Ser Ile Ser Ala Arg Thr Gly Asp Pro Val Thr Asn Met Glu
                165                 170                 175

Asn Ile Thr Ser Gly Phe Leu Gly Pro Leu Leu Val Leu Gln Ala Gly
            180                 185                 190
```

```
Phe Phe Leu Leu Thr Arg Ile Leu Thr Ile Pro Gln Ser Leu Asp Ser
            195                 200                 205

Trp Trp Thr Ser Leu Asn Phe Leu Gly Gly Ser Pro Val Cys Leu Gly
        210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Thr
        275                 280                 285

Thr Thr Ser Thr Gly Pro Cys Lys Thr Cys Thr Thr Leu Val Gln Gly
    290                 295                 300

Asn Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Ala
        355                 360                 365

Ile Trp Met Thr Trp Tyr Trp Gly Pro Ser Leu Tyr Ser Ile Val Ser
    370                 375                 380

Pro Phe Ile Pro Leu Leu Pro Ile Phe Phe Cys Leu Trp Val Tyr Ile
385                 390                 395                 400

<210> SEQ ID NO 5
<211> LENGTH: 400
<212> TYPE: PRT
<213> ORGANISM: Hepatitis B virus

<400> SEQUENCE: 5

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Pro Asp Trp Asp Phe Asn Pro Ile
        35                  40                  45

Lys Asp His Trp Pro Ala Ala Asn Gln Val Gly Val Gly Ala Phe Gly
50                  55                  60

Pro Gly Phe Thr Pro Pro His Gly Gly Ile Leu Gly Trp Ser Pro Gln
65                  70                  75                  80

Ala Gln Gly Ile Leu Thr Thr Val Ser Thr Ile Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Ala Phe His
        115                 120                 125

Gln Thr Leu Gln Asp Pro Arg Val Arg Gly Leu Tyr Leu Pro Ala Gly
    130                 135                 140

Gly Ser Ser Ser Gly Thr Val Asn Pro Ala Pro Asn Ile Ala Ser His
145                 150                 155                 160

Ile Ser Ser Ile Ser Ala Arg Thr Gly Asp Pro Val Thr Asn Met Glu
                165                 170                 175
```

```
Asn Ile Thr Ser Gly Phe Leu Gly Pro Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ser Pro Val Cys Leu Gly
210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Thr
        275                 280                 285

Thr Thr Ser Thr Gly Pro Cys Lys Thr Cys Thr Thr Pro Ala Gln Gly
    290                 295                 300

Asn Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Phe Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Ala
        355                 360                 365

Ile Trp Met Met Trp Tyr Trp Gly Pro Ser Leu Tyr Ser Ile Val Arg
    370                 375                 380

Pro Phe Ile Pro Leu Leu Pro Ile Phe Phe Cys Leu Trp Val Tyr Ile
385                 390                 395                 400

<210> SEQ ID NO 6
<211> LENGTH: 400
<212> TYPE: PRT
<213> ORGANISM: Hepatitis B virus

<400> SEQUENCE: 6

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Val Phe Gly Ala Asn Ser Asn Asn Pro Asp Trp Asp Phe Asn Pro Ile
        35                  40                  45

Lys Asp His Trp Pro Ala Ala Asn Gln Val Gly Val Gly Ala Phe Gly
    50                  55                  60

Pro Gly Phe Thr Pro Pro His Gly Gly Val Leu Gly Trp Ser Pro Gln
65                  70                  75                  80

Ala Gln Gly Met Leu Thr Pro Val Ser Thr Ile Pro Pro Pro Ala Ser
                85                  90                  95

Ala Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Ala Phe His
        115                 120                 125

Gln Ala Leu Gln Asp Pro Arg Val Arg Gly Leu Tyr Phe Pro Ala Gly
    130                 135                 140

Gly Ser Ser Ser Gly Thr Val Asn Pro Ala Pro Asn Ile Ala Ser His
```

```
            145                 150                 155                 160
        Ile Ser Ser Ile Ser Ala Arg Thr Gly Asp Pro Val Thr Asn Met Glu
                        165                 170                 175

Asn Ile Thr Ser Gly Phe Leu Gly Pro Leu Pro Val Leu Gln Ala Gly
                    180                 185                 190

Phe Phe Leu Leu Thr Arg Ile Leu Thr Ile Pro Gln Ser Leu Asp Ser
                    195                 200                 205

Trp Trp Thr Ser Leu Asn Phe Leu Gly Gly Ser Pro Val Cys Leu Gly
                210                 215                 220

Gln Asn Ser Arg Ser Pro Thr Ser Asn His Ser Pro Thr Ser Cys Pro
        225                 230                 235                 240

Pro Ile Cys Pro Gly Tyr Arg Trp Met Cys Leu Arg Arg Phe Ile Ile
                        245                 250                 255

Phe Leu Phe Ile Leu Leu Leu Cys Leu Ile Phe Leu Leu Val Leu Leu
                    260                 265                 270

Asp Tyr Gln Gly Met Leu Pro Val Cys Pro Leu Ile Leu Gly Ser Thr
                    275                 280                 285

Thr Thr Ser Thr Gly Pro Cys Lys Thr Cys Thr Thr Pro Ala Gln Gly
                290                 295                 300

Asn Ser Met Phe Pro Ser Cys Cys Cys Thr Lys Pro Thr Asp Gly Asn
        305                 310                 315                 320

Cys Thr Cys Ile Pro Ile Pro Ser Ser Trp Ala Phe Ala Lys Tyr Leu
                        325                 330                 335

Trp Glu Trp Ala Ser Val Arg Phe Ser Trp Leu Ser Leu Leu Val Pro
                    340                 345                 350

Phe Val Gln Trp Phe Val Gly Leu Ser Pro Thr Val Trp Leu Ser Ala
                    355                 360                 365

Ile Trp Met Met Trp Tyr Trp Gly Pro Ser Leu Tyr Ser Ile Val Ser
                370                 375                 380

Ser Phe Ile Pro Leu Leu Pro Ile Phe Phe Cys Leu Trp Val Tyr Ile
        385                 390                 395                 400

<210> SEQ ID NO 7
<211> LENGTH: 400
<212> TYPE: PRT
<213> ORGANISM: Hepatitis B virus

<400> SEQUENCE: 7

Met Gly Gly Trp Ser Ser Lys Pro Arg Lys Gly Met Gly Thr Asn Leu
        1               5                   10                  15

Ser Val Pro Asn Pro Leu Gly Phe Phe Pro Asp His Gln Leu Asp Pro
                        20                  25                  30

Ala Phe Gly Ala Asn Ser Asn Asn Pro Asp Trp Asp Phe Asn Pro Ile
                    35                  40                  45

Lys Asp His Trp Pro Gln Ala Asn Gln Val Gly Val Gly Ala Phe Gly
            50                  55                  60

Pro Gly Phe Thr Pro Pro His Gly Gly Val Leu Gly Trp Ser Pro Gln
        65                  70                  75                  80

Ala Gln Gly Ile Leu Ala Thr Val Pro Ala Met Pro Pro Pro Ala Ser
                        85                  90                  95

Thr Asn Arg Gln Ser Gly Arg Gln Pro Thr Pro Ile Ser Pro Pro Leu
                    100                 105                 110

Arg Asp Ser His Pro Gln Ala Met Gln Trp Asn Ser Thr Ala Phe His
                    115                 120                 125
```

```
Gln Ala Leu Gln Asp Pro Arg Val Arg Gly Leu Tyr Phe Pro Ala Gly
130                 135                 140

Gly Ser Ser Gly Thr Leu Asn Pro Val Pro Thr Ile Ala Ser His
145                 150                 155                 160

Ile Ser Ser Ile Ser Ser Arg Ile Gly Asp Pro Ala Pro Asn Met Glu
                165                 170                 175

Asn Ile Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
                195                 200                 205

Trp Trp Thr Ser Leu Asn Phe Leu Gly Gly Ala Pro Val Cys Leu Gly
210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
                260                 265                 270

Asp Tyr Gln Gly Met Leu Pro Val Cys Pro Leu Ile Pro Gly Ser Thr
                275                 280                 285

Thr Thr Ser Thr Gly Pro Cys Lys Thr Cys Thr Thr Pro Ala Gln Gly
290                 295                 300

Asn Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Val Pro
                340                 345                 350

Phe Val Gln Trp Phe Val Gly Leu Ser Pro Thr Val Trp Leu Ser Ala
                355                 360                 365

Ile Trp Met Met Trp Tyr Trp Gly Pro Ser Leu Tyr Asn Ile Leu Ser
                370                 375                 380

Pro Phe Ile Pro Leu Leu Pro Ile Phe Phe Cys Leu Trp Val Tyr Ile
385                 390                 395                 400

<210> SEQ ID NO 8
<211> LENGTH: 400
<212> TYPE: PRT
<213> ORGANISM: Hepatitis B virus

<400> SEQUENCE: 8

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Gly Ala Asn Ser Asn Asn Pro Asp Trp Asp Phe Asn Pro Ile
            35                  40                  45

Lys Asp His Trp Pro Gln Ala Asn Gln Val Gly Val Gly Ala Phe Gly
        50                  55                  60

Pro Gly Phe Thr Pro Pro His Gly Gly Val Leu Gly Trp Ser Pro Gln
65                  70                  75                  80

Ala Gln Gly Ile Leu Ala Thr Val Pro Ala Val Pro Pro Pro Ala Ser
                85                  90                  95

Thr Asn Arg Gln Ser Gly Arg Gln Pro Thr Pro Ile Ser Pro Pro Leu
                100                 105                 110
```

Arg Asp Ser His Pro Gln Ala Met Gln Trp Asn Ser Thr Ala Phe His
            115                 120                 125

Gln Ala Leu Gln Asp Pro Arg Val Arg Gly Leu Tyr Phe Pro Ala Gly
        130                 135                 140

Gly Ser Ser Gly Thr Leu Asn Pro Val Pro Asn Ile Ala Ser His
145                 150                 155                 160

Ile Ser Ser Ile Ser Ser Arg Thr Gly Asp Pro Ala Pro Asn Met Glu
                    165                 170                 175

Asn Ile Thr Ser Gly Phe Leu Gly Pro Leu Leu Val Leu Gln Ala Gly
                180                 185                 190

Phe Phe Leu Leu Thr Arg Ile Leu Thr Ile Pro Gln Ser Leu Asp Ser
            195                 200                 205

Trp Trp Thr Ser Leu Asn Phe Leu Gly Gly Ser Pro Val Cys Leu Gly
        210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                    245                 250                 255

Phe Leu Phe Ile Leu Leu Leu Cys Leu Ile Phe Leu Leu Val Leu Leu
                260                 265                 270

Asp Tyr Gln Gly Met Leu Pro Val Cys Pro Leu Ile Pro Gly Ser Thr
            275                 280                 285

Thr Thr Ser Thr Gly Pro Cys Lys Thr Cys Thr Thr Pro Ala Gln Gly
        290                 295                 300

Asn Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                    325                 330                 335

Trp Glu Trp Ala Ser Val Arg Phe Ser Trp Leu Ser Leu Leu Val Pro
                340                 345                 350

Phe Val Gln Trp Phe Val Gly Leu Ser Pro Thr Val Trp Leu Ser Ala
            355                 360                 365

Ile Trp Met Met Trp Tyr Trp Gly Pro Ser Leu Tyr Asn Ile Leu Ser
        370                 375                 380

Pro Phe Ile Pro Leu Leu Pro Ile Phe Phe Cys Leu Trp Val Tyr Ile
385                 390                 395                 400

<210> SEQ ID NO 9
<211> LENGTH: 400
<212> TYPE: PRT
<213> ORGANISM: Hepatitis B virus

<400> SEQUENCE: 9

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Ile
        35                  40                  45

Lys Asp His Trp Pro Ala Ala Asn Gln Val Gly Val Gly Ala Phe Gly
    50                  55                  60

Pro Gly Leu Thr Pro Pro His Gly Gly Ile Leu Gly Trp Ser Pro Gln
65                  70                  75                  80

Ala Gln Gly Ile Leu Thr Thr Val Ser Thr Ile Pro Pro Pro Ala Ser

```
                85                  90                  95
Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Ala Phe His
            115                 120                 125

Gln Ala Leu Gln Asp Pro Arg Val Arg Gly Leu Tyr Phe Pro Ala Gly
            130                 135                 140

Gly Ser Ser Ser Gly Thr Val Asn Pro Ala Pro Asn Ile Ala Ser His
145                 150                 155                 160

Ile Ser Ser Ile Ser Ala Arg Thr Gly Asp Pro Val Thr Asn Met Glu
                165                 170                 175

Asn Ile Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
            195                 200                 205

Trp Trp Thr Ser Leu Asn Phe Leu Gly Gly Ser Pro Val Cys Leu Gly
            210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Thr
            275                 280                 285

Thr Thr Ser Thr Gly Pro Cys Lys Thr Cys Thr Thr Pro Ala Gln Gly
            290                 295                 300

Asn Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Ala
            355                 360                 365

Ile Trp Met Met Trp Tyr Trp Gly Pro Ser Leu Tyr Ser Ile Val Ser
            370                 375                 380

Pro Phe Ile Pro Leu Leu Pro Ile Phe Phe Cys Leu Trp Val Tyr Ile
385                 390                 395                 400

<210> SEQ ID NO 10
<211> LENGTH: 400
<212> TYPE: PRT
<213> ORGANISM: Hepatitis B virus

<400> SEQUENCE: 10

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Lys Ala Asn Ser Glu Asn Pro Asp Trp Asp Leu Asn Pro His
            35                  40                  45

Lys Asp Asn Trp Pro Asp Ala Asn Lys Val Gly Val Gly Ala Phe Gly
        50                  55                  60
```

```
Pro Gly Phe Thr Pro Pro His Gly Gly Leu Leu Gly Trp Ser Pro Gln
65                  70                  75                  80

Ala Gln Gly Leu Leu Thr Thr Val Pro Ala Ala Pro Pro Ala Ser
            85                  90                  95

Thr Asn Arg Gln Ser Gly Arg Gln Pro Thr Pro Phe Ser Pro Pro Leu
            100                 105                 110

Arg Asp Thr His Pro Gln Ala Met Gln Trp Asn Ser Thr Thr Phe Leu
            115                 120                 125

Gln Thr Leu Gln Asp Ser Arg Val Arg Ala Leu Tyr Leu Pro Ala Gly
    130                 135                 140

Gly Ser Ser Ser Gly Thr Val Ser Pro Ala Gln Asn Thr Val Ser Ala
145                 150                 155                 160

Ile Ser Ser Ile Ser Ser Lys Thr Gly Asp Pro Val Pro Asn Met Glu
                165                 170                 175

Asn Ile Ala Ser Gly Leu Leu Gly His Leu Val Leu Gln Ala Gly
            180                 185                 190

Phe Phe Ser Leu Thr Lys Ile Leu Thr Ile Pro Gln Ser Leu Asp Ser
    195                 200                 205

Trp Trp Thr Ser Leu Asn Phe Leu Gly Gly Thr Pro Ala Cys Pro Gly
210                 215                 220

Gln Asn Ser Gln Ser Gln Ile Ser Ser His Ser Pro Thr Cys Cys Pro
225                 230                 235                 240

Pro Ile Cys Pro Gly Tyr Arg Trp Met Cys Leu Arg Arg Phe Ile Ile
                245                 250                 255

Phe Leu Cys Ile Leu Leu Leu Cys Leu Ile Phe Leu Leu Val Leu Leu
            260                 265                 270

Asp Tyr Gln Gly Met Leu Pro Val Cys Pro Leu Thr Pro Gly Ser Thr
    275                 280                 285

Thr Thr Ser Thr Gly Pro Cys Lys Thr Cys Thr Thr Pro Ala Gln Gly
290                 295                 300

Thr Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Gly Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Val
    355                 360                 365

Ile Trp Met Met Trp Phe Trp Gly Pro Ser Leu Tyr Asn Ile Leu Arg
            370                 375                 380

Pro Phe Met Pro Leu Leu Pro Thr Phe Phe Cys Leu Trp Val Tyr Ile
385                 390                 395                 400

<210> SEQ ID NO 11
<211> LENGTH: 400
<212> TYPE: PRT
<213> ORGANISM: Hepatitis B virus

<400> SEQUENCE: 11

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Lys Ala Asn Ser Glu Asn Pro Asp Trp Asp Leu Asn Pro Asn
        35                  40                  45
```

Lys Asp Asn Trp Pro Asp Ala Asn Lys Val Gly Val Gly Ala Phe Gly
50                  55                  60

Pro Gly Phe Thr Pro Pro His Gly Gly Leu Leu Gly Trp Ser Pro Gln
65                  70                  75                  80

Ala Gln Gly Leu Leu Thr Thr Val Pro Ala Ala Pro Pro Pro Ala Ser
                85                  90                  95

Thr Asn Arg Gln Ser Gly Arg Gln Pro Thr Pro Leu Ser Pro Pro Leu
            100                 105                 110

Arg Asp Thr His Pro Gln Ala Met Gln Trp Asn Ser Thr Thr Phe His
        115                 120                 125

Gln Thr Leu Gln Asp Pro Gly Val Arg Ala Leu Tyr Phe Pro Ala Gly
130                 135                 140

Gly Ser Ser Ser Gly Thr Val Ser Pro Ala Gln Asn Thr Val Ser Ala
145                 150                 155                 160

Ile Ser Ser Ile Leu Ser Lys Thr Gly Asp Pro Val Pro Asn Met Glu
                165                 170                 175

Asn Ile Ala Ser Gly Leu Leu Gly Pro Leu Leu Val Leu Gln Ala Gly
            180                 185                 190

Phe Phe Leu Leu Thr Lys Ile Leu Thr Ile Pro Gln Ser Leu Asp Ser
        195                 200                 205

Trp Trp Thr Ser Leu Asn Phe Leu Gly Gly Thr Pro Val Cys Leu Gly
210                 215                 220

Gln Asn Ser Gln Ser Gln Ile Ser Ser His Ser Pro Thr Cys Cys Pro
225                 230                 235                 240

Pro Ile Cys Pro Gly Tyr Arg Trp Met Cys Leu Arg Arg Phe Ile Ile
                245                 250                 255

Phe Leu Cys Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Ser
        275                 280                 285

Thr Thr Ser Thr Gly Pro Cys Lys Thr Cys Thr Thr Pro Ala Gln Gly
290                 295                 300

Thr Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Val
        355                 360                 365

Ile Trp Met Ile Trp Phe Trp Gly Pro Ser Leu Tyr Asn Ile Leu Ser
370                 375                 380

Pro Phe Met Pro Leu Leu Pro Ile Phe Phe Cys Leu Trp Val Tyr Ile
385                 390                 395                 400

<210> SEQ ID NO 12
<211> LENGTH: 400
<212> TYPE: PRT
<213> ORGANISM: Hepatitis B virus

<400> SEQUENCE: 12

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro

```
            20                  25                  30
Ala Phe Lys Ala Asn Ser Glu Asn Pro Asp Trp Asp Leu Asn Pro His
            35                  40                  45

Lys Asp Asn Trp Pro Asp Ala His Lys Val Gly Val Gly Ala Phe Gly
        50                  55                  60

Pro Gly Phe Thr Pro Pro His Gly Gly Leu Leu Gly Trp Ser Pro Gln
65                  70                  75                  80

Ala Gln Gly Ile Leu Thr Ser Val Pro Ala Pro Pro Pro Ala Ser
                85                  90                  95

Thr Asn Arg Gln Ser Gly Arg Gln Pro Thr Pro Leu Ser Pro Pro Leu
                100                 105                 110

Arg Asp Thr His Pro Gln Ala Met Gln Trp Asn Ser Thr Thr Phe His
            115                 120                 125

Gln Thr Leu Gln Asp Pro Arg Val Arg Ala Leu Tyr Phe Pro Ala Gly
    130                 135                 140

Gly Ser Ser Ser Gly Thr Val Ser Pro Ala Gln Asn Thr Val Ser Ala
145                 150                 155                 160

Ile Ser Ser Ile Leu Ser Lys Thr Gly Asp Pro Val Pro Asn Met Glu
                165                 170                 175

Asn Ile Ala Ser Gly Leu Leu Gly Pro Leu Leu Val Leu Gln Ala Gly
            180                 185                 190

Phe Phe Leu Leu Thr Lys Ile Leu Thr Ile Pro Gln Ser Leu Asp Ser
        195                 200                 205

Trp Trp Thr Ser Leu Asn Phe Leu Gly Gly Thr Pro Val Cys Leu Gly
210                 215                 220

Gln Asn Ser Gln Ser Gln Ile Ser Ser His Ser Pro Thr Cys Cys Pro
225                 230                 235                 240

Pro Ile Cys Pro Gly Tyr Arg Trp Met Cys Leu Arg Arg Phe Ile Ile
                245                 250                 255

Phe Leu Cys Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Ser
        275                 280                 285

Thr Thr Ser Thr Gly Ser Cys Lys Thr Cys Thr Thr Pro Ala Gln Gly
    290                 295                 300

Thr Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Val
        355                 360                 365

Ile Trp Met Met Trp Tyr Trp Gly Pro Ser Leu Tyr Asn Ile Leu Ser
    370                 375                 380

Pro Phe Met Pro Leu Leu Pro Ile Phe Phe Cys Leu Trp Val Tyr Ile
385                 390                 395                 400

<210> SEQ ID NO 13
<211> LENGTH: 400
<212> TYPE: PRT
<213> ORGANISM: Hepatitis B virus

<400> SEQUENCE: 13
```

```
Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Lys Ala Asn Ser Glu Asn Pro Asp Trp Asp Leu Asn Pro His
        35                  40                  45

Lys Asp Asn Trp Pro Asp Ala His Lys Val Gly Val Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Ser Val Pro Ala Ala Pro Pro Pro Ala Ser
                85                  90                  95

Thr Asn Arg Gln Ser Gly Arg Gln Pro Thr Pro Leu Ser Pro Pro Leu
            100                 105                 110

Arg Asp Thr His Pro Gln Ala Met Gln Trp Asn Ser Thr Thr Phe His
        115                 120                 125

Gln Thr Leu Gln Asp Pro Arg Val Arg Ala Leu Tyr Phe Pro Ala Gly
    130                 135                 140

Gly Ser Ser Ser Gly Thr Val Ser Pro Ala Gln Asn Thr Val Ser Ala
145                 150                 155                 160

Ile Ser Ser Ile Leu Ser Lys Thr Gly Asp Pro Val Thr Asn Met Glu
                165                 170                 175

Asn Ile Ala Ser Gly Leu Leu Gly Pro Leu Leu Val Leu Gln Ala Gly
            180                 185                 190

Phe Phe Ser Leu Thr Lys Ile Leu Thr Ile Pro Gln Ser Leu Asp Ser
        195                 200                 205

Trp Trp Thr Ser Leu Ser Phe Leu Gly Gly Thr Pro Val Cys Leu Gly
    210                 215                 220

Gln Asn Ser Gln Ser Gln Ile Ser Ser His Ser Pro Thr Cys Cys Pro
225                 230                 235                 240

Pro Ile Cys Pro Gly Tyr Arg Trp Met Cys Leu Arg Arg Phe Ile Ile
                245                 250                 255

Phe Leu Cys Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Ser
        275                 280                 285

Thr Thr Ser Thr Gly Pro Cys Lys Thr Cys Thr Thr Pro Ala Gln Gly
    290                 295                 300

Thr Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Val
        355                 360                 365

Ile Trp Met Met Trp Tyr Trp Gly Pro Ser Leu Tyr Asn Ile Leu Ser
    370                 375                 380

Pro Phe Met Pro Leu Leu Pro Ile Phe Phe Cys Leu Trp Val Tyr Ile
385                 390                 395                 400

<210> SEQ ID NO 14
<211> LENGTH: 400
<212> TYPE: PRT
```

<213> ORGANISM: Hepatitis B virus

<400> SEQUENCE: 14

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Lys Ala Asn Ser Glu Asn Pro Asp Trp Asp Leu Asn Pro His
        35                  40                  45

Lys Asp Asn Trp Pro Asp Ala Asn Lys Val Gly Val Gly Ala Phe Gly
50                  55                  60

Pro Gly Phe Thr Pro Pro His Gly Gly Leu Leu Gly Trp Ser Pro Gln
65                  70                  75                  80

Ala Gln Gly Leu Leu Thr Thr Val Pro Ala Ala Pro Pro Pro Ala Ser
                85                  90                  95

Thr Asn Arg Gln Ser Gly Arg Gln Pro Thr Pro Leu Ser Pro Pro Leu
            100                 105                 110

Arg Asp Thr His Pro Gln Ala Met Gln Trp Asn Ser Thr Thr Phe His
        115                 120                 125

Gln Thr Leu Gln Asp Pro Arg Val Arg Ala Leu Tyr Phe Pro Ala Gly
130                 135                 140

Gly Ser Ser Ser Gly Thr Val Ser Pro Ala Gln Asn Thr Val Ser Thr
145                 150                 155                 160

Ile Ser Ser Ile Leu Ser Lys Thr Gly Asp Pro Val Pro Asn Met Glu
                165                 170                 175

Asn Ile Ala Ser Gly Leu Leu Gly Pro Leu Leu Val Leu Gln Ala Gly
            180                 185                 190

Phe Phe Leu Leu Thr Lys Ile Leu Thr Ile Pro Gln Ser Leu Asp Ser
        195                 200                 205

Trp Trp Thr Ser Leu Asn Phe Leu Gly Gly Thr Pro Val Cys Leu Gly
210                 215                 220

Gln Asn Ser Gln Ser Gln Ile Ser Ser His Ser Pro Thr Cys Cys Pro
225                 230                 235                 240

Pro Ile Cys Pro Gly Tyr Arg Trp Met Cys Leu Arg Arg Phe Ile Ile
                245                 250                 255

Phe Leu Cys Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Ser
        275                 280                 285

Thr Thr Ser Thr Gly Pro Cys Lys Thr Cys Thr Thr Pro Ala Gln Gly
290                 295                 300

Thr Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Val
        355                 360                 365

Ile Trp Met Met Trp Phe Trp Gly Pro Ser Leu Tyr Asn Ile Leu Ser
370                 375                 380

Pro Phe Ile Pro Leu Leu Pro Ile Phe Phe Cys Leu Trp Val Tyr Ile
385                 390                 395                 400

```
<210> SEQ ID NO 15
<211> LENGTH: 400
<212> TYPE: PRT
<213> ORGANISM: Hepatitis B virus

<400> SEQUENCE: 15

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Lys Ala Asn Ser Glu Asn Pro Asp Trp Asp Leu Asn Pro His
        35                  40                  45

Lys Asp Asn Trp Pro Asp Ala Asn Lys Val Gly Val Gly Ala Phe Gly
50                  55                  60

Pro Gly Phe Ile Pro Pro His Gly Gly Leu Met Gly Trp Ser Pro Gln
65                  70                  75                  80

Ala Gln Gly Ile Leu Thr Thr Val Pro Ala Ala Pro Pro Pro Ala Ser
                85                  90                  95

Thr Asn Arg Gln Ser Gly Arg Gln Pro Thr Pro Leu Ser Pro Pro Leu
            100                 105                 110

Arg Asp Thr His Pro Gln Ala Met Gln Trp Asn Ser Thr Thr Phe His
        115                 120                 125

Gln Thr Leu Gln Asp Pro Arg Val Arg Ala Leu Tyr Phe Pro Ala Gly
    130                 135                 140

Gly Ser Ser Ser Gly Thr Val Ser Pro Ala Gln Asn Thr Val Ser Ala
145                 150                 155                 160

Ile Ser Ser Ile Leu Ser Lys Thr Gly Asp Pro Val Pro Asn Met Glu
                165                 170                 175

Asn Ile Ala Ser Gly Leu Leu Gly Pro Leu Leu Val Leu Gln Ala Gly
            180                 185                 190

Phe Phe Ser Leu Thr Lys Ile Leu Thr Ile Pro Gln Ser Leu Asp Ser
        195                 200                 205

Trp Trp Thr Ser Leu Asn Phe Leu Gly Glu Thr Pro Val Cys Leu Gly
210                 215                 220

Gln Asn Ser Gln Ser Gln Ile Ser Ser His Ser Pro Thr Cys Cys Pro
225                 230                 235                 240

Pro Ile Cys Pro Gly Tyr Arg Trp Met Cys Leu Arg Arg Phe Ile Ile
                245                 250                 255

Phe Leu Cys Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Ser
        275                 280                 285

Thr Thr Ser Thr Gly Pro Cys Lys Thr Cys Thr Pro Ala Gln Gly
    290                 295                 300

Thr Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Val Pro
            340                 345                 350

Phe Val Gln Trp Phe Val Gly Leu Ser Pro Thr Val Trp Leu Ser Val
        355                 360                 365

Ile Trp Met Met Trp Tyr Trp Gly Pro Ser Leu Tyr Asn Ile Leu Ser
370                 375                 380
```

Pro Phe Met Pro Leu Leu Pro Ile Phe Phe Cys Leu Trp Val Tyr Ile
385                 390                 395                 400

<210> SEQ ID NO 16
<211> LENGTH: 400
<212> TYPE: PRT
<213> ORGANISM: Hepatitis B virus

<400> SEQUENCE: 16

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Lys Ala Asn Ser Glu Asn Pro Asp Trp Asp Leu Asn Pro His
            35                  40                  45

Lys Asp Asn Trp Pro Asp Ala His Lys Val Gly Val Gly Ala Phe Gly
        50                  55                  60

Pro Gly Phe Thr Pro Pro His Gly Gly Leu Leu Gly Trp Ser Pro Gln
65                  70                  75                  80

Ala Gln Gly Ile Leu Thr Ser Val Pro Ala Ala Pro Pro Pro Ala Ser
                85                  90                  95

Thr Asn Arg Gln Ser Gly Arg Gln Pro Thr Pro Leu Ser Pro Pro Leu
            100                 105                 110

Arg Asp Thr His Pro Gln Ala Val Gln Trp Asn Ser Thr Thr Phe His
        115                 120                 125

Gln Thr Leu Gln Asp Pro Arg Val Arg Ala Leu Tyr Leu Pro Ala Gly
130                 135                 140

Gly Ser Ser Ser Gly Thr Val Ser Pro Ala Gln Asn Thr Val Ser Ala
145                 150                 155                 160

Ile Ser Ser Ile Leu Ser Lys Thr Gly Asp Pro Val Pro Asn Met Glu
                165                 170                 175

Asn Ile Ala Ser Gly Leu Leu Gly Pro Leu Leu Val Leu Gln Ala Gly
            180                 185                 190

Phe Phe Ser Leu Thr Lys Ile Leu Thr Ile Pro Gln Ser Leu Asp Ser
        195                 200                 205

Trp Trp Thr Ser Leu Ser Phe Leu Gly Gly Thr Pro Val Cys Leu Gly
210                 215                 220

Gln Asn Ser Gln Ser Gln Ile Ser Ser His Ser Pro Thr Cys Cys Pro
225                 230                 235                 240

Pro Ile Cys Pro Gly Tyr Arg Trp Met Cys Leu Arg Arg Phe Ile Ile
                245                 250                 255

Phe Leu Cys Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Ser
        275                 280                 285

Thr Thr Ser Thr Gly Pro Cys Lys Thr Cys Thr Thr Pro Ala Gln Gly
290                 295                 300

Thr Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Val

```
                355                 360                 365
Ile Trp Met Met Trp Phe Trp Gly Pro Ser Leu Tyr Asn Ile Leu Ser
            370                 375                 380

Pro Phe Met Pro Leu Leu Pro Ile Phe Leu Cys Leu Trp Val Tyr Met
385                 390                 395                 400

<210> SEQ ID NO 17
<211> LENGTH: 400
<212> TYPE: PRT
<213> ORGANISM: Hepatitis B virus

<400> SEQUENCE: 17

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Lys Ala Asn Ser Asp Asn Pro Asp Trp Asp Leu Asn Pro His
        35                  40                  45

Lys Asp Asn Trp Pro Asp Ser Asn Lys Val Gly Val Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Val Pro Thr Ala Pro Pro Pro Ala Ser
            85                  90                  95

Thr Asn Arg Gln Leu Gly Arg Lys Pro Thr Pro Leu Ser Pro Pro Leu
            100                 105                 110

Arg Asp Thr His Pro Gln Ala Met Gln Trp Asn Ser Thr Thr Phe His
            115                 120                 125

Gln Thr Leu Gln Asp Pro Arg Val Arg Ala Leu Tyr Phe Pro Ala Gly
130                 135                 140

Gly Ser Ser Ser Gly Thr Val Asn Pro Val Gln Asn Thr Ala Ser Ser
145                 150                 155                 160

Ile Ser Ser Ile Leu Ser Thr Thr Gly Asp Pro Val Pro Asn Met Glu
            165                 170                 175

Asn Ile Ala Ser Gly Leu Leu Gly Pro Leu Leu Val Leu Gln Ala Gly
            180                 185                 190

Phe Phe Ser Leu Thr Lys Ile Leu Thr Ile Pro Gln Ser Leu Asp Ser
            195                 200                 205

Trp Trp Thr Ser Leu Asn Phe Leu Gly Gly Thr Pro Val Cys Leu Gly
210                 215                 220

Gln Asn Ser Gln Ser Gln Ile Ser Ser His Ser Pro Thr Cys Cys Pro
225                 230                 235                 240

Pro Ile Cys Pro Gly Tyr Arg Trp Met Cys Leu Arg Arg Phe Ile Ile
            245                 250                 255

Phe Leu Cys Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Ser
            275                 280                 285

Thr Thr Ser Thr Gly Pro Cys Lys Thr Cys Thr Thr Pro Ala Gln Gly
            290                 295                 300

Thr Ser Met Phe Pro Ser Cys Cys Cys Ile Lys Pro Thr Asp Gly Asn
305                 310                 315                 320

Cys Thr Cys Ile Pro Ile Pro Ser Ser Trp Ala Phe Ala Lys Tyr Leu
            325                 330                 335
```

```
Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Val
        355                 360                 365

Ile Trp Met Met Trp Phe Trp Gly Pro Ser Leu Tyr Asn Ile Leu Ser
370                 375                 380

Pro Phe Met Pro Leu Leu Pro Ile Phe Phe Cys Leu Trp Ala Tyr Ile
385                 390                 395                 400

<210> SEQ ID NO 18
<211> LENGTH: 400
<212> TYPE: PRT
<213> ORGANISM: Hepatitis B virus

<400> SEQUENCE: 18

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Lys Ala Asn Ser Asp Asn Pro Asp Trp Asp Leu Asn Pro His
        35                  40                  45

Lys Asp Asn Trp Pro Asp Ser Asn Lys Val Gly Val Gly Ala Phe Gly
50                  55                  60

Pro Gly Phe Thr Pro Pro His Gly Gly Leu Leu Gly Trp Ser Pro Gln
65                  70                  75                  80

Ala Gln Gly Ile Leu Thr Thr Val Pro Thr Ala Pro Pro Pro Ala Ser
                85                  90                  95

Thr Asn Arg Gln Leu Gly Arg Lys Pro Thr Pro Leu Ser Pro Pro Leu
            100                 105                 110

Arg Asp Thr His Pro Gln Ala Met Gln Trp Asn Ser Thr Thr Phe His
        115                 120                 125

Gln Thr Leu Gln Asp Pro Arg Val Arg Ala Leu Tyr Phe Pro Ala Gly
130                 135                 140

Gly Ser Ser Ser Gly Thr Val Asn Pro Val Gln Asn Thr Val Ser Ser
145                 150                 155                 160

Ile Ser Ser Ile Leu Ser Lys Thr Gly Asp Pro Val Pro Asn Met Glu
                165                 170                 175

Asn Ile Ala Ser Gly Leu Leu Gly Pro Leu Leu Val Leu Gln Ala Gly
            180                 185                 190

Phe Phe Leu Leu Thr Lys Ile Leu Thr Ile Pro Gln Ser Leu Asp Ser
        195                 200                 205

Trp Trp Thr Ser Leu Asn Phe Leu Gly Gly Thr Pro Val Cys Leu Gly
210                 215                 220

Gln Asn Ser Gln Ser Gln Ile Ser Ser His Ser Pro Thr Cys Cys Pro
225                 230                 235                 240

Pro Ile Cys Pro Gly Tyr Arg Trp Met Cys Leu Arg Arg Phe Ile Ile
                245                 250                 255

Phe Leu Cys Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Ser
        275                 280                 285

Thr Thr Ser Thr Gly Pro Cys Lys Thr Cys Thr Thr Pro Ala Gln Gly
290                 295                 300

Thr Ser Met Phe Pro Ser Cys Cys Cys Thr Lys Pro Thr Asp Gly Asn
305                 310                 315                 320
```

```
Cys Thr Cys Ile Pro Ile Pro Ser Ser Trp Ala Phe Ala Lys Tyr Leu
            325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Val
            355                 360                 365

Ile Trp Met Met Trp Phe Trp Gly Pro Ser Leu Tyr Asn Ile Leu Ser
370                 375                 380

Pro Phe Met Pro Leu Leu Pro Ile Phe Phe Cys Leu Trp Val Tyr Ile
385                 390                 395                 400

<210> SEQ ID NO 19
<211> LENGTH: 400
<212> TYPE: PRT
<213> ORGANISM: Hepatitis B virus

<400> SEQUENCE: 19

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Lys Gln Val Gly Ala Gly Ala Phe Gly
50                  55                  60

Pro Gly Phe Thr Pro Pro His Gly Gly Leu Leu Gly Trp Ser Pro Gln
65                  70                  75                  80

Ala Gln Gly Thr Leu Thr Thr Val Pro Ala Ala Pro Pro Pro Ala Ser
            85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
            115                 120                 125

Gln Ala Leu Leu Asp Pro Arg Val Arg Gly Leu Tyr Phe Pro Ala Gly
130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn Met Glu
                165                 170                 175

Ser Thr Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
            195                 200                 205

Trp Leu Thr Ser Leu Asn Phe Leu Gly Gly Thr Pro Lys Cys Pro Gly
210                 215                 220

Gln Asn Ser Gln Ser Pro Thr Ser Asn His Ser Pro Thr Ser Cys Pro
225                 230                 235                 240

Pro Thr Cys Pro Gly Tyr Arg Trp Met Cys Leu Arg Arg Phe Ile Ile
            245                 250                 255

Phe Leu Phe Ile Leu Leu Leu Cys Leu Ile Phe Leu Leu Val Leu Leu
            260                 265                 270

Asp Tyr Lys Gly Met Leu Pro Val Cys Pro Leu Leu Pro Gly Thr Ser
            275                 280                 285

Thr Thr Ser Thr Gly Pro Cys Lys Thr Cys Thr Ile Pro Ala Gln Asn
```

```
            290                 295                 300
Thr Ser Met Phe Pro Ser Cys Cys Thr Lys Pro Ser Asp Gly Asn
305                 310                 315                 320

Cys Thr Cys Ile Pro Ile Pro Ser Ser Trp Ala Phe Ala Arg Phe Leu
                    325                 330                 335

Trp Glu Trp Ala Ser Val Arg Phe Ser Trp Leu Ser Leu Leu Val Pro
                340                 345                 350

Phe Val Gln Trp Ser Ala Gly Leu Ser Pro Thr Val Trp Leu Ser Val
            355                 360                 365

Ile Trp Thr Met Trp Tyr Trp Gly Pro Ser Leu Tyr Asn Ile Leu Ser
370                 375                 380

Pro Phe Leu Pro Leu Leu Pro Ile Leu Cys Cys Leu Trp Ala Tyr Ile
385                 390                 395                 400
```

<210> SEQ ID NO 20
<211> LENGTH: 400
<212> TYPE: PRT
<213> ORGANISM: Hepatitis B virus

<400> SEQUENCE: 20

```
Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Gly Ala Asn Ser Asn Asn Pro Asp Trp Asp Phe Asn Pro Asn
            35                  40                  45

Lys Asp His Trp Pro Glu Ala Asn Gln Val Gly Ala Gly Ala Phe Gly
        50                  55                  60

Pro Gly Phe Thr Pro Pro His Gly Gly Leu Leu Gly Arg Ser Pro Gln
65                  70                  75                  80

Ala Gln Gly Ile Leu Thr Thr Val Pro Ala Ala Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Ile Gln Trp Asn Ser Thr Thr Phe His
        115                 120                 125

Gln Ala Leu Leu Asp Pro Lys Val Arg Gly Leu Tyr Leu Pro Ala Gly
130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn Met Glu
                165                 170                 175

Ser Ile Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ala Pro Thr Cys Pro Gly
210                 215                 220

Gln Asn Leu Gln Ser Pro Ile Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270
```

```
Asp Tyr Gln Gly Met Leu Pro Val Cys Pro Leu Leu Pro Gly Thr Ser
            275                 280                 285

Thr Thr Ser Thr Gly Pro Cys Lys Thr Cys Thr Ile Pro Ala Gln Gly
    290                 295                 300

Thr Ser Met Phe Pro Ser Cys Cys Thr Lys Pro Ser Asp Gly Asn
305                 310                 315                 320

Cys Thr Cys Ile Pro Ile Pro Ser Ser Trp Ala Phe Ala Arg Phe Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Val
            355                 360                 365

Ile Trp Met Met Trp Tyr Trp Gly Pro Ser Leu Tyr Asn Ile Leu Asn
370                 375                 380

Pro Phe Leu Pro Leu Leu Pro Ile Phe Phe Cys Leu Trp Val Tyr Ile
385                 390                 395                 400
```

<210> SEQ ID NO 21
<211> LENGTH: 400
<212> TYPE: PRT
<213> ORGANISM: Hepatitis B virus

<400> SEQUENCE: 21

```
Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly Ala Gly Ala Phe Gly
    50                  55                  60

Pro Gly Phe Thr Pro Pro His Gly Gly Leu Leu Gly Arg Ser Pro Gln
65                  70                  75                  80

Ala Gln Gly Ile Leu Thr Thr Val Pro Ala Ala Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Ile Gln Trp Asn Ser Thr Thr Phe His
        115                 120                 125

Gln Ala Leu Leu Asp Pro Lys Val Arg Gly Leu Tyr Leu Pro Ala Gly
    130                 135                 140

Gly Ser Ser Ser Gly Thr Glu Asn Pro Val Pro Thr Thr Ala Ser Pro
145                 150                 155                 160

Ile Ser Ser Ile Phe Ser Arg Thr Gly Asp Pro Ala Pro Asn Met Glu
                165                 170                 175

Ser Thr Thr Ser Gly Phe Leu Gly Pro Leu Leu Val Leu Gln Ala Gly
            180                 185                 190

Phe Phe Leu Leu Thr Arg Ile Leu Thr Ile Pro Gln Arg Leu Asp Ser
        195                 200                 205

Trp Trp Thr Ser Leu Asn Phe Leu Gly Glu Ala Pro Lys Cys Pro Gly
    210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255
```

```
Phe Leu Phe Ile Leu Leu Leu Cys Leu Ile Phe Leu Trp Val Leu Leu
                260                 265                 270

Asp Tyr Gln Gly Met Leu Pro Val Cys Pro Leu Leu Pro Gly Thr Ser
            275                 280                 285

Thr Thr Ser Thr Gly Pro Cys Lys Thr Cys Thr Ile Pro Ala Gln Gly
290                 295                 300

Thr Ser Met Phe Pro Ser Cys Cys Thr Lys Pro Ser Asp Gly Asn
305                 310                 315                 320

Cys Thr Cys Ile Pro Ile Pro Ser Ser Trp Ala Phe Ala Arg Phe Leu
                325                 330                 335

Trp Glu Trp Ala Ser Val Arg Phe Ser Trp Leu Ser Leu Leu Val Pro
            340                 345                 350

Phe Val Gln Trp Phe Ala Gly Leu Ser Pro Thr Val Trp Leu Ser Val
        355                 360                 365

Ile Trp Met Met Trp Tyr Trp Gly Pro Ser Arg Tyr Asn Ile Val Ser
370                 375                 380

Pro Phe Leu Pro Leu Leu Pro Ile Phe Phe Cys Leu Trp Val Tyr Ile
385                 390                 395                 400

<210> SEQ ID NO 22
<211> LENGTH: 400
<212> TYPE: PRT
<213> ORGANISM: Hepatitis B virus

<400> SEQUENCE: 22

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly Ala Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Val Pro Glu Ala Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Ala Leu Leu Asp Pro Arg Val Arg Gly Leu Tyr Leu Pro Ala Gly
    130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn Met Glu
                165                 170                 175

Ser Thr Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ala Pro Thr Cys Pro Gly
    210                 215                 220

Gln Asn Ser Gln Ser Pro Thr Ser Asn His Ser Pro Thr Ser Cys Pro
```

```
                225                 230                 235                 240
Pro Ile Cys Pro Gly Tyr Arg Trp Met Cys Leu Arg Arg Phe Ile Ile
                    245                 250                 255

Phe Leu Phe Ile Leu Leu Leu Cys Leu Ile Phe Leu Trp Val Leu Leu
                    260                 265                 270

Asp Tyr Gln Gly Met Leu Pro Val Cys Pro Leu Leu Pro Gly Thr Ser
                    275                 280                 285

Thr Thr Ser Thr Gly Pro Cys Lys Thr Cys Thr Ser Pro Ala Gln Gly
305                 290                 295                 300

Thr Ser Thr Phe Pro Ser Cys Cys Cys Thr Lys Pro Ser Asp Gly Asn
305                 310                 315                 320

Cys Thr Cys Ile Pro Ile Pro Ser Ser Trp Ala Phe Ala Arg Phe Leu
                    325                 330                 335

Trp Glu Trp Ala Ser Val Arg Phe Ser Trp Leu Ser Leu Leu Val Pro
                    340                 345                 350

Phe Val Gln Trp Phe Ala Gly Leu Ser Pro Thr Val Trp Leu Ser Val
                    355                 360                 365

Ile Trp Met Met Trp Tyr Trp Gly Pro Ser Leu Tyr Asn Ile Leu Ser
                    370                 375                 380

Pro Phe Leu Pro Leu Leu Pro Ile Phe Phe Cys Leu Trp Val Tyr Ile
385                 390                 395                 400
```

<210> SEQ ID NO 23
<211> LENGTH: 400
<212> TYPE: PRT
<213> ORGANISM: Hepatitis B virus

<400> SEQUENCE: 23

```
Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Gly Ala Asn Ser Asn Asn Pro Asp Trp Asp Phe Asn Pro Asn
                35                  40                  45

Lys Asp Gln Trp Pro Glu Ala Asn Gln Val Gly Ala Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Val Pro Ala Ala Pro Pro Pro Ala Ser
                85                  90                  95

Thr Asn Arg Gln Ser Gly Arg Gln Pro Thr Pro Ile Ser Pro Pro Leu
                100                 105                 110

Arg Asp Ser His Pro Gln Ala Met Gln Trp Asn Ser Thr Thr Phe His
                115                 120                 125

Gln Ala Leu Leu Asp Pro Arg Val Arg Gly Leu Tyr Phe Pro Ala Gly
                130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn Met Glu
                165                 170                 175

Asn Thr Thr Ser Gly Phe Leu Gly Pro Leu Leu Val Leu Gln Ala Gly
                180                 185                 190

Phe Phe Leu Leu Thr Arg Ile Leu Thr Ile Pro Gln Ser Leu Asp Ser
                195                 200                 205
```

```
Trp Trp Thr Ser Leu Asn Phe Leu Gly Gly Ala Pro Thr Cys Pro Gly
        210                 215                 220
Gln Asn Ser Gln Ser Pro Thr Ser Asn His Ser Pro Thr Ser Cys Pro
225                 230                 235                 240
Pro Ile Cys Pro Gly Tyr Arg Trp Met Cys Leu Arg Arg Phe Ile Ile
                245                 250                 255
Phe Leu Phe Ile Leu Leu Leu Cys Leu Ile Phe Leu Leu Val Leu Leu
            260                 265                 270
Asp Tyr Gln Gly Met Leu Pro Val Cys Pro Leu Leu Pro Gly Thr Ser
                275                 280                 285
Thr Thr Ser Thr Gly Pro Cys Lys Thr Cys Thr Ile Pro Ala Gln Gly
290                 295                 300
Thr Ser Met Phe Pro Ser Cys Cys Cys Thr Lys Pro Ser Asp Gly Asn
305                 310                 315                 320
Cys Thr Cys Ile Pro Ile Pro Ser Ser Trp Ala Phe Ala Arg Phe Leu
                325                 330                 335
Trp Glu Trp Ala Ser Val Arg Phe Ser Trp Leu Ser Leu Leu Val Pro
                340                 345                 350
Phe Val Gln Trp Phe Val Gly Leu Ser Pro Thr Val Trp Leu Ser Val
            355                 360                 365
Ile Trp Met Met Trp Tyr Trp Gly Pro Ser Leu Tyr Asn Ile Leu Ser
370                 375                 380
Pro Phe Leu Pro Leu Leu Pro Ile Phe Phe Cys Leu Trp Val Tyr Ile
385                 390                 395                 400
```

<210> SEQ ID NO 24
<211> LENGTH: 400
<212> TYPE: PRT
<213> ORGANISM: Hepatitis B virus

<400> SEQUENCE: 24

```
Met Gly Gly Trp Ser Ser Lys Pro Arg Gln Gly Met Gly Thr Asn Leu
1               5                   10                  15
Ser Val Pro Asn Pro Leu Gly Phe Phe Pro Asp His Gln Leu Asp Pro
            20                  25                  30
Ala Phe Gly Ala Asn Ser His Asn Pro Asp Trp Asp Phe Asn Pro Asn
        35                  40                  45
Lys Asp His Trp Pro Glu Ala Asn Gln Val Gly Ala Gly Ala Phe Gly
50                  55                  60
Pro Gly Phe Thr Pro Pro His Gly Gly Leu Leu Gly Trp Ser Pro Gln
65                  70                  75                  80
Ala Gln Gly Val Leu Thr Thr Val Pro Val Ala Pro Pro Ala Ser
            85                  90                  95
Thr Asn Arg Gln Ser Gly Arg Gln Pro Thr Pro Ile Ser Pro Pro Leu
            100                 105                 110
Arg Asp Ser His Pro Gln Ala Met Gln Trp Asn Ser Thr Thr Phe His
            115                 120                 125
Gln Ala Leu Leu Asp Pro Arg Val Arg Gly Leu Tyr Phe Pro Ala Gly
            130                 135                 140
Gly Ser Ser Ser Gly Thr Val Asn Pro Val Pro Thr Thr Ala Ser Pro
145                 150                 155                 160
Ile Ser Ser Ile Ser Ser Arg Thr Gly Asp Pro Ala Pro Asn Met Glu
                165                 170                 175
Asn Thr Thr Ser Gly Phe Leu Gly Pro Leu Leu Val Leu Gln Ala Gly
            180                 185                 190
```

-continued

Phe Phe Leu Leu Thr Arg Ile Leu Thr Ile Pro Gln Ser Leu Asp Ser
            195                 200                 205

Trp Trp Thr Ser Leu Asn Phe Leu Gly Gly Ala Pro Thr Cys Pro Gly
    210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Leu Pro Gly Thr Ser
            275                 280                 285

Thr Thr Ser Thr Gly Pro Cys Lys Thr Cys Thr Ile Pro Ala Gln Gly
    290                 295                 300

Thr Ser Met Phe Pro Ser Cys Cys Cys Thr Lys Pro Ser Asp Gly Asn
305                 310                 315                 320

Cys Thr Cys Ile Pro Ile Pro Ser Ser Trp Ala Phe Ala Arg Phe Leu
                325                 330                 335

Trp Glu Gly Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Val
            355                 360                 365

Ile Trp Met Met Trp Tyr Trp Gly Pro Ser Leu Tyr Asn Ile Leu Ser
    370                 375                 380

Pro Phe Leu Pro Leu Leu Pro Ile Phe Phe Cys Leu Trp Val Tyr Ile
385                 390                 395                 400

<210> SEQ ID NO 25
<211> LENGTH: 399
<212> TYPE: PRT
<213> ORGANISM: Hepatitis B virus

<400> SEQUENCE: 25

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly Val Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Val Pro Ala Ala Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Ala Leu Leu Asp Pro Arg Val Arg Gly Leu Tyr Phe Pro Ala Gly
    130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn Met Glu

```
            165                 170                 175
Asn Thr Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
            195                 200                 205

Trp Thr Ser Leu Asn Phe Leu Gly Gly Ala Pro Thr Cys Pro Gly Gln
            210                 215                 220

Asn Ser Gln Ser Pro Thr Ser Asn His Ser Pro Thr Ser Cys Pro Pro
225                 230                 235                 240

Ile Cys Pro Gly Tyr Arg Trp Met Cys Leu Arg Arg Phe Ile Ile Phe
            245                 250                 255

Leu Phe Ile Leu Leu Leu Cys Leu Ile Phe Leu Leu Ala Leu Leu Asp
            260                 265                 270

Tyr Gln Gly Met Leu Pro Val Cys Pro Leu Leu Pro Gly Thr Ser Thr
            275                 280                 285

Thr Ser Thr Gly Pro Cys Lys Thr Cys Thr Ile Pro Ala Gln Gly Thr
            290                 295                 300

Ser Met Phe Pro Ser Cys Cys Cys Thr Lys Pro Ser Asp Gly Asn Cys
305                 310                 315                 320

Thr Cys Ile Pro Ile Pro Ser Ser Trp Ala Phe Ala Arg Phe Leu Trp
            325                 330                 335

Glu Trp Ala Ser Val Arg Phe Ser Trp Leu Ser Leu Leu Val Pro Phe
            340                 345                 350

Val Gln Trp Phe Ala Gly Leu Ser Pro Thr Val Trp Leu Ser Val Ile
            355                 360                 365

Trp Met Met Trp Tyr Trp Gly Pro Ser Leu Tyr Asn Ile Leu Ser Pro
            370                 375                 380

Phe Ile Pro Leu Leu Pro Ile Phe Leu Cys Leu Trp Val Tyr Ile
385                 390                 395

<210> SEQ ID NO 26
<211> LENGTH: 400
<212> TYPE: PRT
<213> ORGANISM: Hepatitis B virus

<400> SEQUENCE: 26

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
            35                  40                  45

Lys Asp Gln Trp Pro Ala Ala Asn Gln Val Gly Val Gly Ala Phe Gly
            50                  55                  60

Pro Gly Phe Thr Pro Pro His Gly Asn Leu Leu Gly Trp Ser Pro Gln
65                  70                  75                  80

Ala Gln Gly Ile Leu Thr Thr Val Pro Ala Ala Pro Pro Pro Ala Ser
            85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Ser Thr Phe His
            115                 120                 125

Gln Ala Leu Leu Asp Pro Arg Val Arg Gly Leu Tyr Leu Pro Ala Gly
            130                 135                 140
```

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn Met Glu
            165                 170                 175

Ser Thr Thr Ser Gly Phe Leu Gly Pro Leu Val Leu Gln Ala Gly
        180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ala Pro Thr Cys Pro Gly
210                 215                 220

Gln Asn Ser Gln Ser Pro Thr Ser Asn His Ser Leu Thr Ser Cys Pro
225                 230                 235                 240

Pro Ile Cys Pro Gly Tyr Arg Trp Met Cys Leu Arg Arg Phe Ile Ile
            245                 250                 255

Phe Leu Phe Ile Leu Leu Leu Cys Leu Ile Phe Leu Leu Val Leu Leu
        260                 265                 270

Asp Tyr Gln Gly Met Leu Pro Val Cys Pro Leu Leu Pro Gly Thr Ser
            275                 280                 285

Thr Thr Ser Thr Gly Pro Cys Lys Thr Cys Thr Thr Pro Ala Gln Gly
        290                 295                 300

Thr Ser Met Phe Pro Ser Cys Cys Cys Thr Lys Pro Ser Asp Gly Asn
305                 310                 315                 320

Cys Thr Cys Ile Pro Ile Pro Ser Ser Trp Ala Phe Ala Arg Phe Leu
            325                 330                 335

Trp Glu Trp Ala Ser Val Arg Phe Ser Trp Leu Ser Leu Leu Val Pro
        340                 345                 350

Phe Val Gln Trp Phe Val Gly Leu Ser Pro Thr Val Trp Leu Ser Val
            355                 360                 365

Ile Trp Met Met Trp Tyr Trp Gly Pro Ser Leu Tyr Asn Ile Leu Asn
        370                 375                 380

Pro Phe Leu Pro Leu Phe Pro Ile Phe Phe Cys Leu Trp Val Tyr Ile
385                 390                 395                 400

<210> SEQ ID NO 27
<211> LENGTH: 400
<212> TYPE: PRT
<213> ORGANISM: Hepatitis B virus

<400> SEQUENCE: 27

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly Ala Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Val Pro Ala Ala Pro Pro Ser Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe Gln
        115                 120                 125

Gln Ala Leu Gln Asp Pro Arg Val Arg Val Leu Tyr Phe Pro Ala Gly
                130                 135                 140

Gly Ser Ser Ser Gly Thr Val Asn Pro Val Pro Thr Thr Ala Ser Leu
145                 150                 155                 160

Ile Ser Ser Ile Phe Ser Arg Ile Gly Asp Pro Val Thr Asn Met Glu
                165                 170                 175

Asn Thr Thr Ser Gly Phe Leu Gly Pro Leu Leu Val Leu Gln Ala Gly
                180                 185                 190

Phe Phe Leu Leu Thr Lys Ile Leu Thr Ile Pro Gln Ser Leu Asp Ser
                195                 200                 205

Trp Trp Thr Ser Leu Asn Phe Leu Gly Gly Ala Pro Val Cys Pro Gly
                210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
                260                 265                 270

Asp Tyr Gln Gly Met Leu Pro Val Cys Pro Leu Leu Pro Gly Thr Ser
                275                 280                 285

Thr Thr Ser Thr Gly Pro Cys Lys Thr Cys Thr Ile Pro Ala Gln Gly
                290                 295                 300

Thr Ser Met Phe Pro Ser Cys Cys Cys Thr Lys Pro Ser Asp Gly Asn
305                 310                 315                 320

Cys Thr Cys Ile Pro Ile Pro Ser Ser Trp Ala Phe Val Arg Phe Leu
                325                 330                 335

Trp Glu Trp Ala Ser Val Arg Phe Ser Trp Leu Ser Leu Leu Ala Pro
                340                 345                 350

Phe Val Gln Trp Phe Val Gly Leu Ser Pro Thr Val Trp Leu Ser Val
                355                 360                 365

Ile Trp Met Met Trp Tyr Trp Gly Pro Ser Leu Tyr Asn Ile Leu Ser
                370                 375                 380

Pro Phe Ile Pro Leu Leu Pro Ile Phe Phe Cys Leu Trp Val Tyr Ile
385                 390                 395                 400

<210> SEQ ID NO 28
<211> LENGTH: 400
<212> TYPE: PRT
<213> ORGANISM: Hepatitis B virus

<400> SEQUENCE: 28

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Gly Ala Asn Ser Asn Asn Pro Asp Trp Asp Phe Asn Pro Asn
                35                  40                  45

Lys Asp Arg Trp Pro Glu Ala Asn Gln Val Gly Ala Gly Ala Phe Gly
                50                  55                  60

Pro Gly Tyr Pro Pro Pro His Gly Gly Leu Leu Gly Trp Ser Pro Gln
65                  70                  75                  80

Ala Gln Gly Ile Leu Thr Thr Val Pro Ala Ala Pro Pro Pro Ala Ser
                85                  90                  95

Thr Asn Arg Gln Ser Gly Arg Gln Pro Thr Pro Ile Ser Pro Pro Leu

```
                100             105             110
Arg Asp Ser His Pro Gln Ala Met Gln Trp Asn Ser Thr Thr Phe His
            115                 120                 125
Gln Val Leu Leu Asp Pro Arg Val Arg Gly Leu Tyr Phe Pro Pro Gly
    130                 135                 140
Gly Ser Ser Ser Gly Thr Val Asn Pro Val Ala Thr Thr Ala Ser Pro
145                 150                 155                 160
Ile Ser Ser Ile Ser Ser Arg Thr Gly Asp Pro Ala Pro Asn Met Glu
                165                 170                 175
Ser Thr Thr Ser Gly Phe Leu Gly Pro Leu Leu Val Leu Gln Ala Gly
            180                 185                 190
Phe Phe Leu Leu Thr Arg Ile Leu Thr Ile Pro Gln Ser Leu Asp Ser
        195                 200                 205
Trp Trp Thr Ser Leu Asn Phe Leu Gly Gly Ala Pro Thr Cys Pro Gly
        210                 215                 220
Gln Asn Ser Gln Ser Pro Thr Ser Asn His Ser Pro Thr Ser Cys Pro
225                 230                 235                 240
Pro Ile Cys Pro Gly Tyr Arg Trp Met Cys Leu Arg Arg Phe Ile Ile
                245                 250                 255
Phe Leu Phe Ile Leu Leu Leu Cys Leu Ile Phe Leu Leu Val Leu Leu
                260                 265                 270
Asp Tyr Gln Gly Met Leu Pro Val Cys Pro Leu Leu Pro Gly Thr Ser
            275                 280                 285
Thr Thr Ser Thr Gly Pro Cys Lys Thr Cys Thr Ile Pro Ala Gln Gly
        290                 295                 300
Thr Ser Met Phe Pro Ser Cys Cys Cys Thr Lys Pro Ser Asp Gly Asn
305                 310                 315                 320
Cys Thr Cys Ile Pro Ile Pro Ser Ser Trp Ala Phe Ala Arg Phe Leu
                325                 330                 335
Trp Glu Gly Ala Ser Val Arg Phe Ser Trp Leu Ser Leu Leu Val Pro
            340                 345                 350
Phe Val Gln Trp Phe Val Gly Leu Ser Pro Thr Val Trp Leu Ser Val
        355                 360                 365
Ile Trp Met Met Trp Tyr Trp Gly Pro Ser Leu Tyr Asn Ile Leu Ser
        370                 375                 380
Pro Phe Leu Pro Leu Leu Pro Ile Phe Phe Cys Leu Trp Val Tyr Ile
385                 390                 395                 400

<210> SEQ ID NO 29
<211> LENGTH: 389
<212> TYPE: PRT
<213> ORGANISM: Hepatitis B virus

<400> SEQUENCE: 29

Met Gly Gln Asn Leu Ser Thr Ser Asn Pro Leu Gly Phe Phe Pro Asp
1               5                   10                  15

His Gln Leu Asp Pro Ala Ser Arg Ala Asn Thr Ala Asn Pro Asp Trp
            20                  25                  30

Asp Phe Asn Pro Asn Lys Asp Thr Trp Pro Asp Ala Asn Lys Asp Gly
        35                  40                  45

Ala Gly Ala Phe Gly Leu Gly Leu Thr Pro Pro His Gly Gly Leu Leu
    50                  55                  60

Gly Trp Ser Pro Gln Ala Gln Gly Ile Leu His Thr Val Pro Ala Asn
65                  70                  75                  80
```

```
Pro Pro Pro Ala Ser Thr Asn Arg Gln Thr Gly Arg Gln Pro Thr Pro
                85                  90                  95

Leu Ser Pro Pro Leu Arg Asp Thr His Pro Gln Ala Val Gln Trp Asn
            100                 105                 110

Ser Thr Thr Phe His Gln Thr Leu Gln Asp Pro Arg Val Arg Gly Leu
        115                 120                 125

Tyr Phe Pro Ala Gly Gly Ser Ser Gly Thr Val Asn Pro Val Pro
    130                 135                 140

Thr Thr Ala Ser Pro Leu Ser Ser Ile Phe Ser Arg Ile Gly Asp Pro
145                 150                 155                 160

Val Thr Asn Met Glu Asn Ile Thr Ser Gly Phe Leu Gly Pro Leu Leu
                165                 170                 175

Val Leu Gln Ala Gly Phe Phe Leu Leu Thr Arg Ile Leu Thr Ile Pro
            180                 185                 190

Gln Ser Leu Asp Ser Trp Trp Thr Ser Leu Asn Phe Arg Gly Gly Thr
        195                 200                 205

Thr Val Cys Leu Gly Gln Asn Ser Gln Ser Pro Thr Ser Asn His Ser
    210                 215                 220

Pro Thr Ser Cys Pro Pro Thr Cys Pro Gly Tyr Arg Trp Met Cys Leu
225                 230                 235                 240

Arg Gly Phe Ile Ile Phe Leu Phe Ile Leu Leu Leu Cys Leu Ile Phe
                245                 250                 255

Leu Leu Val Leu Leu Glu Tyr Gln Gly Met Leu His Val Cys Pro Leu
            260                 265                 270

Ile Pro Gly Thr Thr Thr Thr Ser Thr Gly Pro Cys Lys Thr Cys Thr
        275                 280                 285

Thr Pro Ala Gln Gly Asn Ser Met Phe Pro Ser Cys Cys Cys Thr Lys
    290                 295                 300

Thr Ser Asp Gly Asn Cys Thr Cys Ile Pro Ile Pro Ser Ser Trp Ala
305                 310                 315                 320

Phe Ala Lys Tyr Leu Trp Glu Trp Ala Ser Val Arg Phe Ser Trp Leu
                325                 330                 335

Ser Leu Leu Val Pro Phe Val Gln Trp Phe Val Gly Leu Ser Pro Thr
            340                 345                 350

Val Trp Leu Ser Ala Ile Trp Met Met Trp Tyr Trp Gly Pro Ser Leu
        355                 360                 365

Tyr Ser Ile Leu Ser Pro Phe Leu Pro Leu Leu Pro Ile Phe Phe Cys
    370                 375                 380

Leu Trp Val Tyr Ile
385

<210> SEQ ID NO 30
<211> LENGTH: 389
<212> TYPE: PRT
<213> ORGANISM: Hepatitis B virus

<400> SEQUENCE: 30

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly
        35                  40                  45

Ala Gly Ala Phe Gly Leu Gly Phe Thr Pro Pro Gln Gly Gly Leu Leu
    50                  55                  60
```

Gly Trp Asn Pro Gly Ala Gln Gly Ile Ile Gln Thr Leu Pro Ala Asn
 65                  70                  75                  80

Pro Pro Pro Ala Ser Thr Asn Arg Gln Ser Gly Arg Gln Pro Thr Pro
                 85                  90                  95

Leu Thr Pro Pro Leu Arg Asn Thr His Pro Gln Ala Met Gln Trp Asn
            100                 105                 110

Ser Thr Thr Phe His Gln Thr Leu Gln Asp Pro Arg Val Arg Gly Leu
        115                 120                 125

Tyr Phe Pro Ala Gly Gly Ser Ser Gly Thr Val Asn Pro Val Pro
130                 135                 140

Thr Thr Val Ser His Ile Ser Ser Ile Phe Ser Arg Ile Gly Val Pro
145                 150                 155                 160

Ala Leu Asn Met Glu Asn Ile Thr Ser Gly Phe Leu Gly Pro Leu Leu
                165                 170                 175

Val Leu Gln Ala Gly Phe Phe Leu Leu Thr Arg Ile Leu Thr Ile Pro
            180                 185                 190

Gln Ser Leu Asp Ser Trp Trp Thr Ser Leu Asn Phe Leu Gly Gly Thr
        195                 200                 205

Thr Val Cys Leu Gly Gln Asn Ser Gln Ser Pro Thr Ser Asn His Ser
210                 215                 220

Pro Thr Ser Cys Pro Pro Thr Cys Pro Gly Tyr Arg Trp Met Cys Leu
225                 230                 235                 240

Arg Arg Phe Ile Ile Phe Leu Phe Ile Leu Leu Leu Cys Leu Ile Leu
                245                 250                 255

Leu Leu Leu Leu Leu Asp Tyr Gln Gly Met Leu Pro Val Cys Pro Leu
            260                 265                 270

Ile Pro Gly Ser Ser Thr Thr Ser Val Gly Pro Cys Arg Thr Cys Thr
        275                 280                 285

Thr Pro Val Gln Gly Thr Ser Met Tyr Pro Ser Cys Cys Cys Thr Lys
290                 295                 300

Pro Ser Asp Gly Asn Cys Thr Cys Ile Pro Ile Pro Ser Ser Trp Ala
305                 310                 315                 320

Phe Gly Lys Phe Leu Trp Glu Trp Ala Ser Ala Arg Phe Ser Trp Leu
                325                 330                 335

Ser Leu Leu Val Pro Phe Val Gln Trp Phe Val Gly Leu Ser Pro Thr
            340                 345                 350

Val Trp Leu Ser Val Ile Trp Met Met Trp Tyr Trp Gly Pro Ser Leu
        355                 360                 365

Tyr Arg Ile Leu Ser Pro Phe Leu Pro Leu Leu Pro Ile Phe Phe Cys
370                 375                 380

Leu Trp Val Tyr Ile
385

<210> SEQ ID NO 31
<211> LENGTH: 389
<212> TYPE: PRT
<213> ORGANISM: Hepatitis B virus

<400> SEQUENCE: 31

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly

```
                35                  40                  45
Ala Gly Ala Phe Gly Leu Gly Phe Thr Pro Pro His Gly Gly Leu Leu
 50                  55                  60

Gly Trp Ser Pro Gln Ala Gln Gly Met Leu Gln Thr Leu Pro Ala Asn
 65                  70                  75                  80

Pro Pro Pro Ala Ser Thr Asn Arg Gln Ser Gly Arg Gln Pro Thr Pro
                 85                  90                  95

Leu Ser Pro Pro Leu Arg Asn Thr His Pro Gln Ala Met His Trp Asn
                100                 105                 110

Ser Thr Thr Phe His Gln Thr Leu Gln Asp Pro Arg Val Arg Gly Leu
                115                 120                 125

Tyr Phe Pro Ala Gly Gly Ser Asn Ser Gly Thr Val Asn Pro Val Pro
                130                 135                 140

Thr Thr Ala Ser His Leu Ser Ser Ile Phe Ser Arg Ile Gly Asp Pro
145                 150                 155                 160

Ala Leu Asn Met Glu Ser Ile Thr Ser Gly Phe Leu Gly Pro Leu Leu
                165                 170                 175

Val Leu Gln Ala Gly Phe Phe Leu Leu Thr Arg Ile Leu Thr Ile Pro
                180                 185                 190

Gln Ser Leu Asp Ser Trp Trp Thr Ser Leu Asn Phe Leu Gly Gly Thr
                195                 200                 205

Thr Val Cys Leu Gly Gln Asn Ser Gln Ser Pro Thr Ser Asn His Ser
210                 215                 220

Pro Thr Ser Cys Pro Pro Thr Cys Pro Gly Tyr Arg Trp Met Cys Leu
225                 230                 235                 240

Arg Arg Phe Ile Ile Phe Leu Phe Ile Leu Leu Leu Cys Leu Ile Phe
                245                 250                 255

Leu Leu Val Leu Leu Asp Tyr Gln Gly Met Leu Pro Val Cys Pro Leu
                260                 265                 270

Ile Pro Gly Ser Ser Thr Thr Ser Thr Gly Pro Cys Arg Thr Cys Thr
                275                 280                 285

Thr Pro Ala Gln Gly Thr Ser Met Tyr Pro Ser Cys Cys Cys Thr Lys
290                 295                 300

Pro Ser Asp Gly Asn Cys Thr Cys Ile Pro Ile Pro Ser Ser Trp Ala
305                 310                 315                 320

Phe Gly Lys Phe Leu Trp Glu Trp Ala Ser Ala Arg Phe Ser Trp Leu
                325                 330                 335

Ser Leu Leu Val Pro Phe Val Gln Trp Phe Val Gly Leu Ser Pro Thr
                340                 345                 350

Val Trp Leu Ser Val Ile Trp Met Met Trp Tyr Trp Gly Pro Ser Leu
                355                 360                 365

Tyr Ser Ile Leu Ser Pro Phe Leu Pro Leu Leu Pro Ile Phe Phe Cys
                370                 375                 380

Leu Trp Val Tyr Ile
385

<210> SEQ ID NO 32
<211> LENGTH: 389
<212> TYPE: PRT
<213> ORGANISM: Hepatitis B virus

<400> SEQUENCE: 32

Met Gly Gln Asn Leu Ser Thr Ser Asn Pro Leu Gly Phe Phe Pro Asp
 1               5                  10                  15
```

His Gln Leu Asp Pro Ala Phe Arg Ala Asn Thr Ala Asn Pro Asp Trp
             20                  25                  30

Asp Phe Asn Pro Asn Lys Asp Thr Trp Pro Asp Ala Asn Lys Val Gly
             35                  40                  45

Ala Gly Ala Phe Gly Leu Gly Phe Thr Pro Pro His Gly Gly Leu Leu
 50                      55                  60

Gly Trp Ser Pro Gln Ala Gln Gly Ile Leu Gln Thr Leu Pro Ala Asn
 65              70                  75                      80

Pro Pro Ser Ala Ser Thr Asn Arg Gln Ser Gly Arg Gln Pro Thr Pro
                 85                  90                  95

Leu Ser Pro Pro Leu Arg Asn Thr His Pro Gln Ala Met Gln Trp Asn
             100                 105                 110

Ser Thr Thr Phe His Gln Thr Leu Gln Asp Pro Arg Val Arg Gly Leu
             115                 120                 125

Tyr Phe Pro Ala Gly Gly Ser Gly Ser Gly Thr Val Asn Pro Val Pro
             130                 135                 140

Thr Thr Ala Ser Pro Leu Ser Ser Ile Phe Ser Arg Ile Gly Asp Pro
145                 150                 155                 160

Ala Leu Asn Met Glu Asn Ile Thr Ser Gly Phe Leu Gly Pro Leu Leu
                 165                 170                 175

Val Leu Gln Ala Gly Phe Phe Leu Leu Thr Arg Ile Leu Thr Ile Pro
             180                 185                 190

Gln Ser Leu Asp Ser Trp Trp Thr Ser Leu Asn Phe Leu Gly Gly Thr
             195                 200                 205

Thr Val Cys Leu Gly Gln Asn Ser Gln Ser Pro Thr Ser Asn His Ser
210                 215                 220

Pro Thr Ser Cys Pro Pro Thr Cys Pro Gly Tyr Arg Trp Met Cys Leu
225                 230                 235                 240

Arg Arg Phe Ile Ile Phe Leu Phe Ile Leu Leu Cys Leu Ile Phe
                 245                 250                 255

Leu Leu Val Leu Leu Asp Tyr Gln Gly Met Leu Pro Val Cys Pro Leu
             260                 265                 270

Ile Pro Gly Ser Ser Thr Thr Ser Thr Gly Pro Cys Arg Thr Cys Thr
             275                 280                 285

Thr Pro Ala Gln Gly Thr Ser Met Tyr Pro Ser Cys Cys Cys Thr Lys
290                 295                 300

Pro Ser Asp Gly Asn Cys Thr Cys Ile Pro Ile Pro Ser Ser Trp Ala
305                 310                 315                 320

Phe Gly Lys Phe Leu Trp Glu Trp Ala Ser Ala Arg Phe Ser Trp Leu
                 325                 330                 335

Ser Leu Leu Val Pro Phe Val Gln Trp Phe Val Gly Leu Ser Pro Thr
             340                 345                 350

Val Trp Leu Ser Val Ile Trp Met Met Trp Tyr Trp Gly Pro Ser Leu
             355                 360                 365

Tyr Ser Ile Leu Ser Pro Phe Leu Pro Leu Leu Pro Ile Phe Phe Cys
             370                 375                 380

Leu Trp Val Tyr Ile
385

<210> SEQ ID NO 33
<211> LENGTH: 389
<212> TYPE: PRT
<213> ORGANISM: Hepatitis B virus

<400> SEQUENCE: 33

```
Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly
                35                  40                  45

Ala Gly Ala Phe Gly Leu Gly Phe Thr Pro Pro His Gly Gly Leu Leu
        50                  55                  60

Gly Trp Ser Pro Gln Ala Gln Gly Ile Leu Gln Thr Leu Pro Ala Asn
65                  70                  75                  80

Pro Pro Pro Ala Ser Thr Asn Arg Gln Ser Gly Arg Gln Pro Thr Pro
                85                  90                  95

Leu Ser Pro Pro Leu Arg Asn Thr His Pro Gln Ala Met Gln Trp Asn
                100                 105                 110

Ser Thr Thr Phe His Gln Thr Leu Gln Asp Pro Arg Val Arg Gly Leu
            115                 120                 125

Tyr Phe Pro Ala Gly Gly Ser Ser Gly Thr Val Asn Pro Val Pro
130                 135                 140

Thr Thr Val Ser Pro Ile Ser Ser Ile Phe Ser Arg Ile Gly Asp Pro
145                 150                 155                 160

Ala Leu Asn Met Glu Asn Ile Thr Ser Gly Phe Leu Gly Pro Leu Leu
                165                 170                 175

Val Leu Gln Ala Gly Phe Phe Leu Leu Thr Arg Ile Leu Thr Ile Pro
                180                 185                 190

Gln Ser Leu Asp Ser Trp Trp Thr Ser Leu Asn Phe Leu Gly Gly Thr
            195                 200                 205

Thr Val Cys Leu Gly Gln Asn Ser Gln Ser Pro Thr Ser Asn His Ser
210                 215                 220

Pro Thr Ser Cys Pro Pro Thr Cys Pro Gly Tyr Arg Trp Met Cys Leu
225                 230                 235                 240

Arg Arg Phe Ile Ile Phe Leu Phe Ile Leu Leu Leu Cys Leu Ile Phe
                245                 250                 255

Leu Leu Val Leu Leu Asp Tyr Gln Gly Met Leu Pro Val Cys Pro Leu
                260                 265                 270

Ile Pro Gly Ser Ser Thr Thr Ser Thr Gly Pro Cys Arg Thr Cys Thr
            275                 280                 285

Thr Pro Ala Gln Gly Thr Ser Met Tyr Pro Ser Cys Cys Cys Thr Lys
            290                 295                 300

Pro Ser Asp Gly Asn Cys Thr Cys Ile Pro Ile Pro Ser Ser Trp Ala
305                 310                 315                 320

Phe Gly Lys Phe Leu Trp Glu Trp Ala Ser Ala Arg Phe Ser Trp Leu
                325                 330                 335

Ser Leu Leu Val Pro Phe Val Gln Trp Phe Val Gly Leu Ser Pro Thr
            340                 345                 350

Val Trp Leu Ser Val Ile Trp Met Met Trp Tyr Trp Gly Pro Ser Leu
            355                 360                 365

Tyr Ser Ile Leu Ser Pro Phe Leu Pro Leu Leu Pro Ile Phe Phe Cys
370                 375                 380

Leu Trp Val Tyr Ile
385

<210> SEQ ID NO 34
<211> LENGTH: 389
```

```
<212> TYPE: PRT
<213> ORGANISM: Hepatitis B virus

<400> SEQUENCE: 34

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly
        35                  40                  45

Ala Gly Ala Phe Gly Leu Gly Phe Thr Pro Pro His Gly Gly Leu Leu
    50                  55                  60

Gly Trp Ser Pro Gln Ala Gln Gly Ile Leu His Thr Val Pro Ala Asn
65                  70                  75                  80

Pro Pro Pro Ala Ser Thr Asn Arg Gln Ser Gly Arg Gln Pro Thr Pro
                85                  90                  95

Leu Ser Pro Pro Leu Arg Asn Thr His Pro Gln Ala Met Gln Trp Asn
            100                 105                 110

Ser Thr Thr Phe His Gln Thr Leu Gln Asp Pro Arg Val Arg Gly Leu
        115                 120                 125

Tyr Phe Pro Ala Gly Gly Ser Ser Gly Thr Val Asn Pro Val Leu
    130                 135                 140

Thr Thr Ala Ser Pro Leu Ser Ser Ile Ser Ala Arg Thr Gly Asp Pro
145                 150                 155                 160

Ala Leu Asn Met Glu Asn Ile Thr Ser Gly Phe Leu Gly Pro Leu Leu
                165                 170                 175

Val Leu Gln Ala Gly Phe Phe Leu Leu Thr Arg Ile Leu Thr Ile Pro
            180                 185                 190

Gln Ser Leu Asp Ser Trp Trp Thr Ser Leu Asn Phe Leu Gly Gly Thr
        195                 200                 205

Thr Val Cys Leu Gly Gln Asn Ser Gln Ser Pro Thr Ser Asn His Ser
210                 215                 220

Pro Thr Ser Cys Pro Pro Thr Cys Pro Gly Tyr Arg Trp Met Cys Leu
225                 230                 235                 240

Arg Arg Phe Ile Ile Phe Leu Phe Ile Leu Leu Leu Cys Leu Ile Phe
                245                 250                 255

Leu Leu Val Leu Leu Asp Tyr Gln Gly Met Leu Pro Val Cys Pro Leu
            260                 265                 270

Ile Pro Gly Ser Ser Thr Thr Ser Thr Gly Pro Cys Arg Thr Cys Thr
        275                 280                 285

Thr Pro Ala Gln Gly Thr Ser Met Tyr Pro Ser Cys Cys Cys Thr Lys
    290                 295                 300

Pro Ser Asp Gly Asn Cys Thr Cys Ile Pro Ile Pro Ser Ser Trp Ala
305                 310                 315                 320

Phe Gly Lys Phe Leu Trp Glu Trp Ala Ser Ala Arg Phe Ser Trp Leu
                325                 330                 335

Ser Leu Leu Val Pro Phe Val Gln Trp Phe Val Gly Leu Ser Pro Thr
            340                 345                 350

Val Trp Leu Ser Val Ile Trp Met Met Trp Tyr Trp Gly Pro Ser Leu
        355                 360                 365

Tyr Ser Ile Leu Ser Pro Phe Leu Pro Leu Leu Pro Ile Phe Phe Cys
    370                 375                 380

Leu Trp Val Tyr Ile
385
```

<210> SEQ ID NO 35
<211> LENGTH: 389
<212> TYPE: PRT
<213> ORGANISM: Hepatitis B virus

<400> SEQUENCE: 35

```
Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly
        35                  40                  45

Ala Gly Ala Phe Gly Leu Gly Phe Thr Pro Pro His Gly Gly Leu Leu
    50                  55                  60

Gly Trp Ser Pro Gln Ala Gln Gly Ile Ile Gln Thr Leu Pro Ala Asn
65                  70                  75                  80

Pro Pro Pro Ala Ser Thr Asn Arg Gln Ser Gly Arg Gln Pro Thr Pro
                85                  90                  95

Leu Ser Pro Pro Leu Arg Asn Thr His Pro Gln Ala Met Gln Trp Asn
            100                 105                 110

Ser Thr Thr Phe His Gln Thr Leu Gln Asp Pro Arg Val Arg Gly Leu
        115                 120                 125

Tyr Phe Pro Ala Gly Gly Ser Ser Gly Thr Val Asn Pro Val Pro
    130                 135                 140

Thr Thr Ala Ser Pro Ile Ser Ser Ile Phe Ser Arg Ile Gly Asp Pro
145                 150                 155                 160

Ala Leu Asn Met Glu Lys Ile Thr Ser Gly Phe Leu Gly Pro Leu Leu
                165                 170                 175

Val Leu Gln Ala Gly Phe Phe Leu Leu Thr Arg Ile Leu Thr Ile Pro
            180                 185                 190

Gln Ser Leu Asp Ser Trp Trp Thr Ser Leu Asn Phe Leu Gly Gly Thr
        195                 200                 205

Thr Val Cys Leu Gly Gln Asn Ser Gln Ser Pro Thr Ser Asn His Ser
    210                 215                 220

Pro Thr Ser Cys Pro Pro Thr Cys Pro Gly Tyr Arg Trp Met Cys Leu
225                 230                 235                 240

Arg Arg Phe Ile Ile Phe Leu Phe Ile Leu Leu Leu Cys Leu Ile Phe
                245                 250                 255

Leu Leu Val Leu Leu Asp Tyr Gln Gly Met Leu Pro Val Cys Pro Leu
            260                 265                 270

Ile Pro Gly Ser Ser Thr Thr Arg Val Gly Pro Cys Lys Thr Cys Thr
        275                 280                 285

Thr Thr Val Gln Gly Thr Ser Met Tyr Pro Tyr Cys Cys Cys Thr Lys
    290                 295                 300

Pro Ser Asp Gly Asn Cys Thr Cys Ile Pro Ile Pro Ser Ser Trp Ala
305                 310                 315                 320

Phe Gly Lys Phe Leu Trp Val Trp Ala Ser Ala Arg Phe Ser Trp Leu
                325                 330                 335

Ser Leu Leu Val Pro Phe Val Gln Trp Phe Val Gly Leu Ser Pro Thr
            340                 345                 350

Val Trp Leu Ser Val Ile Trp Met Met Trp Tyr Trp Gly Pro Ser Leu
        355                 360                 365

Tyr Ser Ile Leu Ser Pro Phe Leu Pro Leu Leu Pro Ile Phe Phe Cys
```

Leu Trp Val Tyr Ile
385

<210> SEQ ID NO 36
<211> LENGTH: 389
<212> TYPE: PRT
<213> ORGANISM: Hepatitis B virus

<400> SEQUENCE: 36

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly
        35                  40                  45

Ala Gly Ala Phe Gly Leu Gly Phe Thr Pro Pro His Gly Gly Leu Leu
    50                  55                  60

Gly Trp Ser Pro Gln Ala Gln Gly Ile Leu Gln Thr Leu Pro Ala Asn
65                  70                  75                  80

Pro Pro Pro Ala Ser Thr Asn Arg Gln Ser Gly Arg Gln Pro Thr Pro
                85                  90                  95

Leu Ser Pro Pro Leu Arg Asn Thr His Pro Gln Ala Met Gln Trp Asn
            100                 105                 110

Ser Thr Thr Phe His Gln Thr Leu Gln Asp Pro Arg Val Arg Gly Leu
        115                 120                 125

Tyr Phe Pro Ala Gly Gly Ser Ser Gly Thr Val Asn Pro Val Leu
    130                 135                 140

Thr Thr Ala Ser Pro Leu Ser Ser Ile Ser Ala Arg Thr Gly Asp Pro
145                 150                 155                 160

Val Thr Ile Met Glu Asn Ile Thr Ser Gly Phe Leu Gly Pro Leu Leu
                165                 170                 175

Val Leu Glu Ala Gly Phe Phe Leu Leu Thr Arg Ile Leu Thr Ile Pro
            180                 185                 190

Gln Ser Leu Asp Ser Trp Trp Thr Ser Leu Asn Phe Leu Gly Gly Thr
        195                 200                 205

Thr Val Cys Leu Gly Gln Asn Ser Gln Ser Pro Thr Ser His His Ser
    210                 215                 220

Pro Thr Ser Cys Pro Pro Ile Cys Pro Gly Tyr Arg Trp Met Cys Leu
225                 230                 235                 240

Arg Arg Phe Ile Ile Phe Leu Phe Ile Leu Leu Cys Leu Ile Phe
                245                 250                 255

Leu Leu Val Leu Leu Asp Tyr Gln Gly Met Leu Pro Val Cys Pro Leu
            260                 265                 270

Ile Pro Gly Thr Ser Thr Thr Ser Thr Gly Pro Cys Arg Thr Cys Thr
        275                 280                 285

Thr Pro Ala Gln Gly Thr Ser Met Tyr Pro Ser Cys Cys Cys Thr Lys
    290                 295                 300

Pro Ser Asp Gly Asn Cys Thr Cys Ile Pro Ile Pro Ser Ser Trp Ala
305                 310                 315                 320

Phe Gly Lys Phe Leu Trp Gln Trp Ala Ser Ala Arg Phe Ser Trp Leu
                325                 330                 335

Ser Leu Leu Val Pro Phe Val Gln Trp Phe Val Gly Leu Ser Pro Thr
            340                 345                 350

```
Val Trp Val Ser Ala Ile Trp Met Met Trp Tyr Trp Gly Pro Ser Leu
            355                 360                 365

Tyr Ser Ile Val Ser Pro Phe Ile Pro Leu Leu Pro Ile Phe Phe Cys
        370                 375                 380

Leu Trp Val Tyr Ile
385

<210> SEQ ID NO 37
<211> LENGTH: 389
<212> TYPE: PRT
<213> ORGANISM: Hepatitis B virus

<400> SEQUENCE: 37

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly
        35                  40                  45

Ala Gly Ala Phe Gly Leu Gly Phe Thr Pro Pro His Gly Gly Leu Leu
    50                  55                  60

Gly Trp Ser Pro Gln Ala Gln Gly Ile Leu Gln Thr Leu Pro Ala Asn
65                  70                  75                  80

Pro Pro Pro Ala Ser Thr Asn Arg Gln Thr Gly Arg Gln Pro Thr Pro
                85                  90                  95

Leu Ser Pro Pro Leu Arg Asn Thr His Pro Gln Ala Met Gln Trp Asn
            100                 105                 110

Ser Thr Thr Phe His Gln Thr Leu Gln Asp Pro Arg Val Arg Gly Leu
        115                 120                 125

Tyr Phe Pro Ala Gly Gly Ser Ser Gly Ala Val Asn Pro Val Pro
    130                 135                 140

Thr Thr Ala Ser Pro Leu Ser Ser Ile Phe Ser Arg Ile Gly Asp Pro
145                 150                 155                 160

Ala Leu Asn Met Glu Asn Ile Thr Ser Gly Phe Leu Gly Pro Leu Leu
                165                 170                 175

Val Leu Gln Ala Gly Phe Phe Leu Leu Thr Arg Ile Leu Thr Ile Pro
            180                 185                 190

Gln Ser Leu Asp Ser Trp Trp Thr Ser Leu Asn Phe Leu Gly Gly Thr
        195                 200                 205

Thr Val Cys Leu Gly Gln Asn Ser Gln Ser Pro Thr Ser Asn His Ser
    210                 215                 220

Pro Thr Ser Cys Pro Pro Thr Cys Pro Gly Tyr Arg Trp Met Cys Leu
225                 230                 235                 240

Arg Arg Phe Ile Ile Phe Leu Phe Ile Leu Leu Leu Cys Leu Ile Phe
                245                 250                 255

Leu Leu Val Leu Leu Asp Tyr Gln Gly Met Leu Pro Val Cys Pro Leu
            260                 265                 270

Ile Pro Gly Ser Ser Thr Thr Ser Thr Gly Pro Cys Arg Thr Cys Met
        275                 280                 285

Thr Thr Ala Gln Gly Thr Ser Met Tyr Pro Ser Cys Cys Cys Thr Lys
    290                 295                 300

Pro Ser Asp Gly Asn Cys Thr Cys Ile Pro Ile Pro Ser Ser Trp Ala
305                 310                 315                 320

Phe Gly Lys Phe Leu Trp Glu Trp Ala Ser Ala Arg Phe Ser Trp Leu
                325                 330                 335
```

```
Ser Leu Leu Val Pro Phe Val Gln Trp Phe Val Gly Leu Ser Pro Thr
                340                 345                 350

Val Trp Leu Ser Val Ile Trp Met Met Trp Tyr Trp Gly Pro Ser Leu
            355                 360                 365

Tyr Ser Ile Leu Ser Pro Phe Leu Pro Leu Leu Pro Ile Phe Phe Cys
        370                 375                 380

Leu Trp Val Tyr Ile
385

<210> SEQ ID NO 38
<211> LENGTH: 389
<212> TYPE: PRT
<213> ORGANISM: Hepatitis B virus

<400> SEQUENCE: 38

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly
        35                  40                  45

Ala Gly Ala Phe Gly Leu Gly Phe Thr Pro Pro His Gly Gly Leu Leu
    50                  55                  60

Gly Trp Ser Pro Gln Ala Gln Gly Ile Leu Gln Thr Leu Pro Ala Asn
65                  70                  75                  80

Pro Pro Pro Ala Ser Thr Asn Arg Gln Thr Gly Arg Gln Pro Thr Pro
                85                  90                  95

Leu Ser Pro Pro Leu Arg Asn Thr His Pro Gln Ala Met Gln Trp Asn
            100                 105                 110

Ser Thr Thr Phe His Gln Thr Leu Gln Asp Pro Arg Val Arg Gly Leu
        115                 120                 125

Tyr Phe Pro Ala Gly Gly Ser Ser Ser Gly Ala Val Asn Pro Val Pro
    130                 135                 140

Thr Thr Ala Ser Pro Leu Ser Ser Ile Phe Ser Arg Ile Gly Asp Pro
145                 150                 155                 160

Ala Leu Asn Met Glu Asn Ile Thr Ser Gly Phe Leu Gly Pro Leu Leu
                165                 170                 175

Val Leu Gln Ala Gly Phe Phe Leu Leu Thr Arg Ile Leu Thr Ile Pro
            180                 185                 190

Gln Ser Leu Asp Ser Trp Trp Thr Ser Leu Asn Phe Leu Gly Gly Thr
        195                 200                 205

Thr Val Cys Leu Gly Gln Asn Ser Gln Ser Pro Thr Ser Asn His Ser
    210                 215                 220

Pro Thr Ser Cys Pro Pro Thr Cys Pro Gly Tyr Arg Trp Met Cys Leu
225                 230                 235                 240

Arg Arg Phe Ile Ile Phe Leu Phe Ile Leu Leu Leu Cys Leu Ile Phe
                245                 250                 255

Leu Leu Val Leu Leu Asp Tyr Gln Gly Met Leu Pro Val Cys Pro Leu
            260                 265                 270

Ile Pro Gly Ser Ser Thr Thr Ser Thr Gly Pro Cys Arg Thr Cys Thr
        275                 280                 285

Thr Pro Ala Gln Gly Thr Ser Met Tyr Pro Ser Cys Cys Cys Thr Lys
    290                 295                 300

Pro Ser Asp Gly Asn Cys Thr Cys Ile Pro Ile Pro Ser Ser Trp Ala
```

```
                305                 310                 315                 320
Phe Gly Lys Phe Leu Trp Glu Trp Ala Ser Ala Arg Phe Ser Trp Leu
                325                 330                 335

Ser Leu Leu Val Pro Phe Val Gln Trp Phe Val Gly Leu Ser Pro Thr
                340                 345                 350

Val Trp Leu Ser Val Ile Trp Met Met Trp Tyr Trp Gly Pro Ser Leu
                355                 360                 365

Tyr Ser Ile Leu Ser Pro Phe Leu Pro Leu Leu Pro Ile Phe Phe Cys
                370                 375                 380

Leu Trp Val Tyr Ile
385

<210> SEQ ID NO 39
<211> LENGTH: 399
<212> TYPE: PRT
<213> ORGANISM: Hepatitis B virus

<400> SEQUENCE: 39

Met Gly Leu Ser Trp Thr Val Pro Leu Glu Trp Gly Lys Asn His Ser
1               5                   10                  15

Thr Thr Asn Pro Leu Gly Phe Phe Pro Asp His Gln Leu Asp Pro Ala
                20                  25                  30

Phe Arg Ala Asn Thr Lys Asn Pro Asp Trp Asp Asn Asn Pro Asn Lys
            35                  40                  45

Asp His Trp Thr Glu Ala Asn Lys Val Gly Val Gly Ala Phe Gly Pro
        50                  55                  60

Gly Phe Thr Pro Pro His Gly Gly Leu Leu Gly Trp Ser Pro Gln Ala
65                  70                  75                  80

Gln Gly Met Leu Lys Thr Leu Pro Ala Asp Pro Pro Ala Ser Thr
                85                  90                  95

Asn Arg Gln Ser Gly Arg Gln Pro Thr Pro Ile Thr Pro Pro Leu Arg
                100                 105                 110

Asp Thr His Pro Gln Ala Met Gln Trp Asn Ser Thr Thr Phe His Gln
            115                 120                 125

Ala Leu Gln Asp Pro Arg Val Lys Asn Leu Tyr Phe Pro Ala Gly Gly
        130                 135                 140

Ser Ser Ser Gly Thr Val Asn Pro Val Pro Thr Thr Ala Ser Leu Ile
145                 150                 155                 160

Ser Ser Ile Phe Ser Arg Ile Gly Asp Pro Ala Pro Asn Met Glu Ser
                165                 170                 175

Ile Thr Ser Gly Phe Leu Gly Pro Leu Leu Gly Leu Gln Ala Gly Phe
                180                 185                 190

Phe Leu Leu Thr Lys Ile Leu Thr Ile Pro Gln Ser Leu Asp Ser Trp
            195                 200                 205

Trp Thr Ser Leu Asn Phe Leu Gly Gly Ala Pro Val Cys Leu Gly Gln
        210                 215                 220

Asn Ser Gln Ser Gln Ile Ser Asn His Ser Pro Thr Ser Cys Pro Pro
225                 230                 235                 240

Ile Cys Pro Gly Tyr Arg Trp Met Cys Leu Arg Arg Phe Ile Ile Phe
                245                 250                 255

Leu Phe Ile Leu Leu Leu Cys Leu Ile Phe Leu Leu Val Leu Leu Asp
                260                 265                 270

Tyr Gln Gly Met Leu Pro Val Cys Pro Leu Ile Pro Gly Ser Ser Thr
            275                 280                 285
```

-continued

```
Thr Ser Thr Gly Pro Cys Arg Thr Cys Thr Thr Leu Ala Gln Gly Thr
    290                 295                 300

Ser Met Phe Pro Ser Cys Cys Cys Leu Lys Pro Ser Asp Gly Asn Cys
305                 310                 315                 320

Thr Cys Ile Pro Ile Pro Ser Ser Trp Ala Phe Ala Lys Phe Leu Trp
                325                 330                 335

Glu Trp Ala Ser Ala Arg Phe Ser Trp Leu Ser Leu Leu Val Pro Phe
                340                 345                 350

Val Gln Trp Phe Ala Gly Leu Ser Pro Thr Val Trp Leu Ser Val Ile
                355                 360                 365

Trp Met Met Trp Tyr Trp Gly Pro Asn Leu Tyr Asn Ile Leu Lys Pro
    370                 375                 380

Phe Ile Pro Leu Leu Leu Ile Ser Phe Cys Leu Trp Val Tyr Ile
385                 390                 395

<210> SEQ ID NO 40
<211> LENGTH: 399
<212> TYPE: PRT
<213> ORGANISM: Hepatitis B virus

<400> SEQUENCE: 40

Met Gly Leu Ser Trp Thr Val Pro Leu Glu Trp Gly Lys Asn His Ser
1               5                   10                  15

Thr Thr Asn Pro Leu Gly Phe Phe Pro Asp His Gln Leu Asp Pro Ala
                20                  25                  30

Phe Arg Ala Asn Thr Arg Asn Pro Asp Trp Asp His Asn Pro Asn Lys
                35                  40                  45

Asp His Trp Thr Glu Ala Asn Lys Val Gly Val Gly Ala Phe Gly Pro
    50                  55                  60

Gly Phe Thr Pro Pro His Gly Gly Leu Leu Gly Trp Ser Pro Gln Ala
65                  70                  75                  80

Gln Gly Met Leu Lys Thr Leu Pro Ala Asp Pro Pro Pro Ala Ser Thr
                85                  90                  95

Asn Arg Gln Ser Gly Arg Gln Pro Thr Pro Ile Thr Pro Pro Leu Arg
                100                 105                 110

Asp Thr His Pro Gln Ala Met Gln Trp Asn Ser Thr Ala Phe His Gln
            115                 120                 125

Ala Leu Gln Asp Pro Lys Val Arg Gly Leu Tyr Phe Pro Ala Gly Gly
            130                 135                 140

Ser Ser Ser Gly Thr Val Ser Pro Val Pro Thr Thr Ala Ser Leu Ile
145                 150                 155                 160

Ser Ser Ile Phe Ser Arg Ile Gly Asp Pro Ala Pro Asn Met Glu Ser
                165                 170                 175

Ile Thr Ser Gly Phe Leu Gly Pro Leu Leu Val Leu Gln Ala Gly Phe
                180                 185                 190

Phe Leu Leu Thr Lys Ile Leu Thr Ile Pro Gln Ser Leu Asp Ser Trp
                195                 200                 205

Trp Thr Ser Leu Asn Phe Leu Gly Gly Ala Pro Val Cys Leu Gly Gln
    210                 215                 220

Asn Ser Gln Ser Pro Thr Ser Asn His Ser Pro Thr Ser Cys Pro Pro
225                 230                 235                 240

Ile Cys Pro Gly Tyr Arg Trp Met Cys Leu Arg Arg Phe Ile Ile Phe
                245                 250                 255

Leu Phe Ile Leu Leu Leu Cys Leu Ile Phe Leu Leu Val Leu Leu Asp
                260                 265                 270
```

```
Tyr Gln Gly Met Leu Pro Val Cys Pro Leu Ile Pro Gly Ser Ser Thr
            275                 280                 285

Thr Ser Thr Gly Pro Cys Arg Thr Cys Thr Thr Leu Ala Gln Gly Thr
290                 295                 300

Ser Met Phe Pro Ser Cys Cys Cys Ser Lys Pro Ser Asp Gly Asn Cys
305                 310                 315                 320

Thr Cys Ile Pro Ile Pro Ser Ser Trp Ala Phe Gly Lys Phe Leu Trp
                325                 330                 335

Glu Trp Ala Ser Ala Arg Phe Ser Trp Leu Ser Leu Leu Val Pro Phe
            340                 345                 350

Val Gln Trp Phe Ala Gly Leu Ser Pro Thr Val Trp Leu Ser Val Ile
            355                 360                 365

Trp Met Met Trp Tyr Trp Gly Pro Ser Leu Tyr Asn Ile Leu Ser Pro
370                 375                 380

Phe Ile Pro Leu Leu Pro Ile Phe Phe Cys Leu Trp Val Tyr Ile
385                 390                 395
```

<210> SEQ ID NO 41
<211> LENGTH: 399
<212> TYPE: PRT
<213> ORGANISM: Hepatitis B virus

<400> SEQUENCE: 41

```
Met Gly Leu Ser Trp Thr Val Pro Leu Glu Trp Gly Lys Asn Ile Ser
1               5                   10                  15

Thr Thr Asn Pro Leu Gly Phe Phe Pro Asp His Gln Leu Asp Pro Ala
            20                  25                  30

Phe Arg Ala Asn Thr Arg Asn Pro Asp Trp Asp His Asn Pro Asn Lys
        35                  40                  45

Asp His Trp Thr Glu Ala Asn Lys Val Gly Val Gly Ala Phe Gly Pro
    50                  55                  60

Gly Phe Thr Pro Pro His Gly Gly Leu Leu Gly Trp Ser Pro Gln Ala
65                  70                  75                  80

Gln Gly Met Leu Lys Thr Leu Pro Ala Asp Pro Pro Ala Ser Thr
                85                  90                  95

Asn Arg Gln Ser Gly Arg Gln Pro Thr Pro Ile Thr Pro Pro Leu Arg
            100                 105                 110

Asp Thr His Pro Gln Ala Met Gln Trp Asn Ser Thr Thr Phe His Gln
        115                 120                 125

Ala Leu Gln Asp Pro Arg Val Arg Gly Leu Tyr Phe Pro Ala Gly Gly
    130                 135                 140

Ser Ser Ser Gly Thr Val Asn Pro Val Pro Thr Thr Ala Ser Leu Ile
145                 150                 155                 160

Ser Ser Ile Phe Ser Arg Ile Gly Asp Pro Ala Pro Asn Met Glu Ser
                165                 170                 175

Ile Thr Ser Gly Phe Leu Gly Pro Leu Leu Val Leu Gln Ala Gly Phe
            180                 185                 190

Phe Leu Leu Thr Lys Ile Leu Thr Ile Pro Gln Ser Leu Asp Ser Trp
        195                 200                 205

Trp Thr Ser Leu Asn Phe Leu Gly Gly Ala Pro Val Cys Leu Gly Gln
    210                 215                 220

Asn Ser Gln Ser Pro Thr Ser Ser His Ser Pro Thr Ser Cys Pro Pro
225                 230                 235                 240

Ile Cys Pro Gly Tyr Arg Trp Met Cys Leu Arg Arg Phe Ile Ile Phe
```

```
                        245                 250                 255
Leu Phe Ile Leu Leu Leu Cys Leu Ile Phe Leu Leu Val Leu Leu Asp
                    260                 265                 270

Tyr Gln Gly Met Leu Pro Val Cys Pro Leu Ile Pro Gly Ser Ser Thr
                275                 280                 285

Thr Ser Thr Gly Pro Cys Arg Thr Cys Thr Thr Leu Ala Gln Gly Thr
            290                 295                 300

Ser Met Phe Pro Ser Cys Cys Ser Lys Pro Ser Asp Gly Asn Cys
305                 310                 315                 320

Thr Cys Ile Pro Ile Pro Ser Ser Trp Ala Phe Gly Lys Phe Leu Trp
                325                 330                 335

Glu Trp Ala Ser Ala Arg Phe Ser Trp Leu Ser Leu Leu Val Pro Phe
                340                 345                 350

Val Gln Trp Phe Ala Gly Leu Ser Pro Thr Val Trp Leu Ser Val Ile
                355                 360                 365

Trp Met Met Trp Tyr Trp Gly Pro Ser Leu Tyr Asn Ile Leu Ser Pro
            370                 375                 380

Phe Ile Pro Leu Leu Pro Ile Phe Phe Cys Leu Trp Val Tyr Ile
385                 390                 395
```

<210> SEQ ID NO 42
<211> LENGTH: 399
<212> TYPE: PRT
<213> ORGANISM: Hepatitis B virus

<400> SEQUENCE: 42

```
Met Gly Leu Ser Trp Thr Val Pro Leu Glu Trp Gly Lys Asn His Ser
1               5                   10                  15

Thr Thr Asn Pro Leu Gly Phe Phe Pro Asp His Gln Leu Asp Pro Ala
                20                  25                  30

Phe Arg Ala Asn Thr Arg Asn Pro Asp Trp Asp His Asn Pro Asn Lys
            35                  40                  45

Asp His Trp Thr Glu Ala Asn Lys Val Gly Val Gly Ala Phe Gly Pro
        50                  55                  60

Gly Phe Thr Pro Pro His Gly Gly Leu Leu Gly Trp Ser Pro Gln Ala
65                  70                  75                  80

Gln Gly Met Leu Lys Thr Leu Pro Ala Asp Pro Pro Ala Ser Thr
                85                  90                  95

Asn Arg Gln Ser Gly Arg Gln Pro Thr Pro Ile Thr Pro Pro Leu Arg
            100                 105                 110

Asp Thr His Pro Gln Ala Met Gln Trp Asn Ser Thr Thr Phe His Gln
        115                 120                 125

Ala Leu Gln Asp Pro Arg Val Arg Gly Leu Tyr Phe Pro Ala Gly Gly
    130                 135                 140

Ser Ser Ser Gly Thr Val Asn Pro Val Pro Thr Thr Val Ser Leu Ile
145                 150                 155                 160

Ser Ser Ile Phe Ser Arg Thr Gly Asp Pro Ala Pro Asn Met Glu Gly
                165                 170                 175

Ile Thr Ser Gly Phe Leu Gly Pro Leu Leu Val Leu Gln Ala Gly Phe
            180                 185                 190

Phe Leu Leu Thr Lys Ile Leu Thr Ile Pro Gln Ser Leu Asp Ser Trp
        195                 200                 205

Trp Thr Ser Leu Asn Phe Leu Gly Gly Ala Pro Val Cys Leu Gly Gln
    210                 215                 220
```

```
Asn Ser Gln Ser Pro Thr Ser Asn His Ser Pro Thr Ser Cys Pro Pro
225                 230                 235                 240

Ile Cys Pro Gly Tyr Arg Trp Met Cys Leu Arg Arg Phe Ile Ile Phe
                245                 250                 255

Leu Phe Ile Leu Leu Leu Cys Leu Ile Phe Leu Leu Val Leu Leu Gly
            260                 265                 270

Tyr Gln Gly Met Leu Pro Val Cys Pro Leu Ile Pro Gly Ser Ser Thr
        275                 280                 285

Thr Ile Thr Gly Pro Cys Arg Thr Cys Thr Thr Leu Ala Gln Gly Thr
    290                 295                 300

Ser Met Phe Pro Ser Cys Cys Cys Ser Lys Pro Ser Asp Gly Asn Cys
305                 310                 315                 320

Thr Cys Ile Pro Ile Pro Ser Ser Trp Ala Phe Gly Lys Phe Leu Trp
                325                 330                 335

Glu Trp Ala Ser Ala Arg Phe Ser Trp Leu Ser Leu Leu Val Pro Phe
            340                 345                 350

Val Gln Trp Phe Ala Gly Leu Ser Pro Thr Val Trp Leu Ser Val Ile
        355                 360                 365

Trp Met Met Trp Tyr Trp Gly Pro Ser Leu Tyr Asn Ile Leu Ser Pro
    370                 375                 380

Phe Ile Pro Leu Leu Pro Ile Phe Phe Cys Leu Trp Val Tyr Ile
385                 390                 395

<210> SEQ ID NO 43
<211> LENGTH: 400
<212> TYPE: PRT
<213> ORGANISM: Hepatitis B virus

<400> SEQUENCE: 43

Met Gly Ala Pro Leu Ser Thr Thr Arg Arg Gly Met Gly Gln Asn Leu
1               5                   10                  15

Ser Val Pro Asn Pro Leu Gly Phe Leu Pro Asp His Gln Leu Asp Pro
                20                  25                  30

Leu Phe Arg Ala Asn Ser Ser Ser Pro Asp Trp Asp Phe Asn Thr Asn
            35                  40                  45

Lys Asp Ser Trp Pro Met Ala Asn Lys Val Gly Val Gly Gly Tyr Gly
        50                  55                  60

Pro Gly Phe Thr Pro Pro His Gly Gly Leu Leu Gly Trp Ser Pro Gln
65                  70                  75                  80

Ala Gln Gly Val Leu Thr Thr Leu Pro Ala Asp Pro Pro Pro Ala Ser
                85                  90                  95

Thr Asn Arg Leu Ser Gly Arg Lys Pro Thr Gln Val Ser Pro Pro Leu
            100                 105                 110

Arg Asp Thr His Pro Gln Ala Met Gln Trp Asn Ser Thr His Phe His
        115                 120                 125

Gln Ala Leu Leu Asp Pro Arg Val Arg Ala Leu Tyr Phe Pro Ala Gly
    130                 135                 140

Gly Ser Ser Ser Gly Thr Gln Asn Pro Ala Pro Thr Ile Ala Ser Leu
145                 150                 155                 160

Thr Ser Ser Ile Ser Ser Lys Thr Gly Gly Pro Ala Met Asn Met Glu
                165                 170                 175

Asn Ile Thr Ser Gly Leu Leu Gly Pro Leu Arg Val Leu Gln Ala Val
            180                 185                 190

Cys Phe Leu Leu Thr Lys Ile Leu Thr Ile Pro Gln Ser Leu Asp Ser
        195                 200                 205
```

```
Trp Trp Thr Ser Leu Asn Phe Leu Gly Gly Leu Pro Arg Cys Pro Gly
210                 215                 220
Gln Asn Ser Gln Ser Pro Thr Ser Asn His Leu Pro Thr Ser Cys Pro
225                 230                 235                 240
Pro Thr Cys Pro Gly Tyr Arg Trp Met Cys Leu Arg Arg Phe Ile Ile
                245                 250                 255
Phe Leu Phe Ile Leu Leu Leu Cys Leu Ile Phe Leu Leu Val Leu Leu
                260                 265                 270
Asp Tyr Gln Gly Met Leu Pro Val Cys Pro Leu Leu Pro Gly Ser Thr
            275                 280                 285
Thr Thr Ser Thr Gly Pro Cys Lys Thr Cys Thr Ala Leu Ala Gln Gly
290                 295                 300
Thr Ser Met Phe Pro Ser Cys Cys Cys Ser Lys Pro Ser Asp Gly Asn
305                 310                 315                 320
Cys Thr Cys Ile Pro Ile Pro Ser Ser Trp Ala Leu Gly Lys Tyr Leu
                325                 330                 335
Trp Glu Trp Ala Ser Ala Arg Phe Ser Trp Leu Ser Leu Leu Val Gln
                340                 345                 350
Phe Val Gln Trp Cys Val Gly Leu Ser Pro Thr Val Trp Leu Leu Val
                355                 360                 365
Ile Trp Met Ile Trp Tyr Trp Gly Pro Asn Leu Cys Ser Ile Leu Ser
370                 375                 380
Pro Phe Ile Pro Leu Leu Pro Ile Phe Cys Tyr Leu Trp Val Ser Ile
385                 390                 395                 400

<210> SEQ ID NO 44
<211> LENGTH: 400
<212> TYPE: PRT
<213> ORGANISM: Hepatitis B virus

<400> SEQUENCE: 44

Met Gly Ala Pro Leu Ser Thr Thr Arg Arg Gly Met Gly Gln Asn Leu
1               5                   10                  15
Ser Val Pro Asn Pro Leu Gly Phe Phe Pro Asp His Gln Leu Asp Pro
                20                  25                  30
Leu Phe Arg Ala Asn Ser Ser Ser Pro Asp Trp Asp Phe Asn Lys Asn
            35                  40                  45
Lys Asp Thr Trp Pro Met Ala Asn Lys Val Gly Val Gly Gly Tyr Gly
        50                  55                  60
Pro Gly Phe Thr Pro Pro His Gly Gly Leu Leu Gly Trp Ser Pro Gln
65                  70                  75                  80
Ala Gln Gly Val Leu Thr Thr Leu Pro Ala Asp Pro Pro Pro Ala Ser
                85                  90                  95
Thr Asn Arg Leu Ser Gly Arg Lys Pro Thr Pro Val Ser Pro Pro Leu
                100                 105                 110
Arg Asp Thr His Pro Gln Ala Met Gln Trp Asn Ser Thr His Phe His
            115                 120                 125
Gln Ala Leu Leu Asp Pro Arg Val Arg Ala Leu Tyr Phe Pro Ala Gly
        130                 135                 140
Gly Ser Ser Ser Gly Thr Gln Asn Pro Ala Pro Thr Ile Ala Ser Leu
145                 150                 155                 160
Thr Ser Ser Ile Ser Ser Lys Thr Gly Gly Pro Ala Met Asn Met Asp
                165                 170                 175
Asn Ile Thr Ser Gly Leu Leu Gly Pro Leu Leu Val Leu Gln Ala Val
```

```
                180                 185                 190
Cys Phe Leu Leu Thr Lys Ile Leu Thr Ile Pro Gln Ser Leu Asp Ser
            195                 200                 205

Trp Trp Thr Ser Leu Asn Phe Leu Gly Gly Leu Pro Gly Cys Pro Gly
        210                 215                 220

Gln Asn Ser Gln Ser Pro Thr Ser Asn His Leu Pro Thr Ser Cys Pro
225                 230                 235                 240

Pro Thr Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Thr
        275                 280                 285

Thr Thr Ser Thr Gly Pro Cys Lys Thr Cys Thr Thr Leu Ala Gln Gly
        290                 295                 300

Thr Ser Met Phe Pro Ser Cys Cys Cys Ser Lys Pro Ser Asp Gly Asn
305                 310                 315                 320

Cys Thr Cys Ile Pro Ile Pro Ser Ser Trp Ala Leu Gly Lys Tyr Leu
                325                 330                 335

Trp Glu Trp Ala Ser Ala Arg Phe Ser Trp Leu Ser Leu Leu Val Gln
            340                 345                 350

Phe Val Gln Trp Cys Val Gly Leu Ser Pro Thr Val Trp Leu Leu Val
        355                 360                 365

Ile Trp Met Ile Trp Tyr Trp Glu Pro Asn Leu Cys Ser Ile Leu Ser
        370                 375                 380

Pro Phe Ile Pro Leu Leu Pro Ile Phe Cys Tyr Leu Trp Val Ser Ile
385                 390                 395                 400

<210> SEQ ID NO 45
<211> LENGTH: 400
<212> TYPE: PRT
<213> ORGANISM: Hepatitis B virus

<400> SEQUENCE: 45

Met Gly Ala Pro Leu Ser Thr Thr Arg Arg Gly Met Gly Leu Asn Leu
1               5                   10                  15

Ser Val Pro Asn Pro Leu Gly Phe Leu Pro Asp His Gln Leu Asp Pro
            20                  25                  30

Leu Phe Arg Ala Asn Ser Ser Ser Pro Asp Trp Asp Phe Asn Thr Asn
        35                  40                  45

Lys Asp Ser Trp Pro Met Ala Asn Lys Val Gly Val Gly Gly Tyr Gly
    50                  55                  60

Pro Gly Phe Thr Pro Pro His Gly Gly Leu Leu Gly Trp Ser Pro Gln
65                  70                  75                  80

Ala Gln Gly Val Leu Thr Thr Leu Pro Ala Asp Pro Pro Pro Ala Ser
                85                  90                  95

Thr Asn Arg Arg Ser Gly Arg Lys Pro Thr Pro Val Ser Pro Pro Leu
            100                 105                 110

Arg Asp Thr His Pro Gln Ala Met Gln Trp Asn Ser Thr Gln Phe His
        115                 120                 125

Gln Ala Leu Leu Asp Pro Arg Val Arg Ala Leu Tyr Phe Pro Ala Gly
    130                 135                 140

Gly Ser Ser Ser Gly Thr Gln Asn Pro Val Pro Thr Ile Ala Ser Leu
145                 150                 155                 160
```

-continued

```
Thr Ser Ser Ile Phe Ser Lys Thr Gly Gly Pro Ala Met Asn Met Glu
                165                 170                 175

Asn Ile Thr Ser Gly Leu Leu Gly Pro Leu Leu Val Leu Gln Ala Val
            180                 185                 190

Cys Phe Leu Leu Thr Lys Ile Leu Thr Ile Pro Gln Ser Leu Asp Ser
        195                 200                 205

Trp Trp Thr Ser Leu Asn Phe Leu Gly Gly Leu Pro Gly Cys Pro Gly
    210                 215                 220

Gln Asn Ser Gln Ser Pro Thr Ser Asn His Leu Pro Thr Ser Cys Pro
225                 230                 235                 240

Pro Thr Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Leu Pro Gly Ser Thr
        275                 280                 285

Thr Thr Ser Thr Gly Pro Cys Lys Thr Cys Thr Thr Leu Ala Gln Gly
    290                 295                 300

Thr Ser Met Phe Pro Ser Cys Cys Cys Ser Lys Pro Ser Asp Gly Asn
305                 310                 315                 320

Cys Thr Cys Ile Pro Ile Pro Ser Ser Trp Ala Leu Gly Lys Tyr Leu
                325                 330                 335

Trp Glu Trp Ala Ser Ala Arg Phe Ser Trp Leu Ser Leu Leu Val Gln
            340                 345                 350

Phe Val Gln Trp Cys Val Gly Leu Ser Pro Thr Val Trp Leu Leu Val
        355                 360                 365

Ile Trp Met Ile Trp Tyr Trp Gly Pro Asn Leu Cys Ser Ile Leu Ser
    370                 375                 380

Pro Phe Ile Pro Leu Leu Pro Ile Phe Cys Tyr Leu Trp Val Ser Ile
385                 390                 395                 400
```

<210> SEQ ID NO 46
<211> LENGTH: 400
<212> TYPE: PRT
<213> ORGANISM: Hepatitis B virus

<400> SEQUENCE: 46

```
Met Gly Ala Pro Leu Ser Thr Thr Arg Arg Gly Met Gly Gln Asn Leu
1               5                   10                  15

Ser Val Pro Asn Pro Leu Gly Phe Phe Pro Asp His Gln Leu Asp Pro
            20                  25                  30

Leu Phe Arg Ala Asn Ser Ser Ser Pro Asp Trp Asp Phe Asn Lys Asn
        35                  40                  45

Lys Asp Asn Trp Pro Met Ala Asn Lys Val Gly Val Gly Gly Tyr Gly
    50                  55                  60

Pro Gly Phe Thr Pro Pro His Gly Gly Leu Leu Gly Trp Ser Pro Gln
65                  70                  75                  80

Ala Gln Gly Val Leu Thr Thr Leu Pro Ala Asp Pro Pro Ala Ser
                85                  90                  95

Thr Asn Arg Arg Ser Gly Arg Lys Pro Thr Pro Val Ser Pro Pro Leu
            100                 105                 110

Arg Asp Thr His Pro Gln Ala Met Gln Trp Asn Ser Thr Gln Phe His
        115                 120                 125

Gln Ala Leu Leu Asp Pro Arg Val Arg Ala Leu Tyr Phe Pro Ala Gly
    130                 135                 140
```

Gly Ser Ser Ser Glu Thr Gln Asn Pro Ala Pro Thr Ile Ala Ser Leu
145                 150                 155                 160

Thr Ser Ser Ile Phe Leu Lys Thr Gly Gly Pro Ala Thr Asn Met Asp
            165                 170                 175

Asn Ile Thr Ser Gly Leu Leu Gly Pro Leu Leu Val Leu Gln Ala Val
            180                 185                 190

Cys Phe Leu Leu Thr Lys Ile Leu Thr Ile Pro Gln Ser Leu Asp Ser
            195                 200                 205

Trp Trp Thr Ser Leu Asn Phe Leu Gly Gly Thr Pro Gly Cys Pro Gly
        210                 215                 220

Gln Asn Ser Gln Ser Pro Thr Ser Asn His Leu Pro Thr Ser Cys Pro
225                 230                 235                 240

Pro Thr Cys Pro Gly Tyr Arg Trp Met Cys Leu Arg Arg Phe Ile Ile
            245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Leu Pro Gly Ser Thr
            275                 280                 285

Thr Thr Ser Thr Gly Pro Cys Lys Thr Cys Thr Thr Leu Ala Gln Gly
290                 295                 300

Thr Ser Met Phe Pro Ser Cys Cys Cys Ser Lys Pro Ser Asp Gly Asn
305                 310                 315                 320

Cys Thr Cys Ile Pro Ile Pro Ser Ser Trp Ala Leu Gly Lys Tyr Leu
            325                 330                 335

Trp Glu Trp Ala Ser Ala Arg Phe Ser Trp Leu Ser Leu Leu Val Gln
            340                 345                 350

Phe Val Gln Trp Cys Val Gly Leu Ser Pro Thr Val Trp Leu Leu Val
            355                 360                 365

Ile Trp Met Ile Trp Tyr Trp Gly Pro Asn Leu Cys Ser Ile Leu Ser
            370                 375                 380

Pro Phe Ile Pro Leu Leu Pro Ile Phe Cys Tyr Leu Trp Val Ser Ile
385                 390                 395                 400

<210> SEQ ID NO 47
<211> LENGTH: 400
<212> TYPE: PRT
<213> ORGANISM: Hepatitis B virus

<400> SEQUENCE: 47

Met Gly Ala Pro Leu Ser Thr Thr Arg Arg Gly Met Gly Gln Asn Leu
1               5                   10                  15

Ser Val Pro Asn Pro Leu Gly Phe Phe Pro Asp His Gln Leu Asp Pro
            20                  25                  30

Leu Phe Arg Ala Asn Ser Ser Ser Pro Asp Trp Asp Phe Asn Lys Asp
            35                  40                  45

Lys Asp Asn Trp Pro Met Ala Asn Lys Val Gly Val Gly Gly Tyr Gly
        50                  55                  60

Pro Gly Phe Thr Pro Pro His Gly Gly Leu Leu Gly Trp Ser Pro Gln
65                  70                  75                  80

Ala Gln Gly Val Leu Thr Thr Leu Pro Ala Asp Pro Pro Pro Ala Ser
            85                  90                  95

Thr Asn Arg Arg Ser Gly Arg Lys Pro Thr Pro Val Ser Pro Pro Leu
            100                 105                 110

Arg Asp Thr His Pro Gln Ala Met Gln Trp Asn Ser Thr Gln Phe His

```
            115                 120                 125
Gln Ala Leu Leu Asp Pro Arg Val Arg Ala Leu Tyr Phe Pro Ala Gly
    130                 135                 140

Gly Ser Ser Ser Glu Thr Gln Asn Pro Ala Pro Thr Ile Ala Ser Leu
145                 150                 155                 160

Thr Ser Ser Ile Phe Leu Lys Thr Gly Gly Pro Ala Thr Asn Met Asp
                165                 170                 175

Asn Ile Thr Ser Gly Leu Leu Gly Pro Leu Leu Val Leu Gln Ala Val
                180                 185                 190

Cys Phe Leu Leu Thr Lys Ile Leu Thr Ile Pro Gln Ser Leu Asp Ser
            195                 200                 205

Trp Trp Thr Ser Leu Asn Phe Leu Gly Gly Thr Pro Gly Cys Pro Gly
        210                 215                 220

Gln Asn Ser Gln Ser Pro Thr Ser Asn His Leu Pro Thr Ser Cys Pro
225                 230                 235                 240

Pro Thr Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
                260                 265                 270

Asp Tyr Gln Gly Met Leu Pro Val Cys Pro Leu Leu Pro Gly Ser Thr
            275                 280                 285

Thr Thr Ser Thr Gly Pro Cys Lys Thr Cys Thr Thr Leu Ala Gln Gly
    290                 295                 300

Thr Ser Met Phe Pro Ser Cys Cys Cys Ser Lys Pro Ser Asp Gly Asn
305                 310                 315                 320

Cys Thr Cys Ile Pro Ile Pro Ser Ser Trp Ala Leu Gly Lys Tyr Leu
                325                 330                 335

Trp Glu Trp Ala Ser Ala Arg Phe Ser Trp Leu Ser Leu Leu Val Gln
                340                 345                 350

Phe Val Gln Trp Cys Val Gly Leu Ser Pro Thr Val Trp Leu Leu Val
            355                 360                 365

Ile Trp Met Ile Trp Tyr Trp Gly Pro Asn Leu Cys Ser Ile Leu Ser
370                 375                 380

Pro Phe Ile Pro Leu Leu Pro Ile Phe Cys Tyr Leu Trp Val Ser Ile
385                 390                 395                 400
```

<210> SEQ ID NO 48
<211> LENGTH: 395
<212> TYPE: PRT
<213> ORGANISM: Hepatitis B virus

<400> SEQUENCE: 48

```
Met Gly Leu Ser Trp Thr Val Pro Leu Glu Trp Gly Lys Asn Leu Ser
1               5                   10                  15

Thr Ser Asn Pro Leu Gly Phe Leu Pro Asp His Gln Leu Asp Pro Ala
                20                  25                  30

Phe Arg Ala Asn Thr Asn Asn Pro Asp Trp Asp Phe Asn Pro Lys Lys
            35                  40                  45

Asp Pro Trp Pro Glu Ala Asn Lys Val Gly Val Gly Ala Tyr Gly Pro
        50                  55                  60

Gly Phe Thr Pro Pro His Gly Gly Leu Leu Gly Trp Ser Pro Gln Ser
65                  70                  75                  80

Gln Gly Thr Leu Thr Thr Leu Pro Ala Asp Pro Pro Pro Ala Ser Thr
                85                  90                  95
```

Asn Arg Gln Ser Gly Arg Gln Pro Thr Pro Ile Ser Pro Pro Leu Arg
                100                 105                 110

Asp Ser His Pro Gln Ala Met Gln Trp Asn Ser Thr Ala Phe His Gln
            115                 120                 125

Ala Leu Gln Asn Pro Lys Val Ser Pro Ala Gly Gly Ser Ser Ser Gly
        130                 135                 140

Ile Val Asn Leu Val Pro Thr Ile Ala Ser His Ile Ser Ser Ile Phe
145                 150                 155                 160

Ser Arg Ile Gly Asp Pro Val Pro Asn Met Glu Asn Ile Thr Ser Gly
                165                 170                 175

Phe Leu Gly Pro Leu Leu Val Leu Gln Ala Gly Phe Phe Leu Leu Thr
            180                 185                 190

Arg Ile Leu Thr Ile Pro Gln Ser Leu Asp Ser Trp Trp Thr Ser Leu
        195                 200                 205

Asn Phe Leu Gly Gly Val Pro Val Cys Pro Gly Leu Asn Ser Gln Ser
210                 215                 220

Pro Thr Ser Asn His Ser Pro Ile Ser Cys Pro Pro Thr Cys Pro Gly
225                 230                 235                 240

Tyr Arg Trp Met Cys Leu Arg Arg Phe Ile Ile Phe Leu Phe Ile Leu
                245                 250                 255

Leu Leu Cys Leu Ile Phe Leu Leu Val Leu Leu Asp Tyr Gln Gly Met
            260                 265                 270

Leu Pro Val Cys Pro Leu Ile Pro Gly Ser Ser Thr Thr Ser Thr Gly
        275                 280                 285

Pro Cys Lys Thr Cys Thr Thr Pro Ala Gln Gly Asn Ser Met Tyr Pro
290                 295                 300

Ser Cys Cys Cys Thr Lys Pro Ser Asp Gly Asn Cys Thr Cys Ile Pro
305                 310                 315                 320

Ile Pro Ser Ser Trp Ala Phe Ala Lys Tyr Leu Trp Glu Trp Ala Ser
                325                 330                 335

Val Arg Phe Ser Trp Leu Ser Leu Leu Val Pro Phe Val Gln Trp Phe
            340                 345                 350

Val Gly Leu Ser Pro Thr Val Trp Leu Ser Ala Ile Trp Met Met Trp
        355                 360                 365

Tyr Trp Gly Pro Asn Leu Tyr Asn Ile Leu Ser Pro Phe Ile Pro Leu
370                 375                 380

Leu Pro Ile Phe Phe Phe Leu Trp Val Tyr Ile
385                 390                 395

<210> SEQ ID NO 49
<211> LENGTH: 399
<212> TYPE: PRT
<213> ORGANISM: Hepatitis B virus

<400> SEQUENCE: 49

Met Gly Leu Ser Trp Thr Val Pro Leu Glu Trp Gly Lys Asn Leu Ser
1               5                   10                  15

Thr Ser Asn Pro Leu Gly Phe Leu Pro Asp His Gln Leu Asp Pro Ala
            20                  25                  30

Phe Arg Ala Asn Thr Asn Asn Pro Asp Trp Asp Phe Asn Pro Lys Lys
        35                  40                  45

Asp Pro Trp Pro Glu Ala Asn Lys Val Gly Val Gly Ala Tyr Gly Pro
    50                  55                  60

Gly Phe Thr Pro Pro His Gly Gly Leu Leu Gly Trp Ser Leu Gln Ser
65                  70                  75                  80

```
Gln Gly Thr Leu Thr Thr Leu Pro Ala Asp Pro Pro Ala Ser Thr
            85                  90                  95

Asn Arg Gln Ser Gly Arg Gln Pro Thr Pro Ile Ser Pro Pro Leu Arg
            100                 105                 110

Asp Ser His Pro Gln Ala Met Gln Trp Asn Ser Thr Ala Phe His Gln
        115                 120                 125

Ala Leu Gln Asn Pro Lys Val Arg Gly Leu Tyr Phe Pro Ala Gly Gly
    130                 135                 140

Ser Ser Ser Gly Ile Val Asn Pro Val Pro Thr Ile Ala Ser His Ile
145                 150                 155                 160

Ser Ser Ile Phe Ser Arg Ile Gly Asp Pro Ala Pro Asn Met Glu Asn
                165                 170                 175

Ile Thr Ser Gly Phe Leu Gly Pro Leu Leu Val Leu Gln Ala Gly Phe
            180                 185                 190

Phe Leu Leu Thr Arg Ile Leu Thr Ile Pro Gln Ser Leu Asp Ser Trp
        195                 200                 205

Trp Thr Ser Leu Asn Phe Leu Gly Gly Val Pro Val Cys Pro Gly Leu
    210                 215                 220

Asn Ser Gln Ser Pro Thr Ser Asn His Ser Pro Ile Ser Cys Pro Pro
225                 230                 235                 240

Thr Cys Pro Gly Tyr Arg Trp Met Cys Leu Arg Arg Phe Ile Ile Phe
                245                 250                 255

Leu Phe Ile Leu Leu Leu Cys Leu Ile Phe Leu Leu Val Leu Leu Asp
            260                 265                 270

Tyr Gln Gly Met Leu Pro Val Cys Pro Leu Ile Pro Gly Ser Ser Thr
        275                 280                 285

Thr Ser Thr Gly Pro Cys Lys Thr Cys Thr Thr Pro Ala Gln Gly Asn
    290                 295                 300

Ser Met Tyr Pro Ser Cys Cys Cys Thr Lys Pro Ser Asp Gly Asn Cys
305                 310                 315                 320

Thr Cys Ile Pro Ile Pro Ser Ser Trp Ala Phe Ala Lys Tyr Leu Trp
                325                 330                 335

Glu Trp Ala Ser Val Arg Phe Ser Trp Leu Ser Leu Leu Val Pro Phe
            340                 345                 350

Val Gln Trp Phe Val Gly Leu Ser Pro Thr Val Trp Leu Ser Ala Ile
        355                 360                 365

Trp Met Met Trp Tyr Trp Gly Pro Asn Leu Tyr Asn Ile Leu Ser Pro
    370                 375                 380

Phe Ile Pro Leu Leu Pro Ile Phe Phe Cys Leu Trp Val Tyr Ile
385                 390                 395

<210> SEQ ID NO 50
<211> LENGTH: 399
<212> TYPE: PRT
<213> ORGANISM: Hepatitis B virus

<400> SEQUENCE: 50

Met Gly Leu Ser Trp Thr Val Pro Leu Glu Trp Gly Lys Asn Leu Ser
1               5                   10                  15

Thr Ser Asn Pro Leu Gly Phe Leu Pro Asp His Gln Leu Asp Pro Ala
            20                  25                  30

Phe Arg Ala Asn Thr Asn Asn Pro Asp Trp Asp Phe Asn Pro Lys Lys
        35                  40                  45

Asp Pro Trp Pro Glu Ala Asn Lys Val Gly Val Gly Ala Tyr Gly Pro
```

```
            50                  55                  60
Gly Phe Thr Pro Pro His Gly Gly Leu Leu Gly Trp Ser Leu Gln Ser
 65                  70                  75                  80

Gln Gly Thr Leu Thr Thr Leu Pro Ala Asp Pro Pro Ala Ser Thr
                 85                  90                  95

Asn Arg Gln Ser Gly Arg Gln Pro Thr Pro Ile Ser Pro Pro Leu Arg
                100                 105                 110

Asp Ser His Pro Gln Ala Met Gln Trp Asn Ser Thr Ala Phe His Gln
                115                 120                 125

Ala Leu Gln Asn Pro Lys Val Arg Gly Leu Tyr Leu Pro Ala Gly Gly
            130                 135                 140

Ser Ser Ser Gly Ile Val Asn Pro Val Pro Thr Ile Ala Ser His Ile
145                 150                 155                 160

Ser Ser Ile Phe Ser Arg Ile Gly Asp Pro Ala Pro Asn Met Glu Asn
                165                 170                 175

Ile Thr Ser Gly Phe Leu Gly Pro Leu Leu Val Leu Gln Ala Gly Phe
                180                 185                 190

Phe Leu Leu Thr Arg Ile Leu Thr Ile Pro Gln Ser Leu Asp Ser Trp
            195                 200                 205

Trp Thr Ser Leu Asn Phe Leu Gly Gly Val Pro Val Cys Pro Gly Leu
210                 215                 220

Asn Ser Gln Ser Pro Thr Ser Asn His Ser Pro Ile Ser Cys Pro Pro
225                 230                 235                 240

Thr Cys Pro Gly Tyr Arg Trp Met Cys Leu Arg Arg Phe Ile Ile Phe
                245                 250                 255

Leu Phe Ile Leu Leu Leu Cys Leu Ile Phe Leu Leu Val Leu Leu Asp
                260                 265                 270

Tyr Gln Gly Met Leu Pro Val Cys Pro Leu Ile Pro Gly Ser Ser Thr
            275                 280                 285

Thr Ser Thr Gly Pro Cys Lys Thr Cys Thr Thr Pro Ala Gln Gly Asn
290                 295                 300

Ser Met Tyr Pro Ser Cys Cys Cys Thr Lys Pro Ser Asp Gly Asn Cys
305                 310                 315                 320

Thr Cys Ile Pro Ile Pro Ser Ser Trp Ala Phe Ala Lys Tyr Leu Trp
                325                 330                 335

Glu Trp Ala Ser Val Arg Phe Ser Trp Leu Ser Leu Leu Val Pro Phe
            340                 345                 350

Val Gln Trp Phe Val Gly Leu Ser Pro Thr Val Trp Leu Ser Ala Ile
            355                 360                 365

Trp Met Met Trp Tyr Trp Gly Pro Asn Leu Tyr Asn Ile Leu Ser Pro
370                 375                 380

Phe Ile Pro Leu Leu Pro Ile Phe Phe Cys Leu Trp Val Tyr Ile
385                 390                 395

<210> SEQ ID NO 51
<211> LENGTH: 399
<212> TYPE: PRT
<213> ORGANISM: Hepatitis B virus

<400> SEQUENCE: 51

Met Gly Leu Ser Trp Thr Val Pro Leu Glu Trp Gly Lys Asn Leu Ser
 1               5                  10                  15

Thr Ser Asn Pro Leu Gly Phe Leu Pro Asp His Gln Leu Asp Pro Ala
                20                  25                  30
```

```
Phe Arg Ala Asn Thr Asn Asn Pro Asp Trp Asp Phe Asn Pro Lys Lys
             35                  40                  45

Asp Pro Trp Pro Glu Ala Asn Lys Val Gly Val Gly Ala Tyr Gly Pro
 50                  55                  60

Gly Phe Thr Pro Pro His Gly Gly Leu Leu Gly Trp Ser Pro Gln Ser
 65                  70                  75                  80

Gln Gly Thr Leu Thr Thr Leu Pro Ala Asp Pro Pro Ala Ser Thr
             85                  90                  95

Asn Arg Gln Ser Gly Arg Gln Pro Thr Pro Ile Ser Pro Pro Leu Arg
            100                 105                 110

Asp Ser His Pro Gln Ala Met Gln Trp Asn Ser Thr Ala Phe His Gln
            115                 120                 125

Ala Leu Gln Asn Pro Lys Val Arg Gly Leu Tyr Phe Pro Ala Gly Gly
            130                 135                 140

Ser Ser Ser Gly Ile Val Asn Pro Val Pro Thr Ile Ala Ser His Ile
145                 150                 155                 160

Ser Ser Ile Phe Ser Arg Ile Gly Asp Pro Ala Pro Asn Met Glu Asn
                165                 170                 175

Ile Thr Ser Gly Phe Leu Gly Pro Leu Leu Val Leu Gln Ala Gly Phe
            180                 185                 190

Phe Leu Leu Thr Arg Ile Leu Thr Ile Pro Gln Asn Leu Asp Ser Trp
            195                 200                 205

Trp Thr Ser Leu Asn Phe Leu Gly Gly Val Pro Val Cys Pro Gly Leu
            210                 215                 220

Asn Ser Gln Ser Pro Thr Ser Asn His Ser Pro Ile Ser Cys Pro Pro
225                 230                 235                 240

Thr Cys Pro Gly Tyr Arg Trp Met Cys Leu Arg Arg Phe Ile Ile Phe
                245                 250                 255

Leu Phe Ile Leu Leu Leu Cys Leu Ile Phe Leu Leu Val Leu Leu Asp
            260                 265                 270

Tyr Gln Gly Met Leu Pro Val Cys Pro Leu Ile Pro Gly Ser Ser Thr
            275                 280                 285

Thr Ser Thr Gly Pro Cys Lys Thr Cys Thr Thr Pro Ala Gln Gly Asn
290                 295                 300

Ser Met Tyr Pro Ser Cys Cys Cys Thr Lys Pro Ser Asp Gly Asn Cys
305                 310                 315                 320

Thr Cys Ile Pro Ile Pro Ser Ser Trp Ala Phe Ala Lys Tyr Leu Trp
                325                 330                 335

Glu Trp Ala Ser Val Arg Phe Ser Trp Leu Ser Leu Leu Val Pro Phe
            340                 345                 350

Val Gln Trp Phe Val Gly Leu Ser Pro Thr Val Trp Leu Ser Ala Ile
            355                 360                 365

Trp Met Met Trp Tyr Trp Gly Pro Asn Leu Tyr Asn Ile Leu Ser Pro
            370                 375                 380

Phe Ile Pro Leu Leu Pro Ile Phe Phe Cys Leu Trp Val Tyr Ile
385                 390                 395

<210> SEQ ID NO 52
<211> LENGTH: 395
<212> TYPE: PRT
<213> ORGANISM: Hepatitis B virus

<400> SEQUENCE: 52

Met Gly Leu Ser Trp Thr Val Pro Leu Glu Trp Gly Lys Asn Leu Ser
 1               5                  10                  15
```

Thr Ser Asn Pro Leu Gly Phe Leu Pro Asp His Gln Leu Asp Pro Ala
            20                  25                  30

Phe Arg Ala Asn Thr Asn Pro Asp Trp Asp Phe Asn Pro Lys Lys
        35                  40                  45

Asp Pro Trp Pro Glu Ala Asn Lys Val Gly Val Gly Ala Tyr Gly Pro
50                  55                  60

Gly Phe Thr Pro Pro His Gly Gly Leu Leu Gly Trp Ser Pro Gln Ser
65                  70                  75                  80

Gln Gly Thr Leu Thr Thr Leu Pro Ala Asp Pro Pro Ala Ser Thr
                85                  90                  95

Asn Arg Gln Ser Gly Arg Gln Pro Thr Pro Ile Ser Pro Pro Leu Arg
                100                 105                 110

Asp Ser His Pro Gln Ala Met Gln Trp Asn Ser Thr Ala Phe His Gln
            115                 120                 125

Ala Leu Gln Asn Pro Lys Val Ser Pro Ala Gly Ser Ser Ser Gly
130                 135                 140

Ile Val Asn Pro Val Pro Thr Ile Ala Ser His Ile Ser Ser Ile Phe
145                 150                 155                 160

Ser Arg Ile Gly Asp Pro Ala Pro Asn Met Glu Asn Ile Thr Ser Gly
                165                 170                 175

Phe Leu Gly Pro Leu Leu Val Leu Gln Ala Gly Phe Phe Leu Leu Thr
            180                 185                 190

Arg Ile Leu Thr Ile Pro Gln Ser Leu Asp Ser Trp Trp Thr Ser Leu
        195                 200                 205

Asn Phe Leu Gly Gly Val Pro Val Cys Pro Gly Leu Asn Ser Gln Ser
    210                 215                 220

Pro Thr Ser Asn His Ser Pro Ile Ser Cys Pro Pro Thr Cys Pro Gly
225                 230                 235                 240

Tyr Arg Trp Met Cys Leu Arg Arg Phe Ile Ile Phe Leu Phe Ile Leu
                245                 250                 255

Leu Leu Cys Leu Ile Phe Leu Leu Val Leu Leu Asp Tyr Gln Gly Met
            260                 265                 270

Leu Pro Val Cys Pro Leu Ile Pro Gly Ser Ser Thr Thr Ser Thr Gly
        275                 280                 285

Pro Cys Lys Thr Cys Thr Thr Pro Ala Gln Gly Asn Ser Met Tyr Pro
    290                 295                 300

Ser Cys Cys Cys Thr Lys Pro Ser Asp Gly Asn Cys Thr Cys Ile Pro
305                 310                 315                 320

Ile Pro Ser Ser Trp Ala Phe Ala Lys Tyr Leu Trp Glu Trp Ala Ser
                325                 330                 335

Val Arg Phe Ser Trp Leu Ser Leu Leu Val Pro Phe Val Gln Trp Phe
            340                 345                 350

Val Gly Leu Pro Pro Thr Val Trp Leu Ser Ala Ile Trp Met Met Trp
        355                 360                 365

Tyr Trp Gly Pro Asn Leu Tyr Asn Ile Leu Ser Pro Phe Ile Pro Leu
    370                 375                 380

Leu Pro Ile Phe Phe Phe Leu Trp Val Tyr Ile
385                 390                 395

<210> SEQ ID NO 53
<211> LENGTH: 395
<212> TYPE: PRT
<213> ORGANISM: Hepatitis B virus

<400> SEQUENCE: 53

```
Met Gly Leu Ser Trp Thr Val Pro Leu Glu Trp Gly Lys Asn Leu Ser
1               5                   10                  15

Thr Ser Asn Pro Leu Gly Phe Leu Pro Asp His Gln Leu Asp Pro Ala
            20                  25                  30

Phe Arg Ala Asn Thr Asn Asn Pro Asp Trp Asp Phe Asn Pro Lys Lys
        35                  40                  45

Asp Pro Trp Pro Glu Ala Asn Lys Val Gly Val Gly Ala Tyr Gly Pro
    50                  55                  60

Gly Phe Thr Pro Pro His Gly Gly Leu Leu Gly Trp Ser Pro Gln Ser
65                  70                  75                  80

Gln Gly Thr Leu Thr Thr Leu Pro Ala Asp Pro Pro Ala Ser Thr
                85                  90                  95

Asn Arg Gln Ser Gly Arg Gln Pro Thr Pro Ile Ser Pro Pro Leu Arg
                100                 105                 110

Asp Ser His Pro Gln Ala Met Gln Trp Asn Ser Thr Ala Phe His Gln
            115                 120                 125

Ala Leu Gln Asn Pro Lys Val Ser Pro Ala Gly Gly Ser Ser Ser Gly
        130                 135                 140

Ile Val Asn Pro Val Pro Thr Ile Ala Ser His Ile Ser Ser Ile Phe
145                 150                 155                 160

Ser Arg Ile Gly Asp Pro Ala Pro Asn Met Glu Asn Ile Thr Ser Gly
                165                 170                 175

Phe Leu Gly Pro Leu Leu Val Leu Gln Ala Gly Phe Phe Leu Leu Thr
            180                 185                 190

Arg Ile Leu Thr Ile Pro Gln Ser Leu Asp Ser Trp Trp Thr Ser Leu
        195                 200                 205

Asn Phe Leu Gly Gly Val Pro Val Cys Pro Gly Leu Asn Ser Gln Ser
    210                 215                 220

Pro Thr Ser Asn His Ser Pro Ile Ser Cys Pro Pro Thr Cys Pro Gly
225                 230                 235                 240

Tyr Arg Trp Met Cys Leu Arg Arg Phe Ile Ile Phe Leu Phe Ile Leu
                245                 250                 255

Leu Leu Cys Leu Ile Phe Leu Leu Val Leu Leu Asp Tyr Gln Gly Met
            260                 265                 270

Leu Pro Val Cys Pro Leu Ile Pro Gly Ser Ser Thr Thr Ser Thr Gly
        275                 280                 285

Pro Cys Lys Thr Cys Thr Thr Pro Ala Gln Gly Asn Ser Met Tyr Pro
    290                 295                 300

Ser Cys Cys Cys Thr Lys Pro Ser Asp Gly Asn Cys Thr Cys Ile Pro
305                 310                 315                 320

Ile Pro Ser Ser Trp Ala Phe Ala Lys Tyr Leu Trp Glu Trp Val Ser
                325                 330                 335

Val Arg Phe Ser Trp Leu Ser Leu Leu Val Pro Phe Val Gln Trp Phe
            340                 345                 350

Val Gly Leu Ser Pro Thr Val Trp Leu Ser Ala Ile Trp Met Met Trp
        355                 360                 365

Tyr Trp Gly Pro Asn Leu Tyr Asn Ile Leu Ser Pro Phe Ile Pro Leu
    370                 375                 380

Leu Pro Ile Phe Phe Phe Leu Trp Val Tyr Ile
385                 390                 395
```

<210> SEQ ID NO 54

```
<211> LENGTH: 400
<212> TYPE: PRT
<213> ORGANISM: Hepatitis B virus

<400> SEQUENCE: 54
```

| | | | | | | | | | | | | | | |
|---|---|---|---|---|---|---|---|---|---|---|---|---|---|---|
| Met | Gly | Ala | Pro | Leu | Ser | Thr | Ala | Arg | Arg | Gly | Met | Gly | Gln | Asn | Leu |
| 1 | | | | 5 | | | | | 10 | | | | | 15 | |
| Ser | Val | Pro | Asn | Pro | Leu | Gly | Phe | Phe | Pro | Asp | His | Gln | Leu | Asp | Pro |
| | | | 20 | | | | | 25 | | | | | 30 | | |
| Leu | Phe | Arg | Ala | Asn | Ser | Ser | Pro | Asp | Trp | Asp | Phe | Asn | Thr | Asn | |
| | | 35 | | | | | 40 | | | | | 45 | | | |
| Lys | Asp | Asn | Trp | Pro | Met | Ala | Asn | Lys | Val | Gly | Val | Gly | Gly | Phe | Gly |
| 50 | | | | | 55 | | | | | 60 | | | | | |
| Pro | Gly | Phe | Thr | Pro | Pro | His | Gly | Gly | Leu | Leu | Gly | Trp | Ser | Pro | Gln |
| 65 | | | | | 70 | | | | | 75 | | | | | 80 |
| Ala | Gln | Gly | Ile | Leu | Thr | Thr | Ser | Pro | Pro | Asp | Pro | Pro | Ala | Ser | |
| | | | | 85 | | | | | 90 | | | | | 95 | |
| Thr | Asn | Arg | Arg | Ser | Gly | Arg | Lys | Pro | Thr | Pro | Val | Ser | Pro | Pro | Leu |
| | | | 100 | | | | | 105 | | | | | 110 | | |
| Arg | Asp | Thr | His | Pro | Gln | Ala | Met | Gln | Trp | Asn | Ser | Thr | Gln | Phe | His |
| | | 115 | | | | | 120 | | | | | 125 | | | |
| Gln | Ala | Leu | Leu | Asp | Pro | Arg | Val | Arg | Gly | Leu | Tyr | Phe | Pro | Ala | Gly |
| | 130 | | | | | 135 | | | | | 140 | | | | |
| Gly | Ser | Ser | Ser | Glu | Thr | Gln | Asn | Pro | Ala | Pro | Thr | Ile | Ala | Ser | Leu |
| 145 | | | | | 150 | | | | | 155 | | | | | 160 |
| Thr | Ser | Ser | Ile | Phe | Ser | Lys | Thr | Gly | Asp | Pro | Ala | Met | Asn | Met | Glu |
| | | | | 165 | | | | | 170 | | | | | 175 | |
| Asn | Ile | Thr | Ser | Gly | Leu | Leu | Gly | Pro | Leu | Leu | Val | Leu | Gln | Ala | Val |
| | | | 180 | | | | | 185 | | | | | 190 | | |
| Cys | Phe | Leu | Leu | Thr | Lys | Ile | Leu | Thr | Ile | Pro | Lys | Ser | Leu | Asp | Ser |
| | | 195 | | | | | 200 | | | | | 205 | | | |
| Trp | Trp | Thr | Ser | Leu | Asn | Phe | Leu | Gly | Val | Pro | Pro | Gly | Cys | Pro | Gly |
| | 210 | | | | | 215 | | | | | 220 | | | | |
| Gln | Asn | Ser | Gln | Ser | Pro | Ile | Ser | Asn | His | Leu | Pro | Thr | Ser | Cys | Pro |
| 225 | | | | | 230 | | | | | 235 | | | | | 240 |
| Pro | Thr | Cys | Pro | Gly | Tyr | Arg | Trp | Met | Cys | Leu | Arg | Arg | Phe | Ile | Ile |
| | | | | 245 | | | | | 250 | | | | | 255 | |
| Phe | Leu | Phe | Ile | Leu | Leu | Leu | Cys | Leu | Ile | Phe | Leu | Leu | Val | Leu | Leu |
| | | | 260 | | | | | 265 | | | | | 270 | | |
| Asp | Tyr | Gln | Gly | Met | Leu | Pro | Val | Cys | Pro | Leu | Leu | Pro | Gly | Ser | Thr |
| | | 275 | | | | | 280 | | | | | 285 | | | |
| Thr | Thr | Ser | Thr | Gly | Pro | Cys | Lys | Thr | Cys | Thr | Thr | Leu | Ala | Gln | Gly |
| | 290 | | | | | 295 | | | | | 300 | | | | |
| Thr | Ser | Met | Phe | Pro | Ser | Cys | Cys | Cys | Thr | Lys | Pro | Ser | Asp | Gly | Asn |
| 305 | | | | | 310 | | | | | 315 | | | | | 320 |
| Cys | Thr | Cys | Ile | Pro | Ile | Pro | Ser | Ser | Trp | Ala | Phe | Gly | Lys | Tyr | Leu |
| | | | | 325 | | | | | 330 | | | | | 335 | |
| Trp | Glu | Trp | Ala | Ser | Ala | Arg | Phe | Ser | Trp | Leu | Ser | Leu | Leu | Val | Gln |
| | | | 340 | | | | | 345 | | | | | 350 | | |
| Phe | Val | Gln | Trp | Cys | Val | Gly | Leu | Ser | Pro | Thr | Val | Trp | Leu | Leu | Val |
| | | 355 | | | | | 360 | | | | | 365 | | | |
| Ile | Trp | Met | Ile | Trp | Tyr | Trp | Gly | Pro | Asn | Leu | Cys | Ser | Ile | Leu | Ser |
| | 370 | | | | | 375 | | | | | 380 | | | | |
| Pro | Phe | Ile | Pro | Leu | Leu | Pro | Ile | Phe | Cys | Tyr | Leu | Trp | Ala | Ser | Ile |

<210> SEQ ID NO 55
<211> LENGTH: 399
<212> TYPE: PRT
<213> ORGANISM: Hepatitis B virus

<400> SEQUENCE: 55

Met Gly Ala Pro Leu Ser Thr Ala Arg Arg Gly Met Gly Gln Asn Leu
1               5                   10                  15

Ser Val Pro Asn Pro Leu Gly Phe Phe Pro Asp His Gln Leu Asp Pro
            20                  25                  30

Leu Phe Arg Ala Asn Ser Ser Pro Asp Trp Asp Phe Asn Thr Asn
        35                  40                  45

Lys Asp Asn Trp Pro Met Ala Asn Lys Val Gly Val Gly Gly Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Ser Pro Pro Asp Pro Pro Ala Ser
                85                  90                  95

Thr Asn Arg Arg Ser Gly Arg Lys Pro Thr Pro Val Ser Pro Pro Leu
            100                 105                 110

Arg Glu Thr His Pro Gln Ala Met Gln Trp Asn Ser Thr Gln Phe His
        115                 120                 125

Gln Ala Leu Leu Asp Pro Arg Val Arg Gly Leu Tyr Pro Ala Gly Gly
    130                 135                 140

Ser Ser Ser Glu Thr Gln Asn Pro Ala Pro Thr Ile Ala Ser Leu Thr
145                 150                 155                 160

Ser Ser Ile Phe Ser Lys Thr Gly Asp Pro Ala Met Asn Met Glu Asn
                165                 170                 175

Ile Thr Ser Gly Leu Leu Gly Pro Leu Leu Val Leu Gln Ala Val Cys
            180                 185                 190

Phe Leu Leu Thr Lys Ile Leu Thr Ile Pro Gln Ser Leu Asp Ser Trp
        195                 200                 205

Trp Thr Ser Leu Asn Phe Leu Gly Val Pro Pro Gly Cys Pro Gly Gln
    210                 215                 220

Asn Ser Gln Ser Pro Ile Ser Asn His Leu Pro Thr Ser Cys Pro Pro
225                 230                 235                 240

Thr Cys Pro Gly Tyr Arg Trp Met Cys Leu Arg Arg Phe Ile Ile Phe
                245                 250                 255

Leu Phe Ile Leu Leu Leu Cys Leu Ile Phe Leu Leu Val Leu Leu Asp
            260                 265                 270

Tyr Gln Gly Met Leu Pro Val Cys Pro Leu Leu Pro Gly Ser Thr Thr
        275                 280                 285

Thr Ser Thr Gly Pro Cys Lys Thr Cys Thr Thr Leu Ala Gln Gly Thr
    290                 295                 300

Ser Met Phe Pro Ser Cys Cys Cys Thr Lys Pro Ser Asp Gly Asn Cys
305                 310                 315                 320

Thr Cys Ile Pro Ile Pro Ser Ser Trp Ala Phe Gly Lys Tyr Leu Trp
                325                 330                 335

Glu Trp Ala Ser Ala Arg Phe Ser Trp Leu Ser Leu Leu Val Gln Phe
            340                 345                 350

Val Gln Trp Cys Val Gly Leu Ser Pro Thr Val Trp Leu Leu Val Ile
        355                 360                 365

```
Trp Met Ile Trp Tyr Trp Gly Pro Asn Leu Cys Ser Ile Leu Arg Pro
            370                 375                 380

Phe Ile Pro Leu Leu Pro Ile Phe Cys Tyr Leu Trp Ala Ser Ile
385                 390                 395

<210> SEQ ID NO 56
<211> LENGTH: 400
<212> TYPE: PRT
<213> ORGANISM: Hepatitis B virus

<400> SEQUENCE: 56

Met Gly Ala Pro Leu Ser Thr Ala Arg Arg Gly Met Gly Gln Asn Leu
1               5                   10                  15

Ser Val Pro Asn Pro Leu Gly Phe Phe Pro Asp His Gln Leu Asp Pro
            20                  25                  30

Leu Phe Arg Ala Asn Ser Ser Pro Asp Trp Asp Phe Asn Thr Asn
        35                  40                  45

Lys Asp Asn Trp Pro Met Ala Asn Lys Val Gly Val Gly Gly Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Ser Pro Pro Asp Pro Pro Pro Ala Ser
                85                  90                  95

Thr Asn Arg Arg Ser Gly Arg Lys Pro Thr Pro Val Ser Pro Pro Leu
            100                 105                 110

Arg Asp Thr His Pro Gln Ala Met Gln Trp Asn Ser Thr Gln Phe His
            115                 120                 125

Gln Ala Leu Leu Asp Pro Arg Val Arg Gly Leu Tyr Leu Pro Ala Gly
    130                 135                 140

Gly Ser Ser Ser Glu Thr Gln Asn Pro Ala Pro Thr Ile Ala Ser Leu
145                 150                 155                 160

Thr Ser Ser Ile Phe Ser Lys Thr Gly Asp Pro Ala Met Asn Met Glu
                165                 170                 175

Asn Ile Thr Ser Gly Leu Leu Gly Pro Leu Leu Val Leu Gln Ala Val
            180                 185                 190

Cys Phe Leu Leu Thr Lys Ile Leu Thr Ile Pro Lys Ser Leu Asp Ser
        195                 200                 205

Trp Trp Thr Ser Leu Asn Phe Leu Gly Val Pro Pro Gly Cys Pro Gly
    210                 215                 220

Gln Asn Ser Gln Ser Pro Ile Ser Asn His Leu Pro Thr Ser Cys Pro
225                 230                 235                 240

Pro Thr Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Leu Pro Gly Ser Thr
        275                 280                 285

Thr Thr Ser Thr Gly Pro Cys Lys Thr Cys Thr Thr Leu Ala Gln Gly
    290                 295                 300

Thr Ser Met Phe Pro Ser Cys Cys Cys Thr Lys Pro Ser Asp Gly Asn
305                 310                 315                 320

Cys Thr Cys Ile Pro Ile Pro Ser Ser Trp Ala Phe Gly Lys Tyr Leu
                325                 330                 335

Trp Glu Trp Ala Ser Ala Arg Phe Ser Trp Leu Ser Leu Leu Val Gln
            340                 345                 350
```

```
Phe Val Gln Trp Cys Val Gly Leu Ser Pro Thr Val Trp Leu Val
        355                 360                 365

Ile Trp Met Ile Trp Tyr Trp Gly Pro Asn Leu Cys Ser Ile Leu Ser
370                 375                 380

Pro Phe Ile Pro Leu Leu Pro Ile Phe Cys Tyr Leu Trp Ala Ser Ile
385                 390                 395                 400

<210> SEQ ID NO 57
<211> LENGTH: 400
<212> TYPE: PRT
<213> ORGANISM: Hepatitis B virus

<400> SEQUENCE: 57

Met Gly Ala Pro Leu Ser Thr Ala Arg Arg Gly Met Gly Gln Asn Leu
1               5                   10                  15

Ser Val Pro Asn Pro Leu Gly Phe Phe Pro Asp His Gln Leu Asp Pro
            20                  25                  30

Leu Phe Arg Ala Asn Ser Ser Pro Asp Trp Asp Phe Asn Thr Asn
        35                  40                  45

Lys Asp Asn Trp Pro Met Ala Asn Lys Val Gly Val Gly Gly Phe Gly
50                  55                  60

Pro Gly Phe Thr Pro Pro His Gly Gly Leu Leu Gly Trp Ser Pro Gln
65                  70                  75                  80

Ala Gln Gly Ile Leu Thr Thr Ser Pro Pro Asp Pro Pro Pro Ala Ser
                85                  90                  95

Thr Asn Arg Arg Ser Gly Arg Lys Pro Thr Pro Val Ser Pro Pro Leu
            100                 105                 110

Arg Asp Thr His Pro Gln Ala Met Gln Trp Asn Ser Thr Gln Phe His
        115                 120                 125

Gln Ala Leu Leu Asp Pro Arg Val Arg Gly Leu Tyr Phe Pro Ala Gly
130                 135                 140

Gly Ser Ser Ser Glu Thr Gln Asn Pro Ala Pro Thr Ile Ala Ser Leu
145                 150                 155                 160

Thr Ser Ser Ile Phe Ser Lys Thr Gly Asp Pro Val Met Asn Met Glu
                165                 170                 175

Asn Ile Thr Ser Gly Leu Leu Gly Pro Leu Leu Val Leu Gln Ala Val
            180                 185                 190

Cys Phe Leu Leu Thr Lys Ile Leu Thr Ile Pro Lys Ser Leu Asp Ser
        195                 200                 205

Trp Trp Thr Ser Leu Asn Phe Leu Gly Val Pro Pro Gly Cys Pro Gly
210                 215                 220

Gln Asn Ser Gln Ser Pro Ile Ser Asn His Leu Pro Thr Ser Cys Pro
225                 230                 235                 240

Pro Thr Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Leu Pro Gly Ser Thr
        275                 280                 285

Thr Thr Ser Thr Gly Pro Cys Lys Thr Cys Thr Thr Leu Ala Gln Gly
290                 295                 300

Thr Ser Met Leu Pro Ser Cys Cys Cys Thr Lys Pro Ser Asp Gly Asn
305                 310                 315                 320

Cys Thr Cys Ile Pro Ile Pro Ser Ser Trp Ala Phe Gly Lys Tyr Leu
```

```
                325                 330                 335
Trp Glu Trp Ala Ser Ala Arg Phe Ser Trp Leu Ser Leu Leu Val Gln
        340                 345                 350

Phe Val Gln Trp Cys Val Gly Leu Ser Pro Thr Val Trp Leu Leu Val
        355                 360                 365

Ile Trp Met Ile Trp Tyr Trp Gly Pro Asn Leu Cys Ser Ile Leu Ser
    370                 375                 380

Pro Phe Ile Pro Leu Leu Pro Ile Phe Cys Tyr Leu Trp Ala Ser Ile
385                 390                 395                 400

<210> SEQ ID NO 58
<211> LENGTH: 8
<212> TYPE: PRT
<213> ORGANISM: artificial
<220> FEATURE:
<223> OTHER INFORMATION: protease recognition sequence

<400> SEQUENCE: 58

Leu Glu Val Leu Phe Gln Gly Pro
1               5

<210> SEQ ID NO 59
<211> LENGTH: 24
<212> TYPE: DNA
<213> ORGANISM: Artificial Sequence
<220> FEATURE:
<223> OTHER INFORMATION: rotease recognition sequence

<400> SEQUENCE: 59
ctggaagttc tgttccaggg gccc                                           24

<210> SEQ ID NO 60
<211> LENGTH: 6
<212> TYPE: PRT
<213> ORGANISM: Artificial Sequence
<220> FEATURE:
<223> OTHER INFORMATION: Partial amino acid sequence in Pre-S2 region

<400> SEQUENCE: 60

Ser Ile Ser Ala Arg Thr
1               5

<210> SEQ ID NO 61
<211> LENGTH: 6
<212> TYPE: PRT
<213> ORGANISM: Artificial Sequence
<220> FEATURE:
<223> OTHER INFORMATION: Partial amino acid sequence in Pre-S2 region

<400> SEQUENCE: 61

Ser Ile Leu Ser Lys Thr
1               5

<210> SEQ ID NO 62
<211> LENGTH: 6
<212> TYPE: PRT
<213> ORGANISM: Artificial Sequence
<220> FEATURE:
<223> OTHER INFORMATION: Partial amino acid sequence in Pre-S2 region

<400> SEQUENCE: 62

Ser Ile Phe Ser Arg Ile
1               5
```

```
<210> SEQ ID NO 63
<211> LENGTH: 21
<212> TYPE: DNA
<213> ORGANISM: Artificial Sequence
<220> FEATURE:
<223> OTHER INFORMATION: Primer

<400> SEQUENCE: 63
cacatcagga ttcctaggac c                                              21

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
aggttggtga gtgattggag                                                20

<210> SEQ ID NO 65
<211> LENGTH: 26
<212> TYPE: DNA
<213> ORGANISM: Artificial Sequence
<220> FEATURE:
<223> OTHER INFORMATION: Probe

<400> SEQUENCE: 65
cagagtctag actcgtggtg gacttc                                         26

<210> SEQ ID NO 66
<211> LENGTH: 183
<212> TYPE: PRT
<213> ORGANISM: Hepatitis B virus

<400> SEQUENCE: 66

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

VIRUS-LIKE PARTICLES INCLUDING HBS-L ANTIGEN PROTEIN FOR CAUSING IMMUNE RESPONSE AGAINST HBV

TECHNICAL FIELD

The present invention relates to a virus-like particle to be used for generating an immune response against HBV. The present invention also relates to a virus-like particle composition to be used for generating an immune response against HBV. The present invention further relates to a vaccine comprising them as active ingredients, to be used for the treatment and/or prevention of HBV.

BACKGROUND ART

Hepatitis B is an infection caused by the hepatitis B virus (this virus may also be referred to as "HBV" in this specification). The disease is known as a major cause of various liver disorders, such as acute hepatitis, chronic hepatitis, cirrhosis, hepatocellular cancers, and the like. It is said that there are 300,000,000 people who are infected with HBV worldwide. Hepatitis B is thus one of the world health problems.

HBV is a particle having DNA in its center, and a capsid surrounding the DNA; HBV further has an envelope structure including a large number of proteins in the lipid membrane present on its surface. Since the envelope structure is located at the outermost portion of the virus, and is used for immunological detection of HBV, this structure may also be referred to as a surface antigen (FIG. 1).

The full-length protein forming the surface antigen of HBV is referred to as "L protein." Three regions: Pre-S1 region, Pre-S2 region, and S region, are present in this order from the N-terminal on the outermost portion of the particle (FIG. 1). The Pre-S1 region serves as a sensor that recognizes a cell and enables binding thereto upon HBV infection of human hepatocytes. Human hepatocytes have an NTCP receptor, which serves as a receptor for HBV (Non-Patent Literature 1). It has been reported that when the NTCP receptor is highly expressed in a human hepatocyte-derived cell line that does not infect HBV, HBV infection occurs (Non-Patent Literature 2). Therefore, recently, confirmation of HBV infection-preventing effects has been widely performed using these cells.

An HBs antigen protein that lacks of Pre-S1 region from full length, L protein, and comprising only Pre-S2 region and S region, is referred to as "M protein." An HBs antigen protein lacking Pre-S1 region and Pre-S2 region from L protein, and thus comprising only S region, is referred to as "S protein." In this technical field, the definitions of the terms may sometimes be unclear; for example, an HBV surface antigen (Hepatitis B Surface Antigen, HBsAg) may mean an S antigen particle consisting of S protein. In this specification, as HBV surface antigen proteins, an antigen particle consisting of S protein is defined as S antigen or HBs-S antigen; an antigen particle consisting of M protein is defined as M antigen or HBs-M antigen; and an antigen particle consisting of L protein is defined as L antigen or HBs-L antigen, unless otherwise specified (FIG. 1).

The HBV antigen proteins described above can be produced by introducing genes encoding them into an expression system in which yeasts, animal cells, or like eukaryotic cells are used as the host cells. Such recombinant surface antigens are widely used as vaccines for preventing HBV. Of these, S antigens produced by yeasts have mainly been used in the market. As an exception, prophylactic vaccines (Genhevac B Pasteur and Sci-B-Vac) using an antigen comprising M protein and L protein produced in CHO cells are also commercially available (Non-Patent Literature 3 and 4). The raw material of Genhevac B Pasteur is an antigen in which M protein and S protein as HBV surface antigen proteins are mixed. The raw material of Sci-B-Vac is an antigen containing L protein, M protein, and S protein.

A major problem of the prophylactic vaccines using S antigens is the presence of vaccine non-responders, and slow onset of the preventive effect. Clinical studies of a prophylactic vaccine using an M antigen consisting of an M protein produced by yeast revealed that the Pre-S2 region has an immunogenicity higher than that of the S antigen, and that an antibody against Pre-S2 region was also produced in addition to an antibody against S region. Therefore, it was reported that this vaccine is effective to reduce the non-responders or accelerate the onset, and the like (Non-Patent Literature 5). L antigen has Pre-S1 region, an HBV sensor, in addition to the S region and the Pre-S2 region present in an M antigen. Therefore, when an L antigen is used as a prophylactic vaccine, an antibody against Pre-S1 region presented on the outermost portion is also produced. Thus, the L antigen vaccine is considered to be superior to S antigen vaccine or M antigen vaccine in terms of reduction in non-responders and/or acceleration of the onset.

Another major problem of the existing prophylactic vaccines is that they exert no effect on HBV escape variants. HBV escape variants refer to an HBV having a mutation in the antigenic determinant region "a" with a strong antigenic property of S antigen region. Antibodies produced against general S antigen vaccines have no preventive effect against such variants. Escape variants are assumed to be significantly increasing with the spread of antiviral drugs used for the treatment of hepatitis B. This will be a more serious problem in the future.

In contrast, M antigen vaccine, by producing an antibody against Pre-S2 region in addition to an antibody against S region, it ensures further stronger preventive effects against HBV variants than that of S antigen vaccine. And in the case of L antigen, since L antigen additionally produces anti-Pre-S1 antibody and mutants having mutations in the three regions may be rare, L antigen is assumed to be a further stronger protective vaccine against escape variants than M antigen vaccine. Therefore, L antigen vaccine is expected to be a prophylactic vaccine superior to the existing prophylactic vaccines that use S antigen or M antigen.

For the genotype of HBV, type A, type B, type C, type D, type E, type F, type G, and type H have been known. Recently, type I and type J are also known, in addition to these types (Non-Patent Literature 6). However, type A, type B, type C, and type D are the main genotypes of HBV. The relationship between genotype and phenotype has been clarified with regard to S region and Pre-S2 region. For example, in the S region, the 124th to 147th amino acid sequence is generally known as the antigenic determinant "a" having high immunogenicity. In the Pre-S2 region, it is known that the antigenic determinant "b" is present commonly in all genotypes (Non-Patent Literature 7). Therefore, even when the genotypes are varied, common antibodies are believed to be produced in these regions, in at least some genotypes.

With regard to Pre-S1 region, genotype and phenotype have not been sufficiently analyzed, and amino acid sequence homology between the respective genotypes of HBV is low. Therefore, it is considered that even when a vaccine containing, as an active ingredient, an L antigen containing a Pre-S1 region derived from a certain kind of genotype is produced, it is not always possible to trigger an immune reaction against HBV having a genotype of a different kind via the Pre-S1 region. Furthermore, the prevention of infection to the extent required as a prophylactic vaccine cannot be expected with certainty.

Anti-Pre-S1 antibody is known to have a preventive effect against HBV infection; the effect has been confirmed by an HBV infection test using chimpanzees (Non-Patent Literature 8). However, there are reports that although the anti-Pre-S1 antibody used in Non-Patent Document 8 is capable of protecting chimpanzees from infection by HBV having adw phenotype, it is incapable of protecting them from infection by HBV having ayw phenotype. Furthermore, Non-Patent Document 8 discloses that although this antibody is effective for genotypes A, B, C, F, and H of HBV, it presumably has no effects on genotypes D, E, and G, as a result of epitope analysis of anti-Pre-S1 antibody and the relationship in the amino acid sequence with Pre-S1 region. Further, there also are reports that another anti-Pre-S1 antibody, which showed an infection-inhibiting effect in chimpanzees, bound to a peptide of a Pre-S1 region synthesized based on the gene sequences of 12 kinds of HBV stored in the GenBank database at the time; but that, however, the binding failed when one amino acid of the epitope of the Pre-S1 region bound to the antibody was replaced (Non-Patent Literature 9).

As described above, although L antigen is excellent as a prophylactic vaccine, it is necessary to deal with the difference in genotype. In addition, the vaccine containing L protein (Sci-B-Vac) described above was made with no ingenuity, in view of the difference in genotype of Pre-S1 region contained in L protein; therefore, the vaccine cannot be considered to serve as a prophylactic vaccine that exerts an infection preventive effect against many (two or more) kinds of) genotypes of HBV.

It has been known that the administration of antiviral drugs, interferons, etc., is effective for the treatment of hepatitis B. However, antiviral agents have a problem in that their effects are not continuous, and therefore induce more escape variants for HBV. Further, interferon has a drawback of relatively weak therapeutic effects and a considerable number of side effects. Moreover, all of the above therapeutic agents have little effect of eliminating HBV from patients; therefore, a complete cure from HBV infection cannot be expected from these agents. Under such circumstances, the development of various therapeutic vaccines for hepatitis B has proceeded (Non-Patent Literature 10 to 14).

The fundamental component of a therapeutic vaccine is the HBV surface antigen and a core antigen (C antigen) which forms the capsid, and aims to eliminate HBV from infected cells mainly by triggering infection-preventing effects by humoral immunity and triggering cell-mediated immune activity. There is a report such that an immune reaction including cell-mediated immunity was increased without any safety problems in a clinical test in which a mixture of S antigen and C antigen was administered (Non-Patent Literature 13). Further, it has been revealed that a mixture of S antigen and C antigen had an effect superior to that of pegylated interferon in a comparative clinical test using a mixture of two antigens of the same type (Non-Patent Literature 10). Furthermore, Non-Patent Literature 14 reports that NK cells are involved in the elimination of HBV.

As described above, the development of therapeutic vaccines for chronic hepatitis B has proceeded in various ways. One of the working mechanisms of therapeutic vaccines is prevention of HBV infection by antibodies. Therefore, the characteristics required for the prophylactic vaccine described above are also required for therapeutic vaccines. More specifically, it is also preferable to use an L antigen containing Pre-S1 region as a therapeutic vaccine, rather than use an S antigen. In fact, a method using a surface antigen containing Pre-S1 region as a prophylactic vaccine having superior effects has been disclosed (Patent Literature 1, Non-Patent Literature 15). However, even with these methods, it is not possible to solve the problem of difference in genotypes of HBV described above, and it cannot be said that an appropriate therapeutic vaccine can be provided.

CITATION LIST

Patent Literature

Patent Literature 1: JP2010-516807

Non-Patent Literature

Non-Patent Literature 1: Yan et al. (2012) elife, 2012 Nov 13; 1: e00049

Non-Patent Literature 2: Iwamoto et al. (2014) BBRC, 443, 808-813

Non-Patent Literature 3: Shouval D et al. (2015) Med. Microbiol. Immunol., 204: 57-68

Non-Patent Literature 4: Soulie J C et al. (1991) Vaccine, 9: 545-548

Non-Patent Literature 5: Suzuki H et al. (1994) Vaccine, 12, 1090-1096

Non-Patent Literature 6: Sunbul M (2014) World J. Gastroenterol. 20 (18), 5427-5434

Non-Patent Literature 7: Usuda S et al. (1999) J. Virol. Methods. 80 (1), 97-112

Non-Patent Literature 8: Zhang P et al. (2006) Proc. Natl. Acad. Sci. USA, 103, 9214-9219

Non-Patent Literature 9: Hong H J et al. (2004) Virology, 318, 134-141

Non-Patent Literature 10: Akbar S M et al. (2016) Ann. Transl. Med., 4 (18), 335

Non-Patent Literature 11: Li J et al. (2015) Vaccine, 33, 4247-4254

Non-Patent Literature 12: Kosinska A D et al. (2015). Med. Microbiol. Immunol, 204, 103-104

Non-Patent Literature 13: Al-Mahtab M et al. (2013) Hepatol. Int., 7, 981-989

Non-Patent Literature 14: Tong S et al. (2017) Sci. Rep. 7: 314

Non-Patent Literature 15: Yum J S et al. (2012) Clin. Vaccine Immunol. 19, 120-127

Non-Patent Literature 16: Diminsky et al. (2000) Vaccine 18, 3-17

SUMMARY OF INVENTION

Technical Problem

In light of the above prior art, an object of the present invention is to provide an antigen that triggers an immune reaction against HBV of various (several or more) genotypes. Further, another object of the present invention is to provide a vaccine for preventing or treating hepatitis B caused by the infection of HBV of various (several or more) genotypes.

Solution to Problem

The inventors of the present invention carried out extensive research, and found that immune reactions against various (several or more) genotypes can be generated by using a virus-like particle containing HBs-L antigen protein derived from a specific genotype. The inventors also found that immune reactions against various (several or more) HBV genotypes can also be generated by using a virus-like particle composition containing a combination of virus-like particles containing HBs-L antigen protein derived from specific genotypes. Furthermore, the inventors also clarified that the virus-like particle and the virus-like particle composition described above have neutralization activity with respect to various (several or more) HBV genotypes. The present invention was accomplished based on the above findings, and broadly includes the following embodiments.

Item 1. A virus-like particle for use in generation of an immune reaction against several or more genotypes of HBV, the virus-like particle comprising a single kind of HBs-L antigen protein, the HBs-L antigen protein having a genotype of A, B, D, E, F, G, H, or a variant thereof.

Item 2. A virus-like particle for use in generation of an immune reaction against several genotypes of HBV, the virus-like particle comprising two or more kinds of HBs-L antigen protein, the HBs-L antigen protein having a genotype selected from the group consisting of A, B, C, D, E, F, G, H, and variants thereof.

Item 3. The virus-like particle according to item 1 or 2, wherein the immune reaction is humoral immunity or cell-mediated immunity.

Item 4. A virus-like particle composition, comprising a virus-like particle consisting of, as an HBs-L antigen protein, an HBs-L antigen protein of genotype C or a variant thereof; and the virus-like particle according to item 1.

Item 5. A virus-like particle composition, comprising at least two kinds of the virus-like particles according to items 1 to 3.

Item 6. A virus-like particle composition, comprising a virus-like particle consisting of, as an HBs-L antigen protein, an HBs-L antigen protein of genotype C or a variant thereof; and the virus-like particle composition according to item 5.

Item 7. The virus-like particle or the virus-like particle composition according to any one of items 1 to 6, wherein the HBs-L antigen protein of genotype A has an amino acid sequence represented by any one of SEQ ID NOs: 1 to 9; the HBs-L antigen protein of genotype B has an amino acid sequence represented by any one of SEQ ID NOs: 10 to 18; the HBs-L antigen protein of genotype C has an amino acid sequence represented by any one of SEQ ID NOs: 19 to 28; the HBs-L antigen protein of genotype D has an amino acid sequence represented by any one of SEQ ID NOs: 29 to 38; the HBs-L antigen protein of genotype E has an amino acid sequence represented by any one of SEQ ID NOs: 39 to 42; the HBs-L antigen protein of genotype F has an amino acid sequence represented by any one of SEQ ID NOs: 43 to 47; the HBs-L antigen protein of genotype G has an amino acid sequence represented by any one of SEQ ID NOs: 48 to 53; and the HBs-L antigen protein of genotype H has an amino acid sequence represented by any one of SEQ ID NOs: 54 to 57.

Item 8. A virus-like particle composition comprising the virus-like particle or the virus-like particle composition according to any one of items 1 to 7; and a virus-like particle comprising an HBV core antigen.

Item 9. A vaccine for the treatment and/or prevention of hepatitis B, comprising the virus-like particle or the virus-like particle composition according to any one of items 1 to 8.

Advantageous Effects of Invention

The virus-like particle or the virus-like particle composition of the present invention is capable of triggering an immune reaction against several genotypes of HBV. The virus-like particle or the virus-like particle composition of the present invention may be used as a vaccine for preventing hepatitis B infection, or as a vaccine for treating the same.

BRIEF DESCRIPTION OF DRAWINGS

In FIG. 2, Pre-S1 means Pre-S1 region, Trx means thioredoxin, lacI means Lac repressor gene, ori means *E. coli* replication origin, and Amp R means ampicillin-resistant gene.

In FIG. 4, GLDp means GLD promoter; MC means M antigen gene (Genotype C); PGKt means PGK terminator; Leu2 means Lue2 gene; and ori and Amp R are as defined above.

In FIG. 7, Sac I means Sac I site; His4 means His4 gene; Leu2 means Lue2 gene; 2micron means yeast 2micron sequence; and GLDp, PGKt, ori, and Amp R are as defined above.

In FIG. 8, LA, LB, and LD are L antigen gene (Genotypes A, B, and D); and GLDp, PGKt, ori, Amp R, Leu2, and 2micron are as defined above.

In FIG. 10, pr means promoter; LC means L antigen gene (Genotype C); Term means terminator; URA3 means Ura3 gene; and ori and Amp R are as defined above.

In FIG. 11, pr, LC, Term, ori, Amp R, and Lue2 are as defined above.

In FIG. 16, the vertical axis of each graph denotes the degree (relative value) of the binding between each antiserum and each Pre-S1, and the horizontal axis of each graph denotes the same as that in FIG. 14.

In FIG. 19, pr, LD, Term, ori, Amp R, and His4 are as defined above.

In FIG. 20, pr, LD, Term, ori, Amp R, and Ura3 are as defined above.

FIG. 22 shows a schematic diagram of the Lh1 antigen produced in Example 12.

FIG. 23 shows the pGLD-His4-LD2 constructed in Example 13. In FIG. 23, LD2 means LD2 antigen gene (Genotype D PreS-1+Genotype C PreS-2 and S); and GLDp, PGKt, His4, ori, Amp R, Leu2, and 2micron are as defined above.

In FIG. 25, pr, LA, Term, ori, Amp R, and Lue2 are as defined above.

In FIG. 27, pr, LB, Term, ori, Amp R, and Lue2 are as defined above.

FIG. 30 shows the results of the test in Example 17. Lh in FIG. 30 shows immunization with Lh1 antigen.

In FIG. 34, HBcAg means C antigen gene; and lacl, ori, and Amp R are as defined above.

In FIG. 36, the vehicle in the horizontal axis in each graph denotes negative control, Lh10 denotes Lh1 antigen, C10 denotes C antigen, Lh+C10 denotes Lh1 and C antigen, and ConA10 denotes stimulation to spleen cells by concanavalin A.

Figure 1:
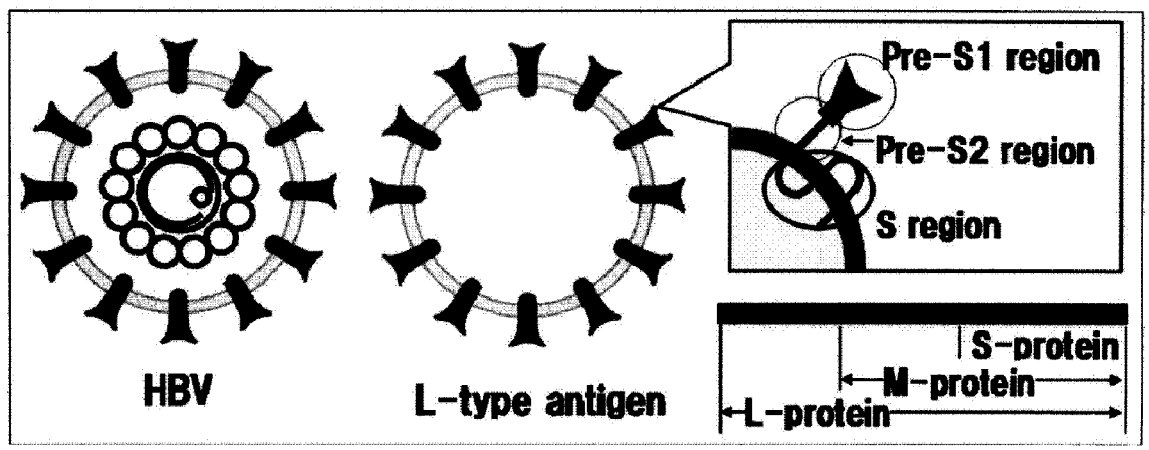
FIG. 1 is a schematic diagram showing a structure of HBV and L-type HBV surface antigen.
Figure 2:
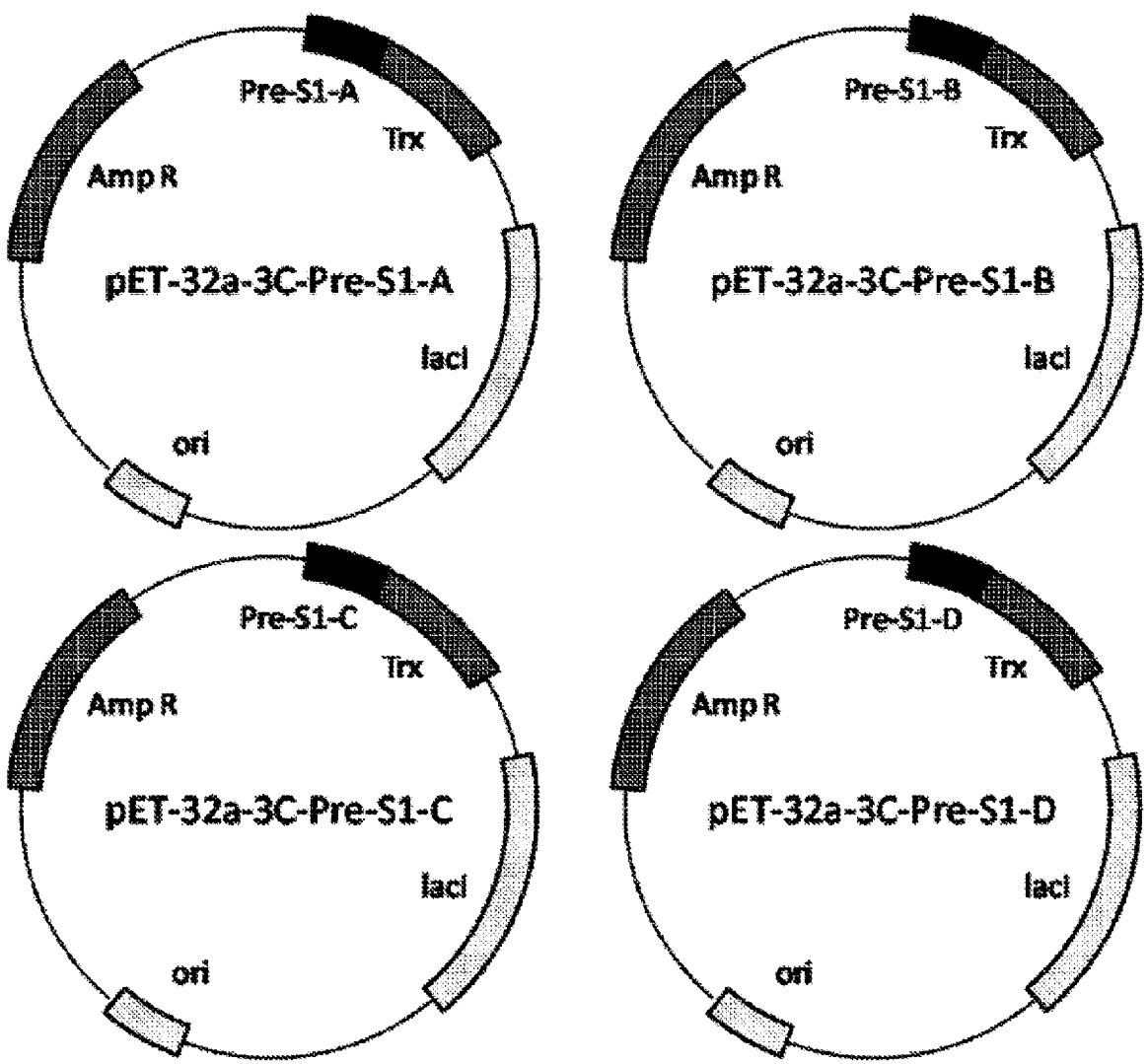
FIG. 2 shows the pET32a-3C-Pre-S1-A, pET32a-3C-Pre-S1-B, pET32a-3C-Pre-S1-C, and pET32a-3C-Pre-S1-D constructed in Example 1.
Figure 3:
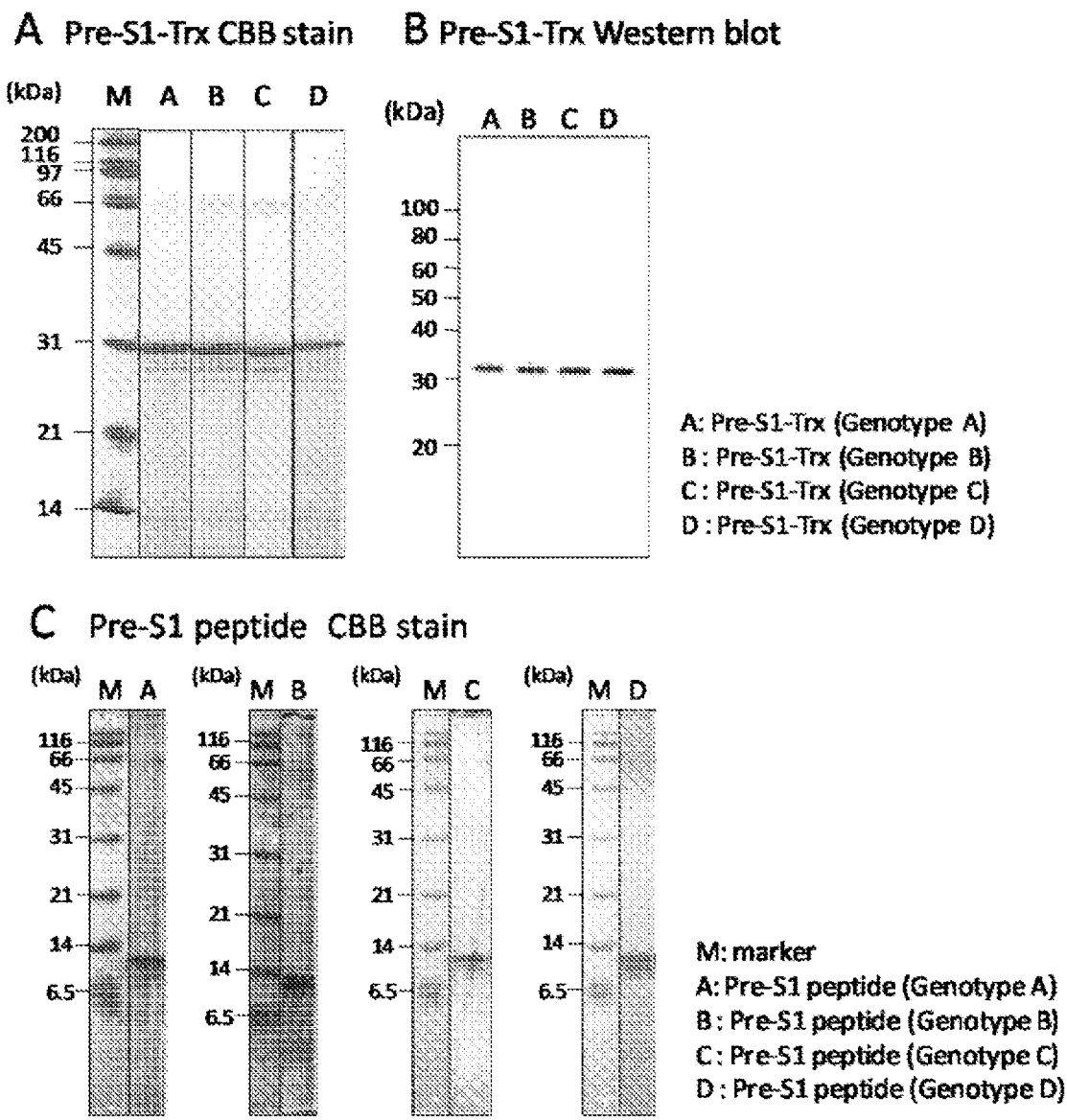
FIG. 3 shows the results of analysis of Pre-S1-Trx and Pre-S1 peptide of each genotype produced in Example 1.
Figure 4:
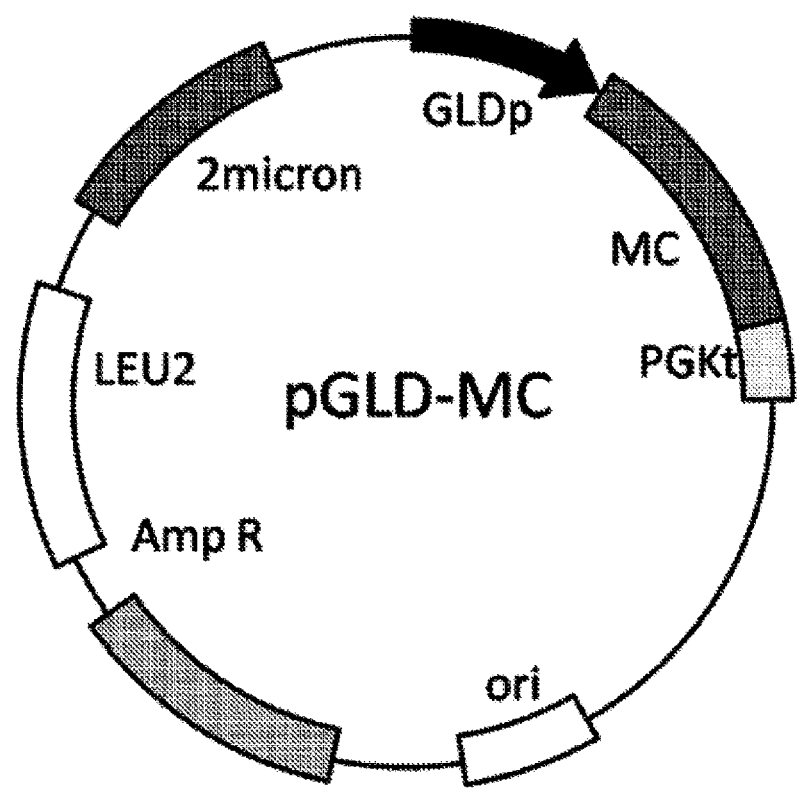
FIG. 4 shows the pGLD-MC constructed in Example 2.

In this specification, the meaning of the term "comprise" or "contain" includes both "consist essentially of" and "consist of."

Virus-Like Particle

The virus-like particle of the present invention may be used to trigger an immune reaction against several genotypes of HBV. HBV genotype means a group of HBV made to distinguish HBV variants. A different genotype means having more than 8% difference in HBV gene sequence. In the future, the number of genotypes may increase. Therefore, there is no particular limitation of genotype, insofar as it has been properly confirmed. The identity between the amino acid sequences of HBV of the individual genotypes thus distinguished from each other is about 92% or more. Specific examples of HBV genotypes include A, B, C, D, E, F, G, H, I, and J. The expression "HBs-L antigen protein of genotype A" in this specification means an "HBs-L antigen protein derived from HBV of genotype A." The same is true for the description of HBs-L antigen proteins of other genotypes, i.e., genotypes B to J.

The immune reaction triggered by the virus-like particle of the present invention is not particularly limited, insofar as it is an immune reaction triggered upon the administration of the virus-like particle to an organism. Examples of the immune reaction include humoral immune reaction, cell-mediated immune reaction, and the like.

The virus-like particle of the present invention comprises one or more HBs-L antigen protein. The virus-like particle of the present invention is classified into two embodiments depending on whether the virus-like particle comprises a single genotype of HBs-L antigen protein, or multiple genotypes of HBs-L antigen proteins.

The virus-like particle according to the first embodiment is a virus-like particle comprising an HBs-L antigen protein of a single kind. The HBs-L antigen protein contained in the virus-like particle of the first embodiment is an HBs-L antigen protein of a single genotype, except for the variants described later. The virus-like particle of the first embodiment is capable of triggering an immune reaction against several genotypes of HBV. The number of types of the HBV genotypes for which the virus-like particle of the first embodiment can trigger an immune reaction is not particularly limited. The larger the number of genotypes, the better. For example, at least two genotypes are preferable; further, at least three genotypes, or at least four genotypes, are more preferable.

The virus-like particle according to the second embodiment is a virus-like particle comprising HBs-L antigen proteins of two or more genotypes. The virus-like particle of the second embodiment is also capable of triggering an immune reaction against several genotypes of HBV. The number of HBV genotypes for which the virus-like particle of the second embodiment can generate an immune reaction is also not particularly limited. The larger the number of genotypes, the better. For example, when HBs-L antigen proteins of two or more genotypes are contained in the virus-like particle of the second embodiment, the virus-like particle preferably generates an immune reaction against three or more, more preferably four or more, genotypes of HBV. Thus, the second virus-like particle is capable of generating an immune reaction against HBV of a larger number of genotypes than the number of genes of the HBs-L antigen proteins contained therein.

As described in the examples described below, the virus-like particle of the second embodiment containing HBs-L antigen of genotype C and HBs-L antigen of genotype D can trigger an immune reaction against not only the genotype C or D, but also HBV of other genotypes, i.e., genotype A or B. The virus-like particles according to the two embodiments described above are described below in detail.

(1) Virus-Like Particle of First Embodiment

The virus-like particle according to the first embodiment is a virus-like particle comprising an HBs-L antigen protein of a single genotype. The virus-like particle of the first embodiment comprises one, or two or more HBs-L antigen proteins. The virus-like particle of the first embodiment is a particle that comprises, as major components, an HBs-L antigen protein or proteins having one, or two or more transmembrane domains; as well as a lipid bilayer membrane. The virus-like particle of the first embodiment does not have nucleic acid such as DNA or RNA that controls genetic information in the particle.

The genotype of the HBs-L antigen protein contained in the virus-like particle of the first embodiment of the present invention is one kind from among A, B, D, E, F, G, H, and J. Further, the variants of these genotypes are also encompassed in the range of HBs-L antigen proteins contained in the virus-like particles of the first embodiment. The variants defined in this specification are not limited to variants that resulted from spontaneous mutation, but also include variants obtained by artificially introducing mutations.

The amino acid sequence of the HBs-L antigen protein of each specific genotype is not particularly limited. For example, genotype A may have an amino acid sequence represented by any one of SEQ ID NOs: 1 to 9; genotype B may have an amino acid sequence represented by any one of SEQ ID NOs: 10 to 18; genotype D may have an amino acid sequence represented by any one of SEQ ID NOs: 29 to 38; genotype E may have an amino acid sequence represented by any one of SEQ ID NOs: 39 to 42; genotype F may have an amino acid sequence represented by any one of SEQ ID NOs: 43 to 47; genotype G may have an amino acid sequence represented by any one of SEQ ID NOs: 48 to 53; and genotype H may have an amino acid sequence represented by any one of SEQ ID NOs: 54 to 57.

The amino acid sequence that specifies the HBs-L antigen protein of each genotype described above can also be a variant of any amino acid sequence represented by SEQ ID NOs: 1 to 57 that specify the HBs-L antigen proteins of the individual genotypes, insofar as the effects of the present invention are not significantly impaired. The mutation is not particularly limited. Examples of the mutation include substitutions, insertions, and deletions.

The degree of the mutation of the amino acid sequence of each genotype described above is not particularly limited. Examples of the degree of mutation include introduction of mutation of about 33 amino acids into an amino acid sequence represented by any one of SEQ ID NOs: 1 to 9 (genotype A); introduction of mutation of about 26 amino acids into an amino acid sequence represented by any one of SEQ ID NOs: 10 to 18 (genotype B); introduction of mutation of about 38 amino acids into an amino acid sequence represented by any one of SEQ ID NOs: 29 to 38 (genotype D); introduction of mutation of about 21 amino acids into an amino acid sequence represented by any one of SEQ ID NOs: 39 to 42 (genotype E); introduction of mutation of about 16 amino acids into an amino acid sequence represented by any one of SEQ ID NOs: 43 to 47 (genotype F); introduction of mutation of about 9 amino acids into an amino acid sequence represented by any one of SEQ ID NOs: 48 to 53 (genotype G); and introduction of mutation of about 27 amino acids into an amino acid sequence represented by any one of SEQ ID NOs: 54 to 57 (genotype H).

The degree of mutation introduction into the amino acid sequence of each genotype defined in the present invention was determined by analyzing each amino acid sequence obtained from a database such as NCBI (National Center for Biotechnology Information) using gene analysis software. Genotypes A to D were analyzed using 20 different amino acid sequences, genotype E was analyzed using 10 different amino acid sequences, genotype F was analyzed using 8 amino acid sequences, and genotypes G and H were analyzed using 7 different amino acid sequences.

When the number of amino acids of SEQ ID NOs: 1 to 57 is 400, examples of the variants described above include: variants in which the region of 11 amino acids from the N-terminal and/or the region of 6 amino acids from 163rd to 168th amino acids are deleted. Further, when the number of amino acids of SEQ ID NOs: 1 to 57 is not 400, examples of the variants include variants in which the amino acid sequences in these regions are deleted.

Examples of variants obtained by artificial mutation introduction include variants obtained by substitution or deletion of Pre-S1 region, Pre-S2 region, and S region, which are 3 regions of HBs-L antigen protein, into regions derived from different genotypes. More specifically, examples of variants include those obtained by substitution of Pre-S1 region of a certain genotype with Pre-S1 region derived from another genotype; substitution of Pre-S1 and Pre-S2 regions of a certain genotype with Pre-S1 and Pre-S2 regions derived from another genotype; and substitution of Pre-S2 region of a certain genotype with Pre-S2 region derived from another genotype. It is also possible to substitute a Pre-S2 region with a Pre-S1 region derived from another genotype. Examples also include variants obtained by deletion of Pre-S2 region. In these artificial substitutions, it is possible to introduce mutations of a larger number than the number of mutations introduced into the amino acid sequence of each genotype described above.

(2) Virus-Like Particle of Second Embodiment

The virus-like particle according to the second embodiment is a virus-like particle comprising HBs-L antigen proteins of two or more genotypes. The virus-like particle of the second embodiment comprises one, or two or more HBs-L antigen proteins. The virus-like particle of the second embodiment is also a particle that comprises, as major components, HBs-L antigen proteins having one, or two or more transmembrane domains; as well as a lipid bilayer membrane. The virus-like particle does not have nucleic acid such as DNA or RNA that controls genetic information in the particle.

The genotypes of the HBs-L antigen proteins contained in the virus-like particle of the second embodiment is two or more genotypes selected from the group consisting of A, B, C, D, E, F, G, H, I, and J. Further, the variants of these genotypes are also encompassed in the range of HBs-L antigen proteins contained in the virus-like particle of the second embodiment. The amino acid sequence of the HBs-L antigen protein of each specific genotype and variants thereof are not particularly limited. For example, they may be similar to those of the virus-like particle of the first embodiment. Examples of HBs-L antigen protein of genotype C include amino acid sequences according to any one of SEQ ID NOs: 19 to 28. Further, it is possible to introduce mutation of about 28 amino acids into an amino acid sequence represented by any one of SEQ ID NOs: 19 to 28.

Preferred embodiments of the HBs-L antigen proteins of two or more genotypes contained in the virus-like particle of the second embodiment can be determined according to the identity of the amino acid sequences in the various presumptive epitope with respect to the Pre-S1 region of HBV of each genotype. Since the Pre-S1 region has low amino acid sequence identity among respective HBV genotypes, finding a combination in which the amino acid sequences of the presumptive epitopes in this region are almost identical can be important information for determining a preferred embodiment of a virus-like particle that can be used to trigger an immune reaction against HBV of several genotypes.

Table 1 below shows the results obtained by assuming different amino acid sequence regions (indicated by single letters) among the genotypes as presumptive epitopes in the representative amino acid sequences of genotypes A, B, C, D, E, and F. The amino acids shown in bold letters in the table are two or more continuous common amino acid residues in the presumptive epitopes of two or more genotypes.

TABLE 1

|  |  | presumptive epitope | | | | | |
| --- | --- | --- | --- | --- | --- | --- | --- |
|  |  | a | b | c | d | e | f |
| Genotype of HBV | A | kgmgtnlsvp | afgansnn | hwpqanq | fgpgftpp | gilatvpam | qsgrqptpis |
|  | B | kgmgtnlsvp | afkansen afkansdn | nwpdahk | fgpgftpp | giltsvpaa | qsgrqptpls |
|  | C | qgmgtnlsvp | afgansnn | hwpeanq | fgpgftpp | gilttvpaa | qsgrqptpis |
|  | D | --mgqtnlsts-- | afrantan | swpdank | fglgftpp | gilqtlpan giletlpan gilqtvpan gihtvpan giiqtlpan | qsgrqptpls qtgrqptpls |
|  | E | lewgknistt | afrantrn | hwteank | fgpgftpp | gmlktlpad | qsgrqptpit |
|  | F | rgmqnlsvp | lfransss | swpmank twpmank | ygpgftpp | gvltvlpad | rsgrkptpvs lsgrkptqvs |

The table shows that, for example, the amino acid sequences of the presumptive epitopes of genotypes A, B, and C have many common parts. The table also shows that the amino acid sequences in the presumptive epitopes of genotype D considerably differ from those of genotypes A, B, and C; however, they have many common parts with respect to the amino acids of genotypes E and F. Therefore, it is assumed that the virus-like particle of the second embodiment preferably comprises, as the HBs-L antigen protein, one of the HBs-L antigen proteins of genotype A, genotype B, and genotype C; and, as other HBs-L antigen proteins, the HBs-L antigen proteins of genotypes D and/or E.

A virus-like particle comprising a single kind of HBs-L antigen protein, which is an HBs-L antigen protein consisting of an amino acid sequence represented by any one of SEQ ID NOs: 19 to 28, or an amino acid sequence of a variant thereof, is clearly excluded from the range of the virus-like particle of the present invention. The variant of the amino acid sequence represented by any one of SEQ ID NOs: 19 to 28 means a variant consisting of an amino acid sequence in which about 28 amino acids are introduced into the amino acid sequence of any one of SEQ ID NOs: 19 to 28.

The virus-like particle of the present invention described above may comprise other components in addition to the HBs-L antigen protein(s), insofar as the effects of the present invention are not significantly impaired. The other components are not particularly limited. Specifically, examples of other components include antigen proteins other than the HBV-derived HBs-L antigen proteins. The other antigen proteins are not particularly limited. Specifically, examples of other antigen proteins include HBV-derived S antigen protein, M antigen protein, core antigen protein, and the like. Among them, S antigen protein, core antigen protein, or variants thereof are preferable. Since core antigens are known to have a plurality of epitopes that trigger an immune reaction, examples of the variants thereof include those having one or more of the epitopes described above. The genotypes of the antigen proteins other than the HBV-derived HBs-L antigen proteins are not particularly limited. For example, similarly to the HBs-L antigen protein contained in the virus-like particle the present invention, the other proteins may also be derived from genotypes A, B, C, D, E, F, G, H, I, and J. The genotype of the HBs-L antigen protein contained in the virus-like particle of the present invention described above and the genotype of the antigen protein other than the HBs-L antigen protein contained therein may be the same or different.

The method for producing the virus-like particle of the present invention described above is not particularly limited. More specifically, the virus-like particle of the present invention can easily be produced by a biotechnological means capable of transforming the host cells using a nucleic acid comprising a base sequence encoding the HBs-L antigen protein contained in the virus-like particle, and breeding the transformant in an appropriate medium. The host cells are not particularly limited. Examples include eukaryotic cells. Yeast cells or CHO cells are particularly preferable. In particular, yeast cells are preferable. The nucleic acid comprising a base sequence encoding the HBs-L antigen protein described above may also be used for the transformation of the host cells in the state of a plasmid, or may be incorporated into the genomic DNA of the host cells in a linear state.

Virus-Like Particle Composition

The present invention also encompasses a virus-like particle composition comprising a combination of virus-like particles that can be used to trigger an immune reaction against HBV of two or more genotypes described above. This virus-like particle composition may also be used to trigger an immune reaction against several genotypes of HBV. Examples of the virus-like particle composition include the following four embodiments.

(1) Virus-Like Particle Composition of First Embodiment

The virus-like particle composition according to the first embodiment of the present invention is a virus-like particle composition comprising one kind of the virus-like particle of the first embodiment; and a virus-like particle consisting only of, as an HBs-L antigen protein, an HBs-L antigen protein of genotype C or a variant thereof (this particle may be referred to as "particle C" in this specification).

Specific examples of the virus-like particle composition of the first embodiment include a virus-like particle composition comprising a virus-like particle of the first embodiment consisting only of an HBs-L antigen protein of genotype D as an HBs-L antigen protein, and particle C. As described in the explanation of the virus-like particle according to the second embodiment of the present invention, the HBs-L antigen protein of genotype C or a variant thereof is preferably used in combination with the HBs-L antigen protein of genotype D.

The amino acid sequence of the HBs-L antigen protein of genotype C contained in particle C is not particularly limited. Examples include an amino acid sequence represented by any one of SEQ ID NOs: 19 to 28. The variant of the HBs-L antigen protein of genotype C described above is not particularly limited. Specific examples include variants of amino acid sequences represented by any one of SEQ ID NOs: 19 to 28, which are HBs-L antigen proteins of genotype C. Such mutation introduction is not particularly limited. Examples of mutations include substitutions, insertions, and deletions. The degree of the mutation of the HBs-L antigen protein of genotype C is not particularly limited, insofar as the effects of the present invention are not significantly impaired. Specifically, it is possible to introduce mutation of about 28 amino acids into an amino acid sequence represented by any one of SEQ ID NOs: 19 to 28.

The content ratio of particle C in the virus-like particle composition of the first embodiment is not particularly limited. Generally, the content ratio may be set within a range in which the effects of the present invention are not significantly impaired.

(2) Virus-Like Particle Composition of Second Embodiment

The virus-like particle composition according to the second embodiment of the present invention is a virus-like particle composition comprising a mixture of a plurality of virus-like particles of the first embodiment. The genotypes of the HBs-L antigen proteins contained in the virus-like particles of the first embodiment contained in the virus-like particle composition of the second embodiment may vary.

Examples include a virus-like particle composition comprising a mixture of a virus-like particle consisting only of an HBs-L antigen protein of genotype A as an HBs-L antigen protein, and a virus-like particle consisting only of an HBs-L antigen protein of genotype B as an HBs-L antigen protein.

The number of genotypes of HBs-L antigen protein contained in the virus-like particle composition of the second embodiment is not particularly limited. For example, the number of genotypes may be 2, 3, 4, 5, 6, 7, 8, 9, or 10. The content ratio of the virus-like particle of the first embodiment in the virus-like particle composition of the second embodiment is not particularly limited. Generally, the content ratio may be set within a range in which the effects of the present invention are not significantly impaired.

The virus-like particle composition of the second embodiment may comprise particle C. The content ratio of particle C in the virus-like particle composition of the second embodiment is not particularly limited. Generally, the content ratio may be set within a range in which the effects of the present invention are not significantly impaired. The specific amino acid sequences of the HBs-L antigen protein of genotype C and variants thereof contained in particle C may be similar to those of the virus-like particle composition according to the first embodiment.

(3) Virus-Like Particle Composition of Third Embodiment

The virus-like particle composition according to the third embodiment of the present invention is a virus-like particle composition comprising a mixture of a plurality of virus-like particles of the second embodiment. The genotypes of the HBs-L antigen proteins contained in the virus-like particles contained in the virus-like particle composition of the third embodiment may vary.

Examples include a virus-like particle composition comprising a virus-like particle consisting only of an HBs-L antigen protein of genotype A and an HBs-L antigen protein of genotype B as HBs-L antigen proteins; and a virus-like particle consisting only of an HBs-L antigen protein of genotype C and an HBs-L antigen protein of genotype D as HBs-L antigen proteins.

The number of genotypes of HBs-L antigen proteins contained in the virus-like particle composition of the third embodiment is not particularly limited. For example, the number of genotypes may be 2, 3, 4, 5, 6, 7, 8, 9, or 10. The content ratio of each of the virus-like particles of the second embodiment in the virus-like particle composition of the third embodiment is not particularly limited. Generally, the content ratio may be set within a range in which the effects of the invention are not significantly impaired.

The virus-like particle composition of the third embodiment may comprise particle C. The content ratio of particle C in the virus-like particle composition of the third embodiment is similar to those of the virus-like particle composition of the second embodiment. The specific amino acid sequences of the HBs-L antigen protein of genotype C or variants thereof contained in particle C may be similar to that of the virus-like particle composition according to the first embodiment.

(4) Virus-Like Particle Composition of Fourth Embodiment

The virus-like particle composition according to the fourth embodiment of the present invention is a virus-like particle composition comprising a virus-like particle of the first embodiment and a virus-like particle of the second embodiment described above. HBs-L antigen proteins of the same genotypes may be contained in each of the virus-like particles contained in the virus-like particle composition of the fourth embodiment.

Examples include a virus-like particle composition comprising a virus-like particle of the first embodiment consisting only of an HBs-L antigen protein of genotype A as an HBs-L antigen protein, and a virus-like particle of the second embodiment consisting only of an HBs-L antigen protein of genotype A and an HBs-L antigen protein of genotype C as HBs-L antigen proteins.

The number of genotypes of HBs-L antigen protein contained in the virus-like particle composition of the fourth embodiment is not particularly limited. For example, the number of genotypes may be 2, 3, 4, 5, 6, 7, 8, 9, or 10. The content ratios of the virus-like particle of the first embodiment and the virus-like particle of the second embodiment in the virus-like particle composition of fourth embodiment are not particularly limited. Generally, the content ratio may be set within a range in which the effects of the present invention are not significantly impaired.

The virus-like particle composition of the fourth embodiment may comprise particle C. The content ratio of particle C in the virus-like particle composition of the fourth embodiment is similar to that of the virus-like particle composition of the second embodiment. The specific amino acid sequences of the HBs-L antigen protein of genotype C or variants thereof contained in particle C may be similar to those of the virus-like particle composition according to the first embodiment.

The virus-like particles or the virus-like particle compositions of the present invention described above may also comprise a virus-like particle comprising HBV core antigen and variants thereof. Since a virus-like particle containing HBV core antigen is known to easily trigger cell-mediated immunity against HBV, a virus-like particle composition obtained by incorporating such a virus-like particle is more likely to trigger an immune reaction against HBV of several genotypes. The amount of the virus-like particle containing HBV core antigen to be mixed with the virus-like particle or the virus-like particle composition of the present invention is not particularly limited. Generally, an appropriate amount can be set within a range in which an immune reaction against HBV of several or more genotypes can be triggered.

Since the virus-like particles or the virus-like particle compositions of the present invention are expected to be used to trigger an immune reaction against HBV of several genotypes, the virus-like particles and the virus-like particle compositions of the present invention may be used as a vaccine against HBV (a vaccine for preventing or treating HBV).

Vaccine for Preventing or Treating HBV

The vaccine for preventing and/or treating HBV of the present invention comprises the virus-like particles or the virus-like particle compositions described above. The amount of each virus-like particle or the virus-like particle composition contained in the vaccine for preventing and/or treating HBV of the present invention is not particularly limited. For example, the amount is generally about 0.0001 to 100 mass % per vaccine for preventing and/or treating HBV.

Known pharmaceutically acceptable carriers or additives for use in the production of compositions in the pharmaceutical field may be incorporated in the vaccine for preventing and/or treating HBV of the present invention. Such carriers and additives are not particularly limited. Examples of the carriers and additives include any arbitrary carriers, diluents, excipients, suspensions, lubricants, adjuvants, media, delivery systems, emulsifiers, tablet disintegrants, absorbents, preservatives, surfactants, coloring agents, flavors, sweeteners, and the like. Incorporation of adjuvants is particularly preferable.

The vaccine for preventing and/or treating HBV of the present invention may have any drug form as an appropriate combination with the carriers or additives described above. Examples of drug forms include injection agents such as infusions, implant injection agents, microneedles, or prolonged-release injections; dialysis agents such as peritoneal dialysis agents or hemodialysis agents; tablets such as oral disintegrating tablets, chewable tablets, effervescent tablets, dispersible tablets, or soluble tablets; capsules such as hard-capsule tablets or soft-capsule tablets; granules including effervescent granules, sustained-release granules, enteric granules, and the like; liquids and solutions for oral administration such as powders, elixirs, suspensions, emulsions, or lemonades; tablets for oro-mucosal application such as syrups, oral jellies, lozenges, sublingual tablets, buccal tablets, mucoadhesive tablets, or gums; inhalations such as oral sprays, semisolid oral agents, mouthwashes, inhalation powders, inhalation liquids, or inhalation aerosols; eye drops such as eye ointments; ear drops; nasal dry powder inhalers; nasal drops such as nasal sprays or nasal drops; solid preparations for external use such as suppositories, rectal semisolid agents, enemas, vaginal tablets, vaginal suppositories, or external powders; liquids for external use such as liniments or lotions; sprays such as aerosols for external use or pump sprays; and patches such as ointments, creams, gels, tapes, or cataplasms. These dosage forms can be produced based on publicly known documents such as The Japanese Pharmacopoeia, 16th edition.

The vaccine for preventing and/or treating HBV of the present invention may be administered to patients with these diseases, humans who are possibly affected with these diseases, humans who are regarded as requiring prevention of these diseases, and the like.

The method for administering the vaccine for preventing and/or treating HBV of the present invention is not particularly limited. For example, known administration methods can be used in appropriate consideration of the administration subject, drug form, or the like. Specific examples of administration methods include oral administration, intramuscular administration, intravenous administration, intraarterial administration, intrathecal administration, intradermal administration, intraperitoneal administration, intranasal administration, intrapulmonary administration, intraocular administration, intravaginal administration, intracervical administration, intrarectal administration, subcutaneous administration, and the like.

The administration amount of the vaccine for preventing and/or treating HBV of the present invention is not particularly limited. When the vaccine is administered to a human, the administration amount is generally about 0.001 to 20 µg/kg. The number of administrations of the therapeutic agent of the vaccine for preventing and/or treating HBV of the present invention is not particularly limited. For example, the therapeutic agent may be administered in the amount specified above once a day; or in several portions, within the range in which the therapeutic effects of the vaccine for preventing and/or treating HBV are ensured. The frequency of the administration of the therapeutic agent of the vaccine for preventing and/or treating HBV of the present invention is not particularly limited. The administration may be performed, for example, every day, every other day, every week, every two weeks, every 2 to 3 weeks, every month, every two months, or every 2 to 6 months.

EXAMPLES

Examples are shown below to explain the present invention in further detail. However, the scope of the invention is not limited to these Examples.

Example 1

Production of Pre-S1 Fusion Proteins of Genotypes A, B, C, and D; and Peptides Thereof

(1) Construction of Vector

The DNA sequences encoding Pre-S1 peptides of the respective genotypes were produced by PCR method based on the template shown in Table 2 below.

TABLE 2

| Genotype | template | origin | Sequence No |
|---|---|---|---|
| A | HBV compete genome clone Ae_US | Acc No. AB246337 | 9 |
| B | HBV complete genome clone Bj_JPN35 | Acc No. AB246341 | 12 |
| C | pGLD LIIP39-RcT | Reference 1 | 23 |
| D | PCEP-ayw | Acc No. U95551 | 37 |

"Acc" in the table means an NBCI accession number. Reference No 1 is a vector (pGLD LIIP39-RcT) disclosed in Kuroda et al., J. Biol. Chem., 1992, 267: 1953-1961; PMID: 137048; and U.S. Pat. No. 4,085,231.

The resulting four kinds of DNA fragments were inserted in pET-32a vector (Novagen). Next, a base sequence of SEQ ID NO: 59 that encodes the amino acid sequence of SEQ ID NO: 58, which is specifically cleaved by human rhinovirus 3C protease, was inserted immediately before the base sequence encoding the Pre-S1 peptide of each vector, thereby obtaining a vector. The vectors obtained were named pET-32a-3C-Pre-S1-A, pET-32a-3C-Pre-S1-B, pET-32a-3C-Pre-S1-C, and pET-32a-3C-Pre-S1-D, respectively (FIG. 2).

(2) Preparation of Pre-S1-TRX Fusion Protein and Pre-S1 Peptide using *Escherichia Coli*

*Escherichia coli* strain BL21 (DE3) pLysS was transformed using the vectors prepared in (1) above, thereby obtaining expression strains. Each expression strain was cultured under IPTG induction, and a Pre-S1-TRX fusion protein of each genotype was obtained from the resulting cell lysate using a Chelating Sepharose Fast Flow (GE Healthcare) column. Human rhinovirus 3C protease was added thereto, and Pre-S1 peptide and TRX protein of each genotype were separated and added to the column; and the resulting eluate was used as purified Pre-S1 peptide.

(3) Confirmation of Pre-S1-TRX Fusion Protein and Pre-S1 Peptide of Each Genotype The resulting Pre-S1-TRX fusion protein for each genotype was subjected to SDS-PAGE, followed by CBB staining. A band was observed at the position corresponding to a molecular weight of about 31 kDa (FIG. 3A). The Pre-S1-TRX fusion protein was subjected to western blotting (may hereinafter be referred to as "WB" in this specification) analysis using anti-Pre-S1 antibody (mouse monoclonal antibody, Beacle, Inc.; BCL-AB 001) and, as a secondary antibody, anti-mouse IgG-HRP (Rockland, 210-4302). As a result, a band was detected at the position corresponding to a molecular weight of about 31 kDa (FIG. 3B). These results confirmed the purification of the Pre-S1-TRX fusion protein of each genotype. Further, as a result of SDS electrophoresis of the purified Pre-S1 peptide, a band was observed at the position corresponding to a molecular weight of about 11 kDa (FIG. 3C). The result confirmed the purification of the Pre-S1-peptide of each target genotype.

Example 2

(1) Production of L Antigen and M Antigen Particles of Genotype C Using Plasmid-Type Expression Vector The antigen particle consisting of HBsAg-L antigen protein of genotype C (this protein may hereinafter be referred to as "Lc protein" in this specification) was prepared by the purification method disclosed in U.S. Pat. No. 4,936,272, using the vector disclosed in U.S. Pat. No. 4,085,231. The antigen protein contained in the particle thus obtained consists only of Lc protein. The particle may be referred to as "Lc antigen" in this specification. Further, the expression vector pGLD-MC shown in FIG. 4, which lacked the Pre-S1 region of LC gene, was produced, and an expression strain was prepared in the same method as that for Lc antigen. Then, the strain was cultured, and Mc antigen (M antigen particle) consisting of Mc antigen protein was purified from the cultured cells.

(2) Confirmation of Lc Antigen and Mc Antigen by Plasmid Expression

FIG. 5A shows the results of silver staining, which was performed after each Lc antigen obtained in (1) above was subjected to SDS-PAGE. With regard to the Lc protein (having a molecular weight of about 42 kDa), due to the influence of sugar chain modification, the band corresponding to the monomer was observed at a position slightly larger than 45 kDa, and the band corresponding to the dimer was observed around 97 kDa. Mc antigen was also analyzed by a similar method. As a result, as shown in FIG. 5C, the band corresponding to the monomer was observed around a molecular weight of about 32 kDa.

As a result of WB of the Lc antigen using an anti-S antibody (rabbit polyclonal antibody, Abcam, ab32916), anti-Pre-S1 antibody (Beacle, Inc.; BCL-AB-001), or anti-Pre-S2 antibody (Institute of Immunology, 2APS42), bands were detected at the monomer and dimer positions in all cases (FIG. 5B). The Mc antigen was also analyzed by a similar method. As a result, a band was detected at the monomer position in the cases of using anti-S antibody and the anti-Pre-S2 antibody, but was not detected in the case of using anti-Pre-S1 antibody (FIG. 5D). The secondary antibodies used in the WB were anti-rabbit IgG-HRP antibody (Santa Cruz, sc-2004) and anti-mouse IgG-HRP antibody (Rockland, 210-4302).

An antigen that has been used for the previously known Sci-B-Vac vaccine was obtained from SciGen, and SDS-PAGE was performed using Lc antigen as a control; thereafter, silver staining and WB were performed. FIG. 6 shows the results. The results of silver staining revealed that the Sci-B-Vac antigen is constituted of various proteins, presumably because of the differences due to sugar chain modification (the main bands are present around 24, 27, 33, 36, 39, and 42 kDa in molecular weight). The positions of these bands were highly consistent with the results disclosed in Non-Patent Literature 15, in which the proteins were expressed in the same manner as that for Sci-B-Vac antigen. As a result of WB, all of these bands were detected with respect to the anti-S antibody, but none were detected with respect to the anti-Pre-S1 antibody. The results above show that the Sci-B-Vac antigen hardly has Pre-S1; or, even if it has Pre-S1, the amount thereof is very small.

The above results indicate that the prepared Lc antigen is a particle constituted of an L protein having three regions, i.e., S region, Pre-S2 region, and Pre-S1 region; and is constituted of a monomer and a dimer. Further, it was also revealed that Mc antigen was constituted of S region and Pre-S2 region. As a result of particle size measurement using a dynamic light scattering method with a Zetasizer (Malvern Panalytical), it was confirmed that the particle size of the Lc antigen was about 59.7 nm, and the particle size of the Mc antigen was about 62.5 nm.

Example 3

Production of Plasmid-Type Expression Vector pGLD-His4

Based on the antigen-expressing plasmid pGLD-LIIP39-RcT (U.S. Pat. No. 4,085,231), the pGLD-His4 vector shown in FIG. 7 was produced. The His4 gene fragment was prepared from genomic DNA of NA87-11A strain of the budding yeast.

Example 4

(1) Production of L Antigen Particles of Genotypes A, B, and D Using Plasmid-Type Expression Vector The genes (these genes may be respectively referred to as "LA gene," "LB gene," and "LD gene" in this specification) encoding the L proteins of genotypes A, B, and D (these proteins may be respectively referred to as "La protein," "Lb protein," and "Ld protein" in this specification) were subjected to PCR using the templates shown in Table 2 above, thereby amplifying the genes.

The gene sequences corresponding to the six amino acid residues (LA: SISART; SEQ ID NO: 60, LB: SILSKT; SEQ ID NO: 61, and LD: SIFSRI; SEQ ID NO: 62) of the Pre-S2 region, which are highly likely to be subjected to degradation by the protease in the yeast, were deleted from the amplified LA, LB, and LD genes; further, the sequence corresponding to the signal peptide sequence disclosed in U.S. Pat. No. 4,085,231 was inserted into the 5' side of each gene, thereby producing the pGLD-His4-LA, pGLD-His4-LB, and pGLD-His4-LD shown in FIG. 8.

The particle consisting only of La protein as the antigen protein obtained by using pGLD-His4-LA may be referred to as "La antigen" in this specification. Similarly, the particle consisting only of Lb protein may be referred to as "Lb antigen," and the particle consisting only of "Ld protein" may be referred to as "Ld antigen" in this specification.

Yeasts (AH22R-, Lue2, and His4 variant strains) were transformed using the vectors described above; followed by screening by a predetermined method, thereby obtaining La, Lb, and LD antigen expression strains. The La, Lb, and Ld antigen particles were purified from the expression cells obtained by culturing these expression strains, in the same manner as in Example 2.

(2) Confirmation of La, Lb, and Ld Antigen Particles by Plasmid Expression

FIG. 9A shows the results of silver staining, which was performed after each antigen particle prepared in (1) was subjected to SDS-PAGE. Although the molecular weight of each of La, Lb, and Ld proteins was about 42 kDa, the monomer band was present at a position of larger molecular weight because of sugar chain modification; the dimer band was slightly observed at a position of doubled molecular weight.

Further, as a result of WB of the respective antigen particles using anti-S antibody, anti-Pre-S2 antibody, and anti-Pre-S1 antibody, bands were detected at the monomer and dimer positions (FIG. 9B). Since the amounts of the proteins used for electrophoresis were large in all antigens, the detected bands were broad; in particular, in the La antigen, two bands were detected at the dimer position. This is assumed to be due to the difference in sugar chain modification.

The antibodies for the detection of S region and Pre-S1 region used in the WB were the same as those used in Example 2. The antibody for the detection of Pre-S2 region is an anti-Pre-S2 antibody (Beacle, Inc., BCL-ABP2-01), and the secondary antibody was the anti-rabbit IgG-HRP (Santa Cruz, sc-2004).

The above results indicate that the L antigen of each genotype prepared in (1) is constituted of an entire length L protein having S region, Pre-S2 region, and Pre-S1 region, and is constituted of monomers and a slight amount of dimers. The particle sizes of L antigens of the respective genotypes prepared in (1) were measured using a dynamic light scattering method with a Zetasizer (Malvern Panalytical). The results confirmed that the particle sizes were about 55 to 65 nm.

Example 5

Production of Lc Antigen-Expressing Genome-Integrated Vector pRS-Ura3-LC3 and pRS-Leu2-LC2

An LC protein prepared from an Lc antigen expression vector used in Example 2, and an Lc protein-expressing cassette containing promoter and terminator were inserted stepwise into pRS406 (Stratagene), thereby producing pRS-Ura3-LC3 containing the three LC genes shown in FIG. 10.

On the other hand, a vector pRS-Leu2 in which Ura3 of pRS406 was replaced with Leu2 was produced. Next, the Lc antigen expression cassette was inserted stepwise into pRS-Leu2, thereby producing pRS-Leu2-LC2 containing the two LC genes shown in FIG. 11.

Example 6

(1) Production of Lc Antigen Expression Strain Using Genome-Integrated Vector pRS-Ura3-LC3 and pRS-Leu2-LC2, and Purification of Lc Antigen Particle Yeast strains AH22R-U (Ura3, Leu2, and His4 variant strains) were transformed using linearized pRS-Ura3-LC3.

The resulting cells were screened according to a usual method, thereby obtaining Lc antigen expression strain (AH22R-U/Ura3 strain). Next, AH22R-U/Ura3 strain was transformed using linearized pRS-Leu2-LC2 The resulting cells were screened according to a usual method, thereby obtaining Lc antigen expression strain (AH22R-U/Ura3/Leu2 strain). The expression strain was subjected to liquid culture, and Lc antigen particles were purified from the resulting expression cells in the same manner as in Example 2.

Figure 5:
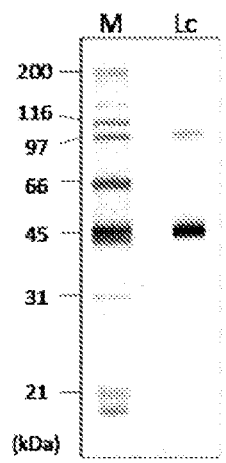
FIG. 5 shows the results of analysis of the Lc antigen and Mc antigen produced in Example 2.
Figure 5:
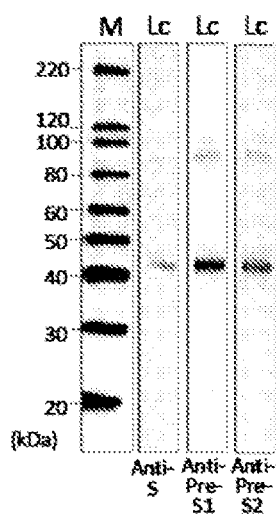
Figure 5:
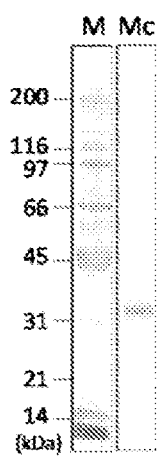
Figure 5:
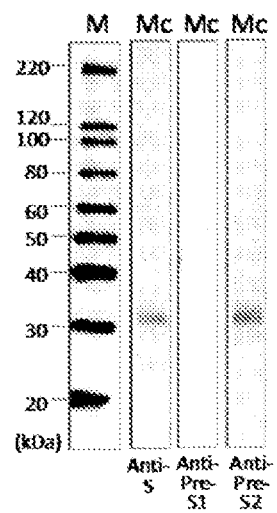
Figure 6:
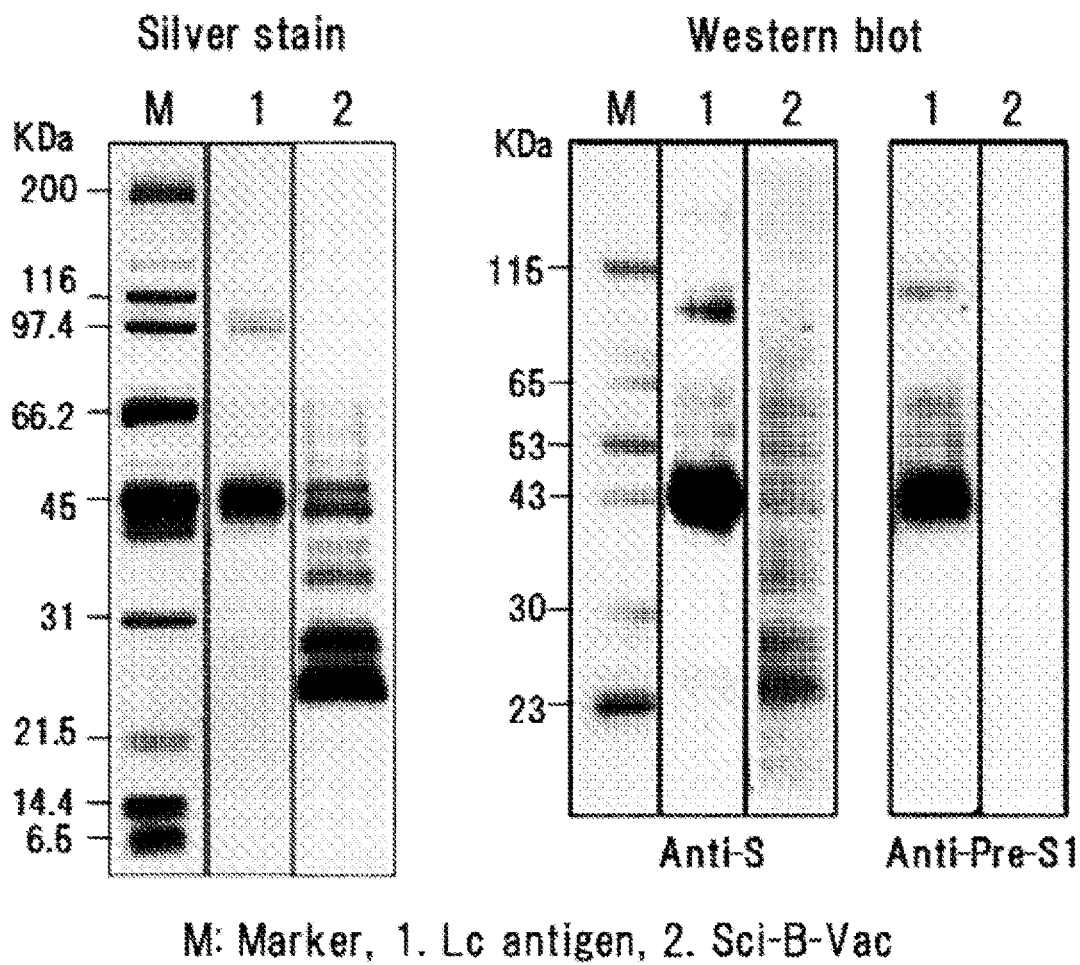
FIG. 6 shows the results of analysis of the Lc antigen produced in Example 2 and Sci-B-Vac antigen.
Figure 7:
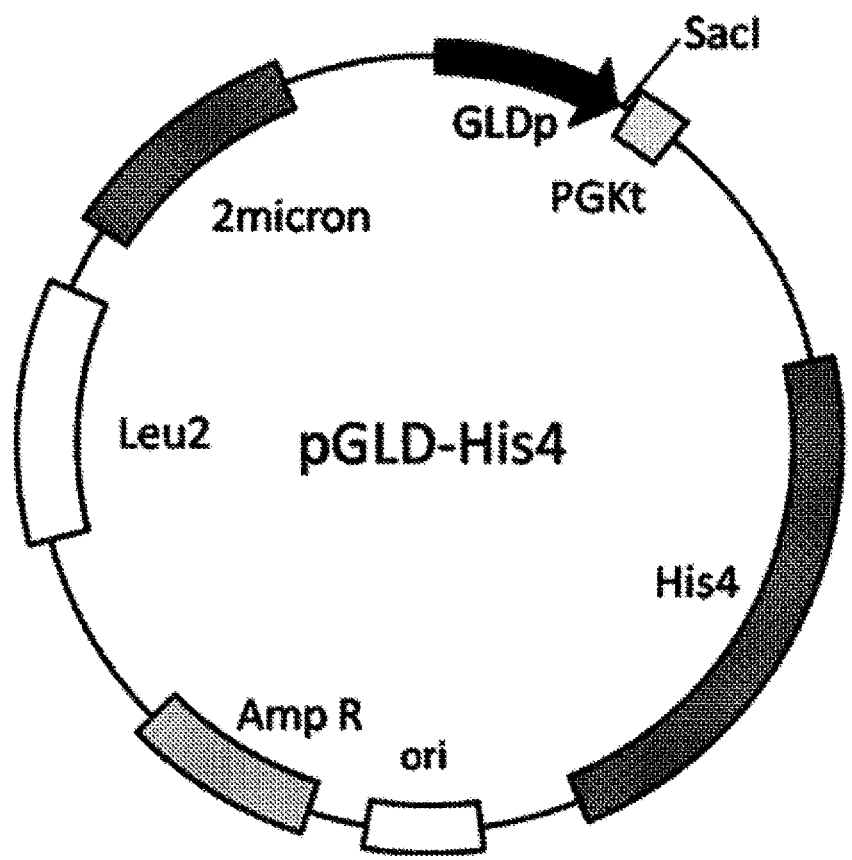
FIG. 7 shows the pGLD-His4 constructed in Example 3.
Figure 8:
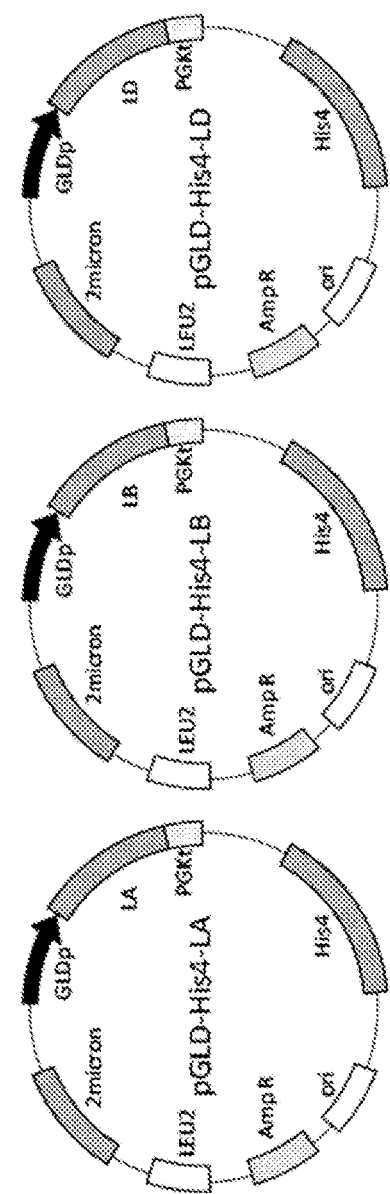
FIG. 8 shows the pGLD-His4-LA, pGLD-His4-LB, and pGLD-His4-LD constructed in Example 4.
Figure 9:
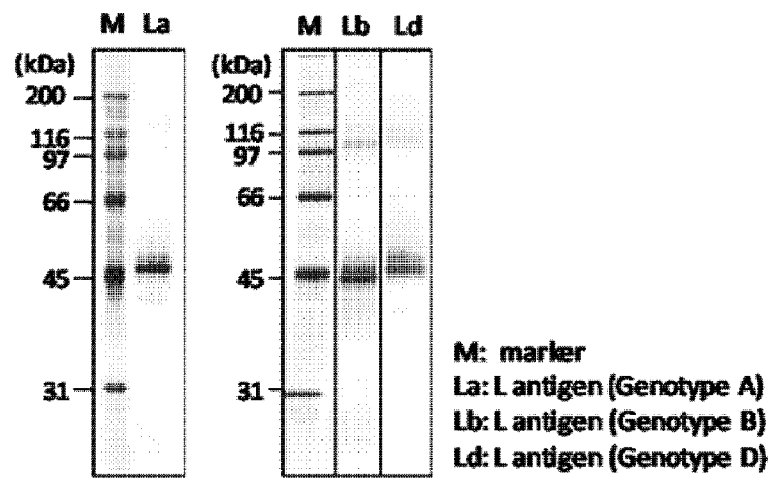
FIG. 9 shows the results of analysis of La, Lb and Ld antigens produced in Example 4.
Figure 9:
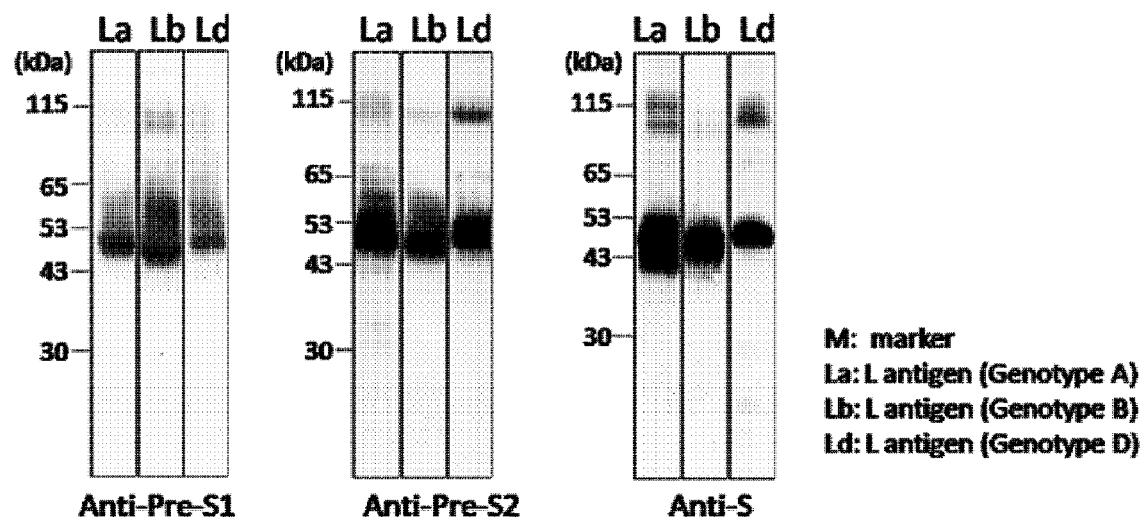
Figure 10:
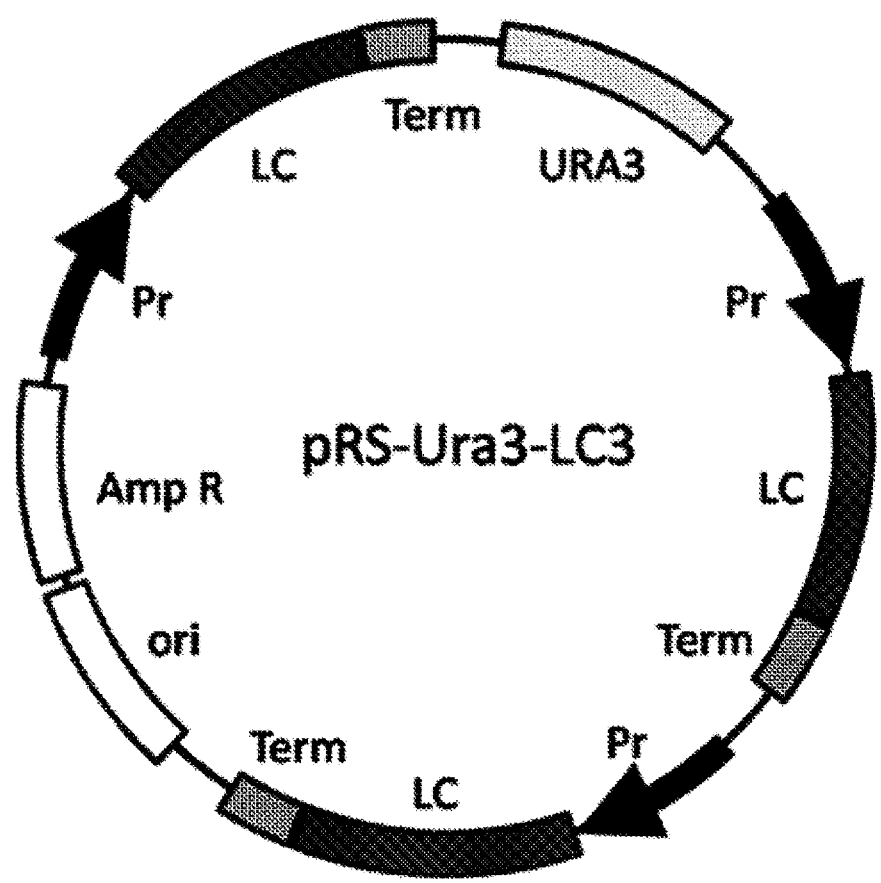
FIG. 10 shows the pRS-Ura3-LC3 constructed in Example 5.
Figure 11:
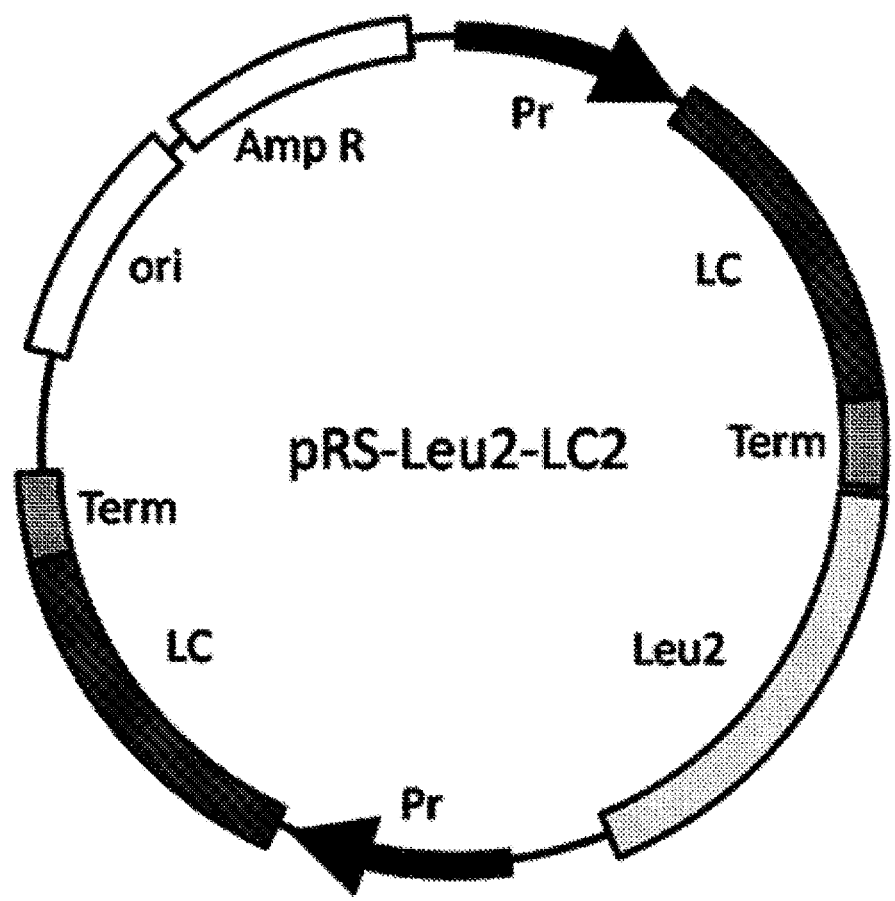
FIG. 11 shows the pRS-Leu2-LC2 constructed in Example 5.
Figure 12:
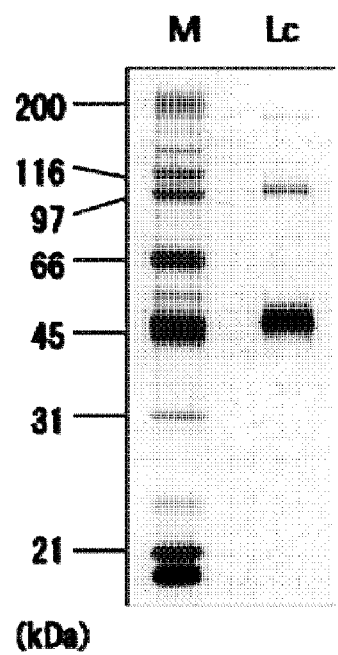
FIG. 12 shows the results of analysis of the Lc antigen produced in Example 6.
Figure 12:
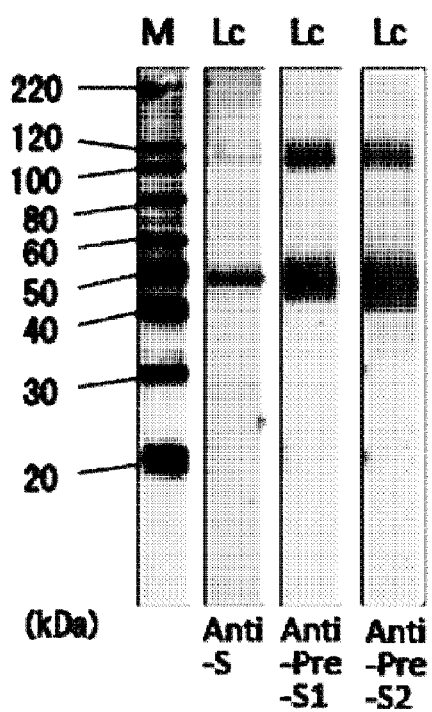

(2) Confirmation of Lc Antigen Particle Produced by Using Genome-Integrated Vector FIG. 12A shows the results of silver staining, which was performed after each antigen particle obtained in (1) was subjected to SDS-PAGE. In the genome-integrated Lc antigen as well, the monomer was observed at the same position as that for the plasmid expression-type Lc antigen shown in FIG. 5, and the dimer band was observed at a position of doubled molecular weight. Similarly to Examples 2 and 4, the particle size of the Lc antigen particle obtained in (1) was about 60.1 nm.

This antigen was subjected to WB using anti-S antibody, anti-Pre-S1 antibody, and anti-Pre-S2 antibody. As shown in FIG. 12B, the bands were present at the positions of the monomer and the dimer in all cases. The antibody used in the WB is the same as that used in Example 2.

These results indicate that the Lc antigen produced using the genome-integrated vector is substantially the same as the Lc antigen obtained by expression using a plasmid, in terms of the molecular weight of the protein and the particle size.

Example 7

Production of Antibody Upon Administration of L Antigen

The Lc antigen particle and the Mc antigen particle prepared in Example 2 and an alum adjuvant were mixed, thereby preparing a formulation for administration. Commercially available Bimmugen (The Chemo-Sero-Therapeutic Research Institute) prepared by using alum adjuvant was used as the S antigen particle of genotype C. They were administered to ICR mice (each group consists of three mice) in an amount of 5 µg of each antigen per mouse. The administration was performed three times, at 2-week intervals. Blood was collected four weeks after the final administration, thereby preparing antisera.

Figure 13:
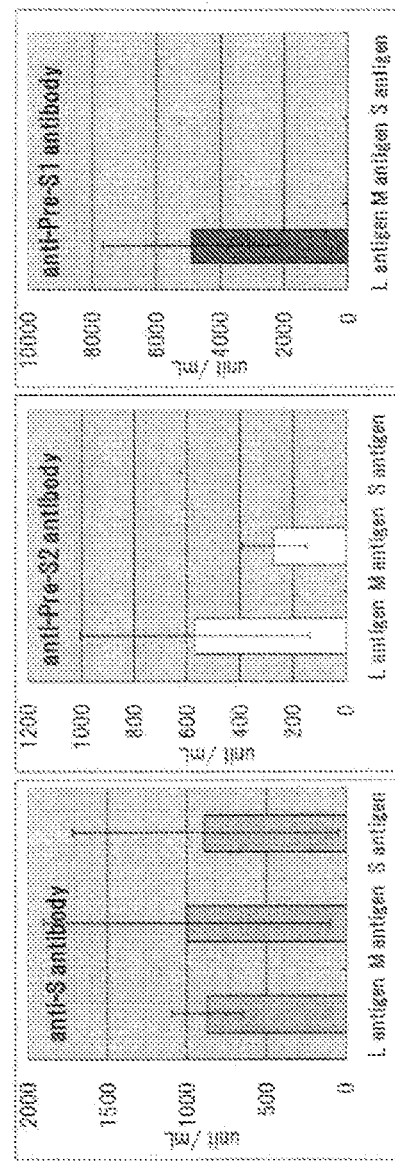
FIG. 13: Example 7 shows the results of the test in Example 7. In each graph of FIG. 13, the vertical axis denotes the production amount of each antibody (anti-S antibody, anti-Pre-S2 antibody, and anti-Pre-S1 antibody) against L antigen, M antigen, and S antigen.

The antisera prepared above were added to an ELISA plate in which the Pre-S1-TRX prepared in Example 1 was immobilized (for the measurement of Pre-S1 antibody), an ELISA plate in which Pre-S2-TRX Beacle, Inc., BCL-AGS2-21) was immobilized (for the measurement of Pre-S2 antibody), and an ELISA plate in which S antigen (purchased from Fitzgerald, USA) was immobilized (for the measurement of S antibody). FIG. 13 shows the results of the measurement of the amounts of the antibodies bound to the immobilized antigens using HRP-labeled anti-mouse IgG as the secondary antibody. Mouse monoclonal anti-Pre-S1 antibody (Beacle, Inc., BCL-AB-001), mouse monoclonal anti-Pre-S2 antibody (Beacle, Inc., BCL-ABM2-01), and mouse monoclonal anti-S antibody (HBS, EXBIO) were used as standard antibodies for preparing a calibration curve.

Immunization with S antigen particle resulted in the production of only anti-S antibody, and immunization with M antigen particle resulted in the production of anti-S antibody and anti-Pre-S2 antibody. Immunization with Lc antigen particle resulted in the production of anti-Pre-S1 antibody, in addition to anti-S antibody and anti-Pre-S2 antibody. It was also found that the anti-Pre-S1 antibody was produced in an amount of about 5 to 10 times the amount of the anti-Pre-S2 antibody or the anti-S antibody. The above results revealed that Lc antigen particle consisting only of Lc protein is suitable for the mass production of anti-Pre-S1 antibody, thus indicating that the immunogenicity of the Pre-S1 region is significantly higher than those of other regions.

Example 8

Figure 14:
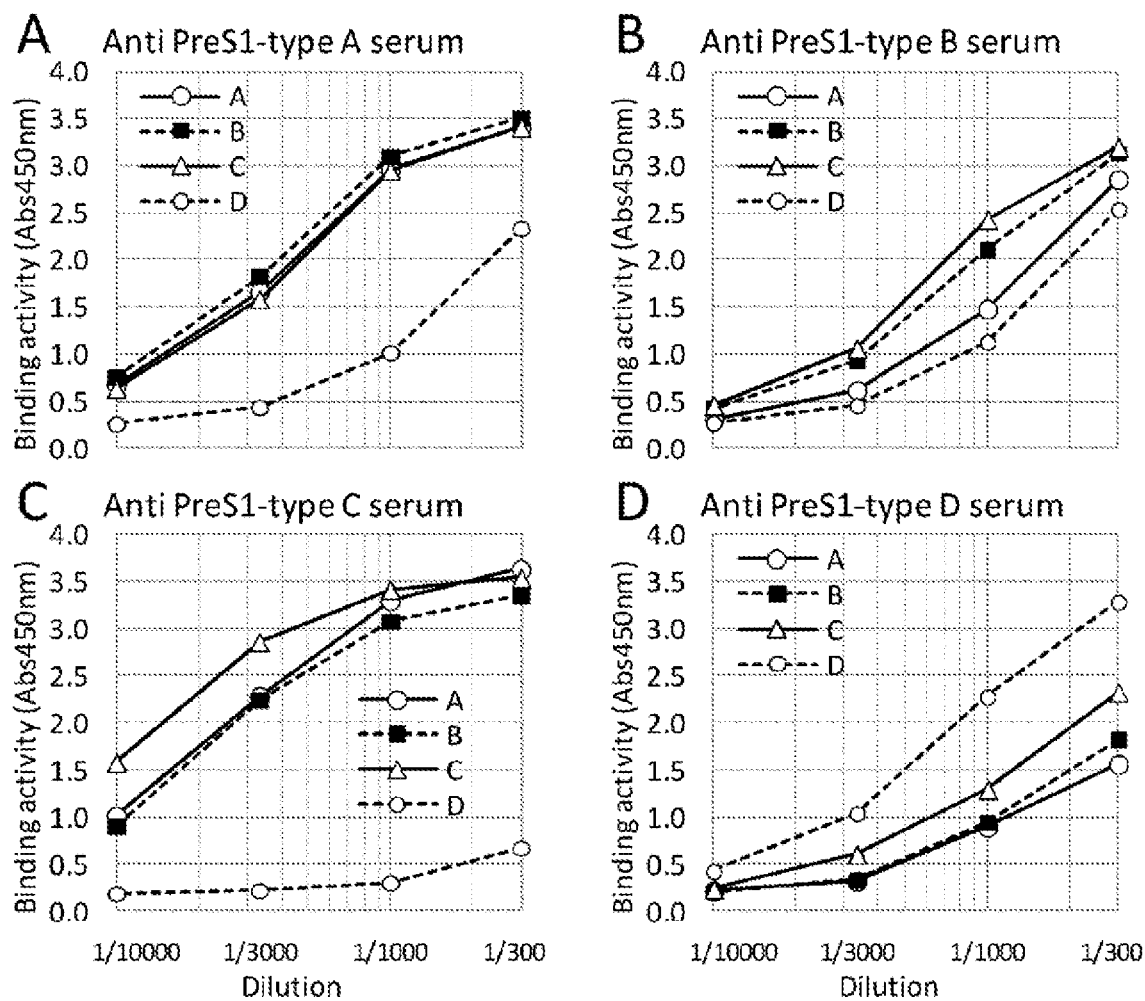
FIG. 14 shows the results of the test in Example 8. A, B, C, and D in each graph in FIG. 14 show the results of antisera obtained by Pre-S1 peptide immunization of immunized genotypes A, B, C, and D, respectively. In each graph of FIG. 13, the horizontal axis denotes the dilution ratio of each antiserum used.

Antisera Prepared by Pre-S1 Peptides of Various Genotypes and Recognition of Pre-S1 of Various Genotypes The Pre-S1 peptides of the four genotypes obtained in Example 1 were mixed with Freund's adjuvant to prepare formulations for administration. Using these formulations, antisera were prepared in the same manner as in Example 7. Dilutions of the antisera were added to ELISA plates in which the four kinds of Pre-S1-TRX fusion proteins prepared in Example 1 were immobilized, and the degree of binding of each antiserum and each Pre-S1 was measured using HRP-labeled anti-mouse antibody as a detection antibody (substrate: TMB). FIG. 14 shows the results.

The antisera obtained by immunization with Pre-S1 peptides of genotypes A and C bound well to Pre-S1 of genotypes A, B, and C; however, their binding was weak with respect to Pre-S1 of genotype D (FIGS. 14A and 14C). On the other hand, although the binding degree of the antiserum obtained by immunization with Pre-S1 peptide of genotype D with respect to Pre-S1 of genotype D was relatively high, its binding degree with respect to Pre-S1 of genotypes A, B, or C was low (FIG. 14D). The above results suggested that the Pre-S1 regions of genotypes A and C trigger similar antibody production; and that therefore, they have a common epitope. On the other hand, the results also suggested that the Pre-S1 region of genotype D has an epitope clearly different from that of genotype A or C. It was also suggested that genotype B has an epitope relatively similar to those of genotypes A and C.

Example 9

Production of Antibody Upon Administration of L Antigen of Each Genotype

Figure 15:
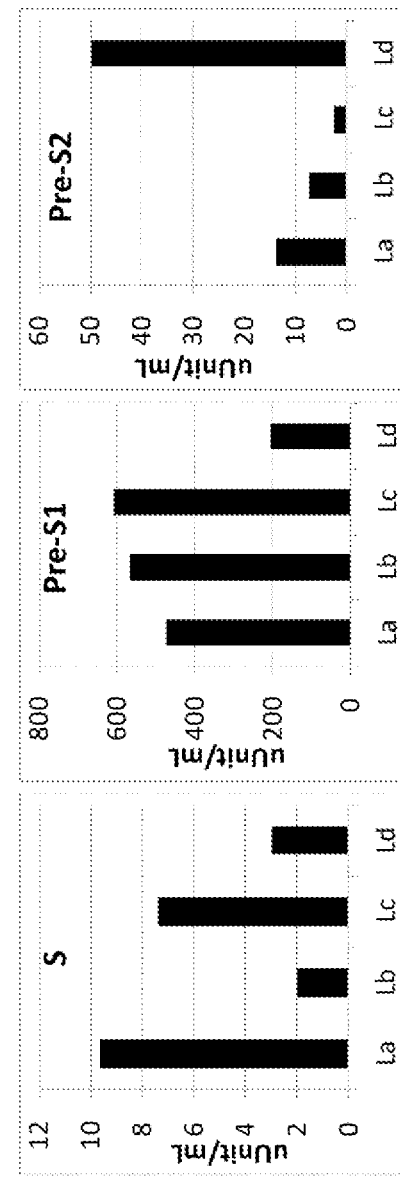
FIG. 15 shows the results of the test in Example 9. In each graph of FIG. 15, the horizontal axis denotes L antigens (from left to right, La antigen, Lb antigen, Lc antigen, and Ld antigen) of each of the immunized genotypes; and the vertical axis denotes the production amounts of anti-S antibody, anti-Pre-S2 antibody, and anti-Pre-S1 antibody.

The L antigens (5 µg each) of the respective genotypes (genotypes A to D) prepared in Example 2 and 4 were mixed with Freund's adjuvant, thereby preparing formulations for administration. ICR mice were immunized by the method of Example 7 to prepare antisera, and the production amounts of the anti-S antibody, the anti-Pre-S2 antibody, and the anti-Pre-S1 antibody were measured in the same manner as in Example 7. FIG. 15 shows the results. Anti-S antibody, anti-Pre-S2 antibody, and anti-Pre-S1 antibody were produced by immunization with L antigen particle of each genotype. The production amount of the anti-Pre-S1 antibody was the highest in all genotypes; the amount was 4 times to several hundred times the amount of the anti-S antibody or the anti-Pre-S2 antibody.

Figure 16:
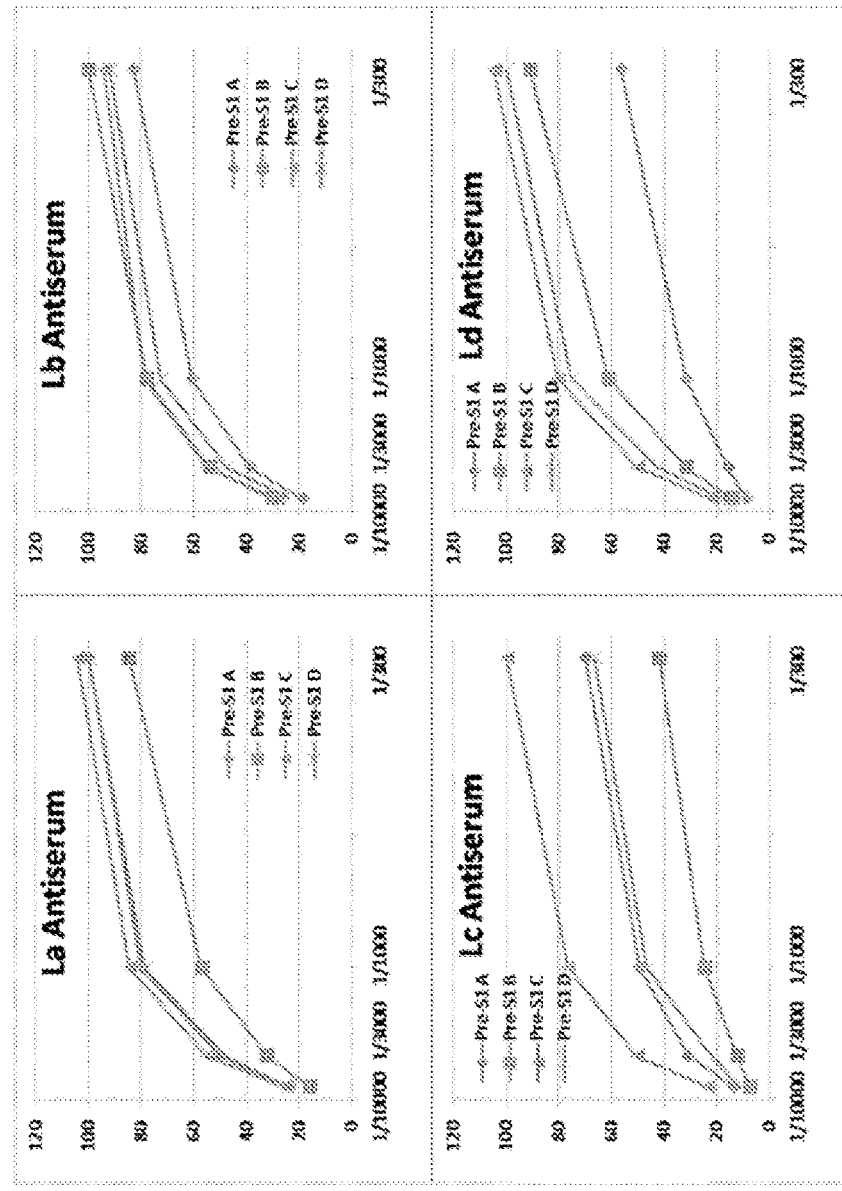
FIG. 16 shows the results of the test in Example 9.
Figure 17:
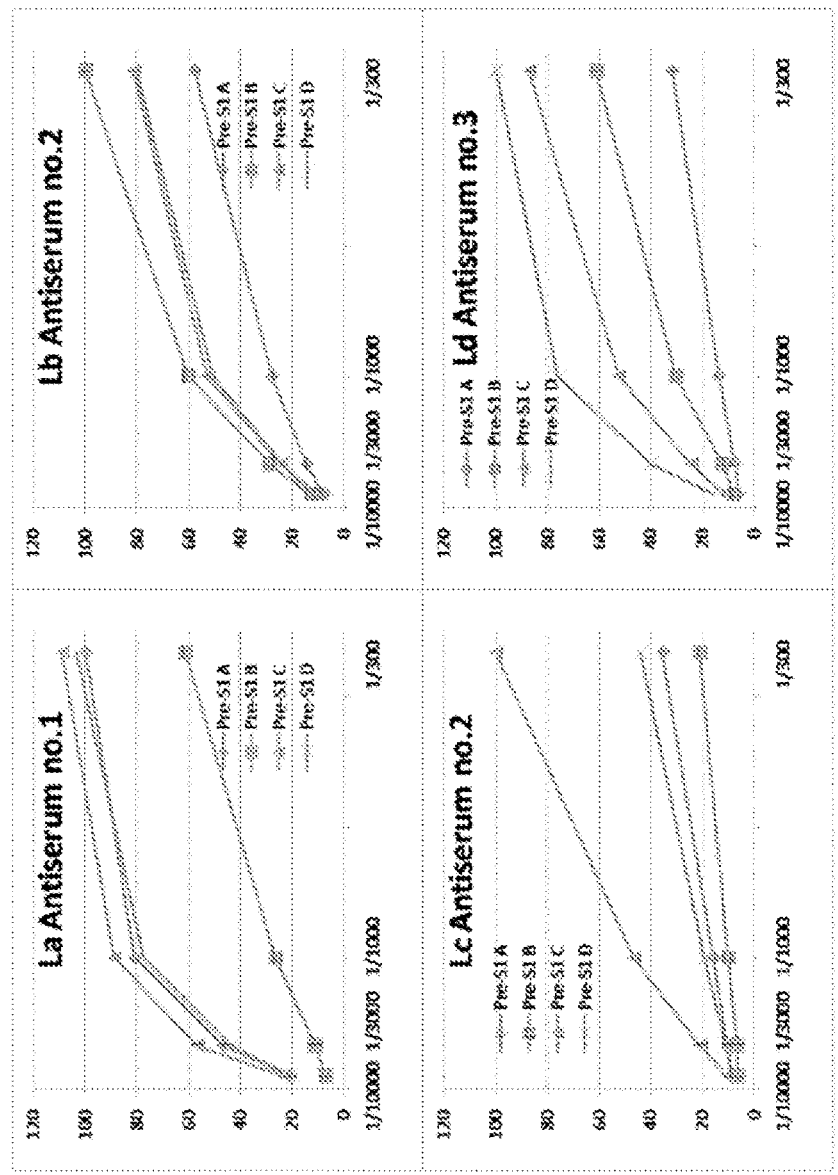
FIG. 17 shows the results of the test in Example 9. The vertical axis and the horizontal axis in each graph in FIG. 17 are the same as those in FIG. 16.

The binding degree of each antiserum described above with respect to Pre-S1 of each genotype (A to D) was observed in the same manner as in Example 8. FIGS. 16 and 17 shows the binding strengths; in these figures, the value of the binding when the immunized L antigen and the Pre-S1 as the measurement target have the same genotype is regarded as 100%, and the binding strength with respect to Pre-S1 of a different genotype is expressed as a relative value.

The results shown in FIG. 16 with regard to the binding with respect to the Pre-S1 of each genotype shown as an average value of the antisera of the three individuals revealed that the antiserum obtained by immunization with Lb antigen also bound well to Pre-S1 of a different genotype; and that, on the other hand, for example, the antiserum obtained by immunization with Ld antigen had a tendency of poor binding with respect to Pre-S1 of genotype A.

Moreover, the results of the individuals shown in FIG. 17 revealed that the binding of the antiserum obtained by immunization with La antigen with respect to Pre-S1 of genotype B was extremely poor in some cases; and that the antisera obtained by immunization with Lb, Lc, and Ld antigens with respect to Pre-S1 having a genotype different from that of the immunizing antigen was also extremely poor in some cases.

The results shown above indicate that anti-S antibody, anti-Pre-S2 antibody, and anti-Pre-S1 antibody are produced by the administration of L antigen particle regardless of the difference in genotype, and that the production amount of the anti-Pre-S1 antibody is the highest. It was also revealed that the binding of anti-Pre-S1 antibody produced by the administration of L antigen particle of a given genotype with respect to the Pre-S1 regions of other genotypes was extremely poor in some cases. Therefore, the anti-Pre-S1 antibody produced by the immunization with L antigen of a single genotype may not recognize the Pre-S1 region of a different genotype due to the genotype difference. Since the object of the present invention is to create a virus-like particle capable of recognizing the Pre-S1 region of multiple genotypes, the following experiments were made.

Example 10

Recognition of Pre-S1 of Various Genotypes by Antisera Obtained by Mixed Administration of L Antigens of Different Genotypes As shown in Table 3 below (binding with respect to Pre-S1 of each genotype upon mixed administration of L antigens of various genotypes), equal amounts of L antigens of 2 or 3 genotypes prepared in Example 2 and Example 4 were mixed; and the three ICR mice were immunized with the mixture having the total L antigen amount of 5 µg in the same manner as in Example 9, thereby obtaining antisera.

The binding degrees of each of the obtained antisera with respect to Pre-S1 of genotypes A, B, C, and D were measured by the method shown in Example 8. Table 3 shows the measured binding degrees. In Table 3, the degree of binding with respect to Pre-S1 of genotype A when the immunization is performed using a mixture of La and Lb, and a mixture of La and Ld, is regarded as 100%; and the binding degrees with respect to Pre-S1 of other genotypes are shown as relative values. Similarly, in Table 3, when the immunization is performed with a mixture of Lb and Lc, and a mixture of Lb and Ld, the degree of binding with respect to Pre-S1 of genotype B is regarded as 100%; when the immunization is performed with a mixture of Lc and Ld, and a mixture of Lc, Lb, and Ld, the degree of binding with respect to Pre-S1 of genotype C is regarded as 100%; and the binding degrees with respect to Pre-S1 of other genotypes are shown as relative values. All values are average values of the antisera obtained from the three individuals. Further, FIG. 18 shows the results of measurement of the antisera obtained by immunization with a mixture of Lc and Ld, as an example of mixed administration.

Figure 18:
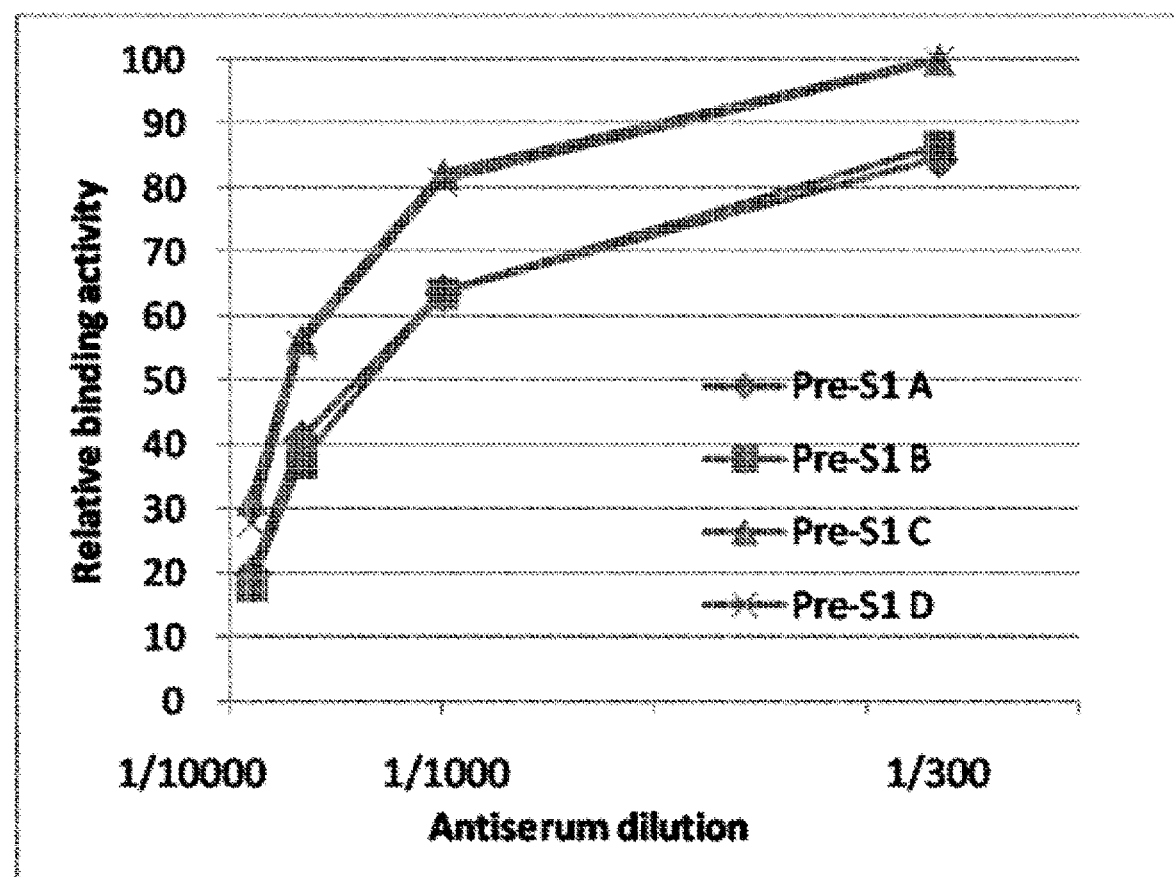
FIG. 18 shows the results of the test in Example 10. The vertical axis and the horizontal axis in each graph in FIG. 18 are the same as those in FIG. 16.

FIG. 18 revealed that the antisera obtained by the immunization with a mixture of Lc and Ld bound substantially equally to the Pre-S1 of genotypes C and D. The degree of binding to the Pre-S1 of genotypes A and B was about 85%. When L antigens of two genotypes were mixed, the binding to the Pre-S1 of a different genotype was improved, compared with the case where L antigen of each of the genotypes shown in Example 9 (FIG. 17) was administered alone. Further, among these individuals, the one with the lowest binding degree had a binding degree of 73%, and there were none showing excessively low binding. Further, as shown in Table 3, the same phenomenon was observed when a mixture of a combination of L antigens of other genotypes was used. In particular, antisera obtained by the immunization with mixed L antigens of the three genotypes had the highest binding degree with respect to Pre-S1 of the respective genotypes.

TABLE 3

|  |  | Binding to Pre-S1 | | | |
| --- | --- | --- | --- | --- | --- |
|  |  | A | B | C | D |
| L antigen combination | La + Lb | 100 | 98 | 92 | 87 |
|  | La + Ld | 100 | 85 | 86 | 110 |
|  | Lb + Lc | 87 | 100 | 112 | 75 |
|  | Lb + Ld | 68 | 100 | 76 | 8 |
|  | Lc + Ld | 76 | 85 | 100 | 99 |
|  | Lc + Lb + Ld | 89 | 98 | 100 | 120 |

Example 11

Hybrid L Antigen Expression Strain (Lh1 Antigen) Comprising Lc and Ld Proteins, as the Antigen (1) Production of Plasmid-Type Lh1 Expression Vector The genome-integrated Lc antigen expression strain (AH22R-U/Ura3/Leu2 strain) prepared in Example 6 was transformed using the Ld antigen expression plasmid pGLD-His4-LD prepared in Example 4; and the resulting cells were screened according to a usual method, thereby obtaining hybrid L antigen (hereinafter may be referred to as "Lh1 antigen" in this specification) expression strain containing Lc protein and Ld protein in a single particle.

Figure 19:
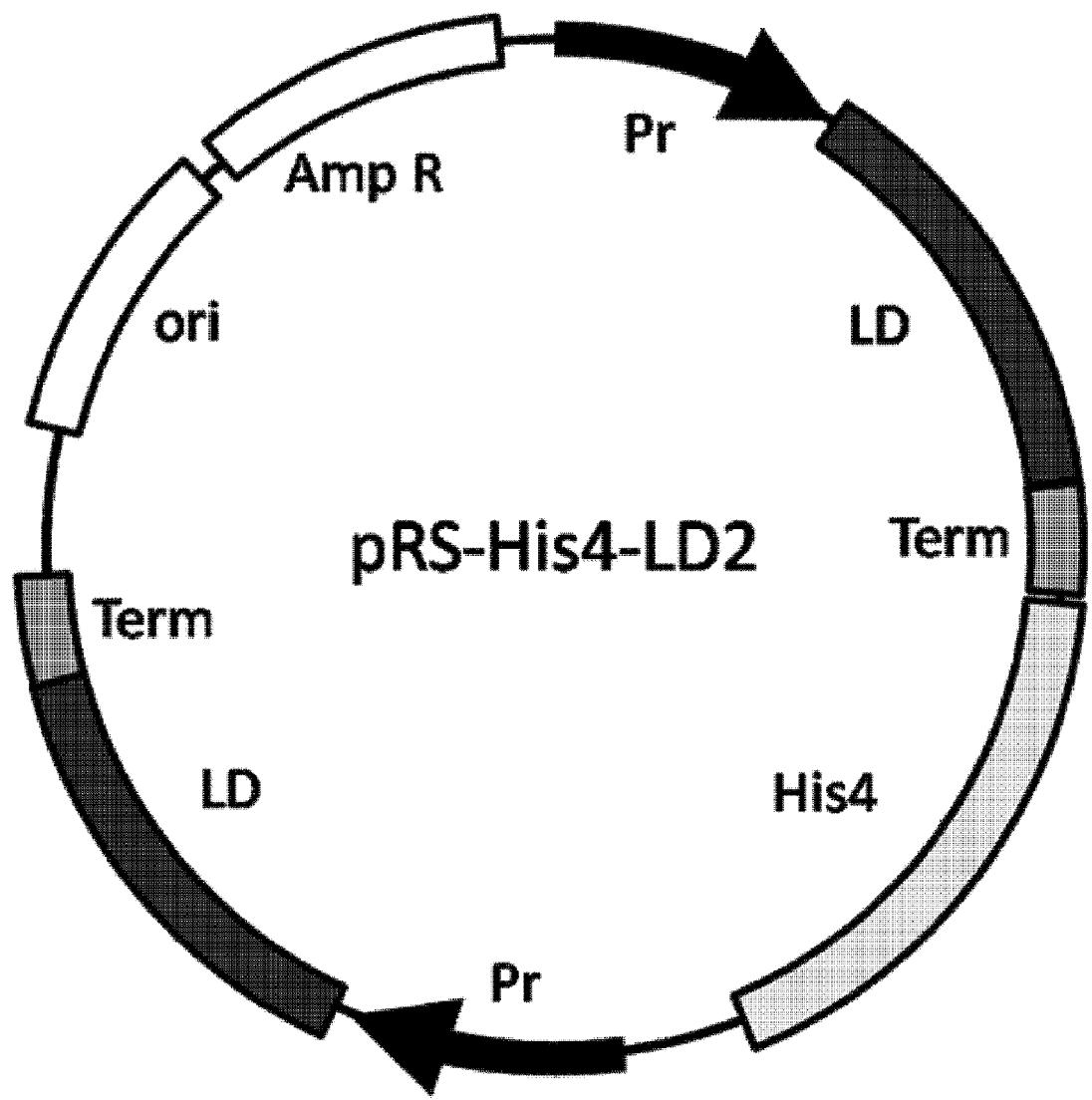
FIG. 19 shows the pRS-His4-LD2 constructed in Example 11(2).

(2) Production of Lh1 Antigen Expression Strain Using Genome Integration-Type: 1 pRS-His4 was produced by replacing URA3 of pRS406 with HIS4, and LD gene prepared from the Ld antigen expression vector prepared in Example 4 and an Ld antigen expression cassette containing promoter and terminator were inserted, thereby preparing pRS-His4-LD2 containing the two LD genes shown in FIG. 19.

The Lc antigen expression strain (AH22R-U/Ura3/Leu2 strain) prepared in Example 6 was transformed using linearized pRS-His4-LD2; followed by screening according to a usual method, thereby obtaining Lh1 expression strain.

(3) Production of Lh1 Antigen Expression Strain Using Genome Integration-Type: 2

Figure 20:
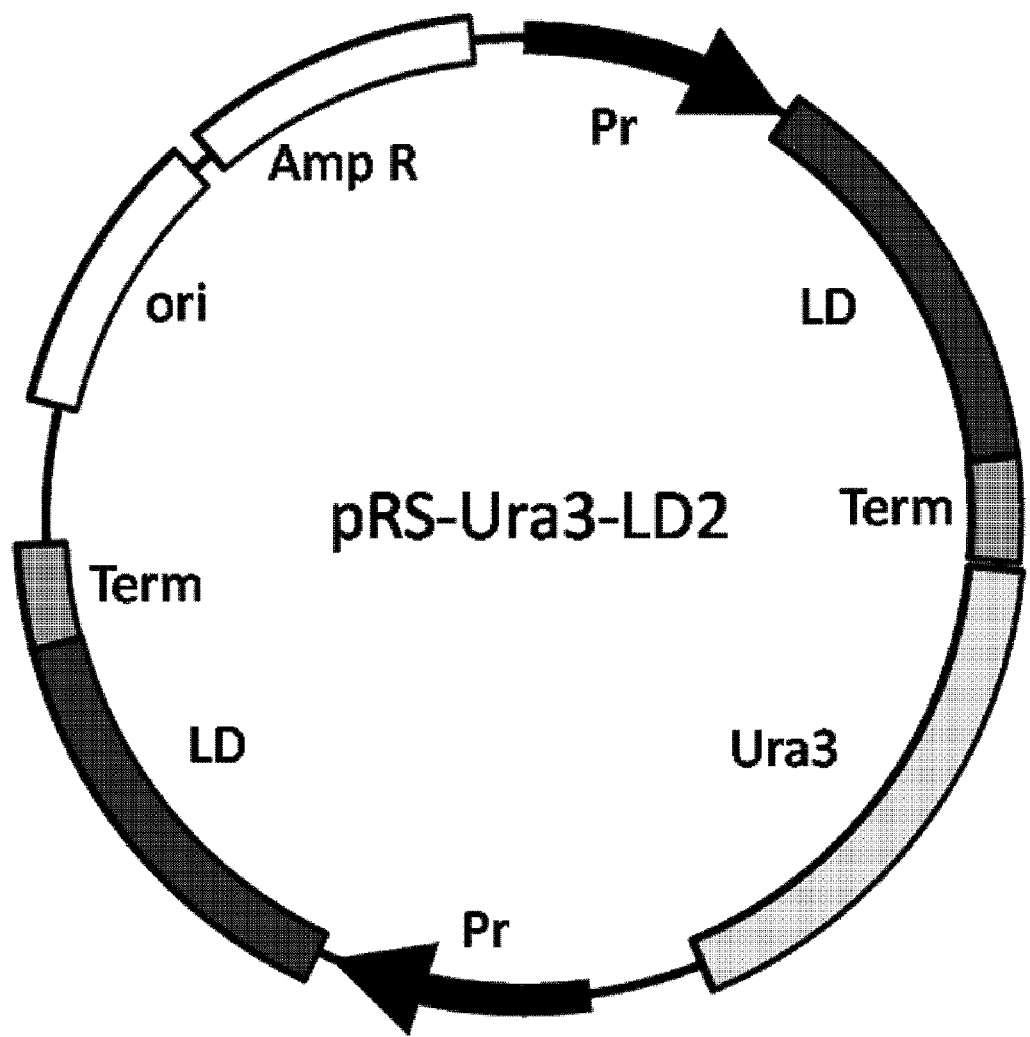
FIG. 20 shows the RS-Ura3-LD2 constructed in Example 11(3).

Yeast strain (AH22R-U) was transformed using the Lc antigen expression vector pRS-Leu2-LC2 prepared in Example 5; followed by screening according to a usual method, thereby obtaining Lc expression strain. The obtained Lc expression strain was transformed using the Ld antigen expression vector pRS-Ura3-LD2 shown in FIG. 20 prepared in the same manner as in Example 5; followed by screening according to a usual method, thereby obtaining Lh1 expression strain.

Example 12

Production and Confirmation of Lh1 Antigen (1) Culture and Purification of Lh1 Antigen Lh1 antigen particle was purified from the cells obtained by culturing the Lh1 expression strain obtained in (1) to (3) of Example 11 in a liquid medium, in the same manner as in Example 2.

(2) Production of Antibody That Recognizes Pre-S1 Regions of Genotypes C and D

IgG was purified from antisera obtained by immunizing rabbits with Pre-S1-TRX antigen of genotype C. The resulting IgG was made to pass through a genotype D Pre-S1-TRX-immobilized column twice so as to remove IgG bound to Pre-S1 of genotype D, thereby obtaining anti-S1c antibody capable of specifically detecting Pre-S1 of genotype C. Further, IgG was purified from antisera obtained by immunizing rabbits with Pre-S1-TRX antigen of Genotype D. The resulting IgG was made to pass through a genotype C Pre-S1-TRX-immobilized column twice, thereby obtaining anti-Pre-S1d antibody capable of specifically detecting Pre-S1 of Genotype D.

(3) Confirmation of Lh1 Antigen Particle Containing Lc Protein And Ld Protein

Figure 21:
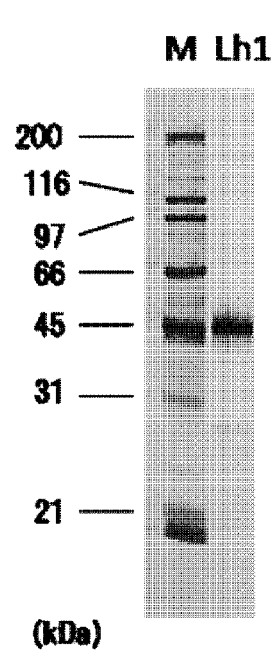
FIG. 21 shows the results of analysis of the Lh1 antigen produced in Example 12.
Figure 21:
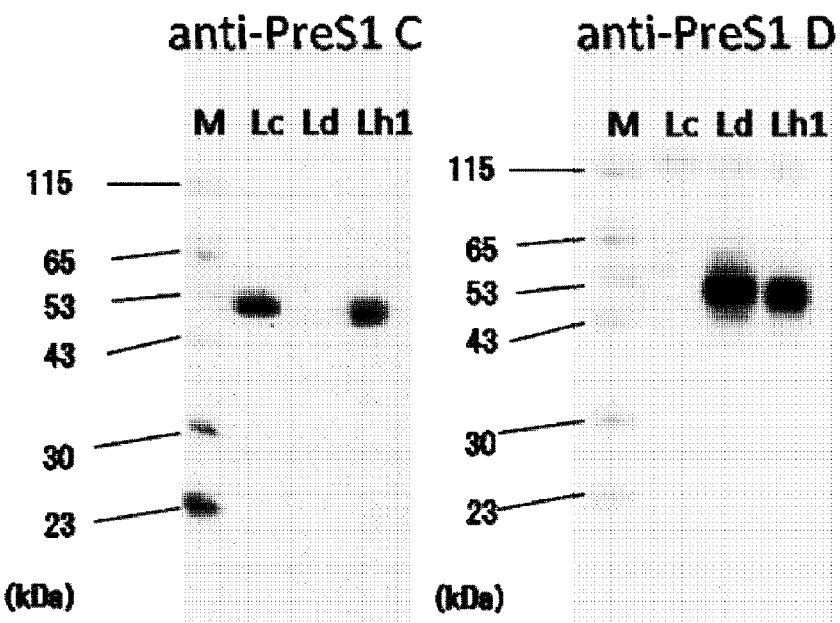

The Lh1 antigen purified from the expression strain of Example 11(2) was subjected to SDS-PAGE, followed by silver staining. FIG. 21A shows the results of silver staining. L protein was observed at a position of a larger molecular weight than 42 kDa due to sugar chain modification.

WB was further performed using anti-Pre-S1c antibody and anti-Pre-S1d antibody that specifically recognize the Pre-S1 regions of genotypes C and D produced in (2); as a result, it was revealed that Lh1 antigen was detectable by any of the anti-Pre-S1 antibodies. In contrast, Lc antigen and Ld antigen as the control were detectable only by antibodies against the corresponding genotypes. The above results indicate that the Lh1 antigen is an antigen having both Lc protein and Ld protein. The particle size of the Lh1 antigens obtained from the expression strains of (1) to (3) of Example 11 was measured using a Zetasizer. It was revealed that the particle size was about 58 to 63 nm, and that these antigens form particles in the same manner.

Figures 22, 23:
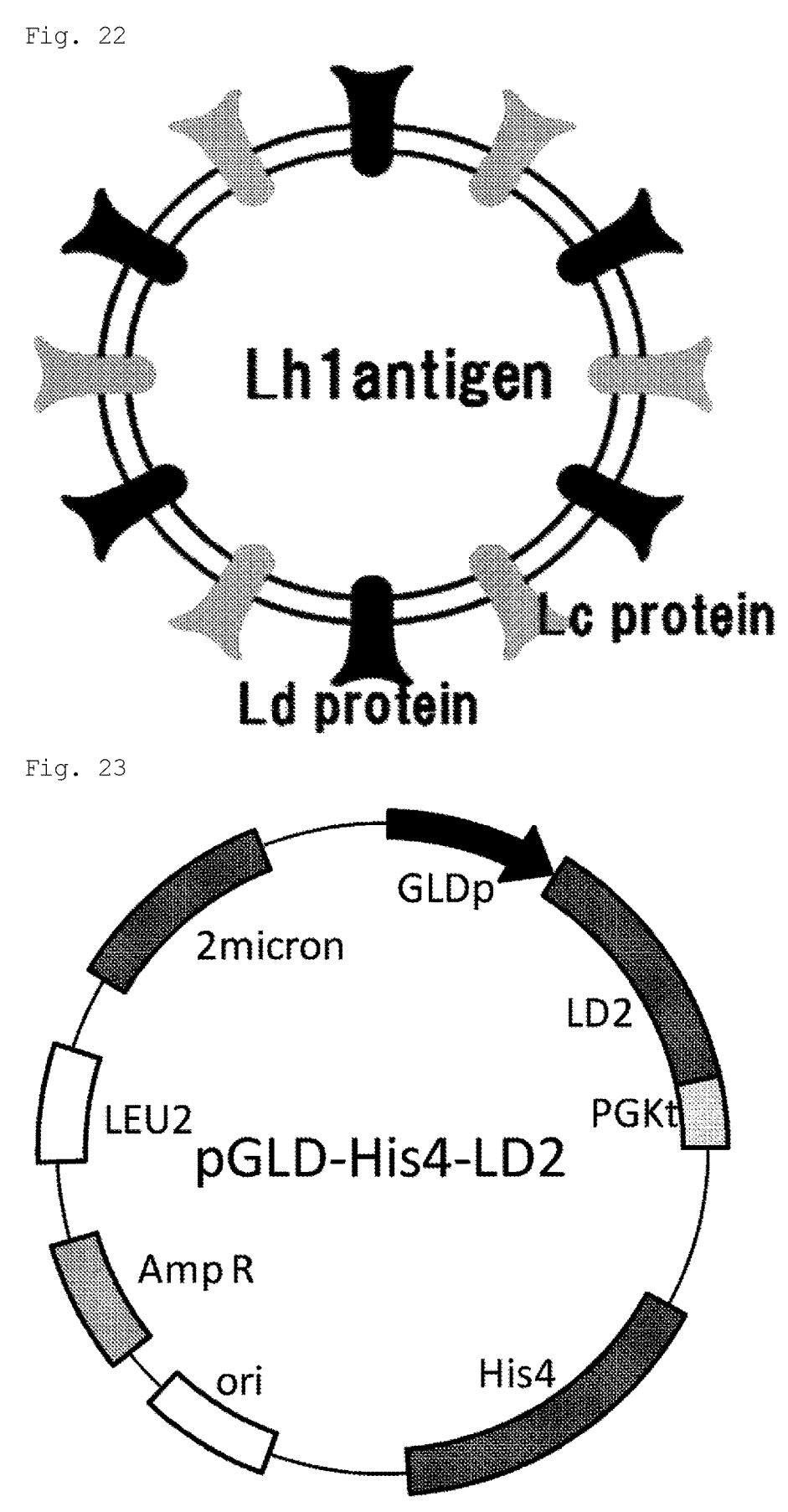

Then, experiments were made as to whether the Lh1 antigen obtained in (1) has a structure shown in FIG. 22 in which L protein of genotype D and L protein of Genotype C are presented on a single particle, using anti-Pre-S2u epitope antibody (Institute of Immunology Co., Ltd., Non-patent Document 7) which specifically bind to genotype D, the anti-Pre-S1c antibody prepared in (2), and anti-S antibody used in Example 7.

The anti-Pre-S2u antibody or the anti-Pre-S1c antibody were immobilized on a ELISA plate; and the Lc antigen of Example 6, the Ld antigen of Example 4, and the Lh1 antigen described above were trapped by immobilized antibodies. The trapped antigens were detected with the three antibodies. The results are shown in Table 4 (the analysis results obtained by the anti-Pre-S2u antibody, the anti-Pre-S1c antibody, and the anti-S antibody of Lh1 antigen). The cutoff value in this measurement system is 0.4.

TABLE 4

| Immobilized antibody | | anti-Pre-S2u | | anti-Pre-S1c | |
|---|---|---|---|---|---|
| Detection antibody | | anti-Pre-S1c | anti-S | anti-Pre-S2u | anti-S |
| antigen | Lc | 0.212 | 0.028 | 0.038 | 0.671 |
| | Ld | 0.360 | 0.947 | 0.390 | 0.256 |
| | Lh1 | 1.695 | 1.517 | 1.027 | 1.050 |

When the anti-Pre-S2u antibody was immolilized, and anti-Pre-S1c antibody or anti-S antibody was used as the detection antibody, no Lc antigen was detected. Since the results of WB shown above and the results of Examples 2 and 12 revealed that the Lc antigen binds to the anti-Pre-S1c antibody or the anti-S antibody, the results indicate that the Lc antigen did not bind to the anti-Pre-S2u antibody having specificity for genotype D, and was not trapped in the ELISA plate. In contrast, the Ld antigen was trapped by the anti-Pre-S2u antibody and detected by the anti-S antibody, but was not detected by the anti-Pre-S1c antibody having specificity for genotype C. The Lh1 antigen was trapped by the anti-Pre-S2u antibody, and therefore detected by both the anti-Pre-S1c antibody and the anti-S antibody.

Further, when anti-Pre-S1c antibody was used as the solid-phased antibody, and anti-Pre-S2u antibody or anti-S antibody was used as the detection antibody, the Lc antigen was detected only by the anti-S antibody. The Ld antigen was not trapped by the anti-Pre-S1c antibody, and was not detected by any of the detection antibodies. On the other hand, the Lh1 antigen was trapped by the anti-Pre-S1c antibody, and was detected by all antibodies.

The above results indicate that the Pre-S2 of genotype D and the Pre-S1 of Genotype C are displayed on the produced Lh1 antigen particle, which means that the Lh1 antigen is an antigen having the structure shown in FIG. 22 in which L protein of genotype D and L protein of genotype C are present on a single particle.

Example 13

Hybrid L Antigen Particle (Lh1b Antigen) Comprising Lc and Ld2 Antigens (1) Production of Plasmid-Type Ld2 Antigen Expression Vector The Ld2 protein expression vector comprising Pre-S1 region of genotype D and Pre-S2 and S region of genotype C was produced as follows. Using the Ld expression vector pGLD-His4-LD prepared in Example 4 as a template, the regions other than Pre-S2 and S regions (i.e., Pre-S1 and vector portion) were amplified by inverse PCR method. Separately, fragments of Pre-S2 region and S region of genotype C were produced using the genotype C shown in Table 2 as a template. The fragments were incorporated into a vector fragment having the Pre-S1 region, thereby producing the pGLD-His4-LD2 shown in FIG. 23. The particle consisting only of Ld2 protein may be referred to as "Ld2 antigen" in this specification.

Figure 24:
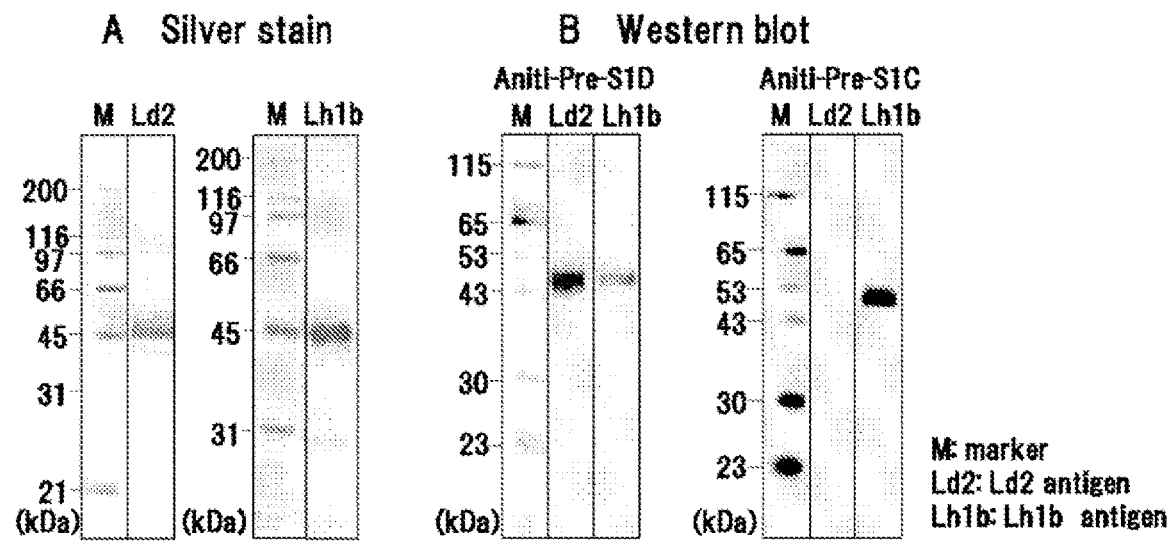
FIG. 24 shows the results of analysis of the Ld2 antigen and Lh1b antigen produced in Example 13.

(2) Production of Antigens of Ld2 Antigen Particle Expression Strain and Hybrid L Antigen Particle (Lh1b Antigen) Expression Strain As in Example 4, yeast (AH22R-strain) was transformed using pGLD-His4-LD2, thereby obtaining Ld2 antigen expression strain. The Lc antigen expression strain prepared in Example 6 was transformed using pGLD-His4-LD2; followed by screening according to a usual method, thereby obtaining Lh1b antigen expression strain. Ld2 antigen and Lh1b antigen were purified from the cells obtained by culturing the strain in the same manner as in Example 2. The purified Ld2 antigen and the purified Lh1b antigen were subjected to SDS-PAGE, and performed silver staining; as a result, as shown in FIG. 24, bands were observed near the monomer position and the dimer position. Further, as a result of WB of these antigens, both antigens were detected at expected positions with respect to the anti-Pre-S1d antibody. With respect to the anti-Pre-S1c antibody, detection was observed for Lh1b antigen, but not observed for Ld2 antigen. The antibody used in the WB was the same as that used in Example 12.

(3) Consideration of Immunological Property of Ld2 Antigen

5 μg each of the Lc antigen produced in Example 2 and the purified Ld2 antigen were used to immunize three mice individually in the same manner as in Example 7, thereby obtaining antisera. With the obtained antisera, the degree of binding with respect to Pre-S1 of each of the four genotypes was observed in the same manner as in Example 8. Table 5 shows average values obtained by the results for each group.

TABLE 5

| Antiserum | Dilution | Binding to | | | |
| --- | --- | --- | --- | --- | --- |
| | | Pre-S1 A | Pre-S1 B | Pre-S1 C | Pre-S1D |
| Lc | 1/300 | 1.57 | 1.43 | 2.35 | 1.54 |
| | 1/1000 | 1.14 | 0.85 | 1.76 | 1.01 |
| | 1/3000 | 0.63 | 0.32 | 1.16 | 0.40 |
| | 1/10000 | 0.24 | 0.07 | 0.47 | 0.09 |
| Ld2 | 1/300 | 1.68 | 1.48 | 2.17 | 2.48 |
| | 1/1000 | 0.86 | 0.68 | 1.21 | 1.77 |
| | 1/3000 | 0.32 | 0.20 | 0.47 | 0.96 |
| | 1/10000 | 0.10 | 0.01 | 0.13 | 0.30 |

The antisera prepared by using the Ld2 antigen had the strongest binding with respect to Pre-S1 of genotype D, and had weak binding with respect to Pre-S1 of genotypes A and B. This is similar to the state of binding of the antisera prepared by using the Ld antigen shown in FIG. 16 described in Example 9 with respect to Pre-S1 of each genotype. The above results indicate that production of antibody having the same property as that of the antibody with respect to Pre-S1 produced by L antigen of genotype D is possible by replacing only the Pre-S1 region of Lc antigen with the Pre-S1 of genotype D.

Example 14

Hybrid L Antigen (Lh2 Antigen) Comprising La and Ld Antigens

Figure 25:
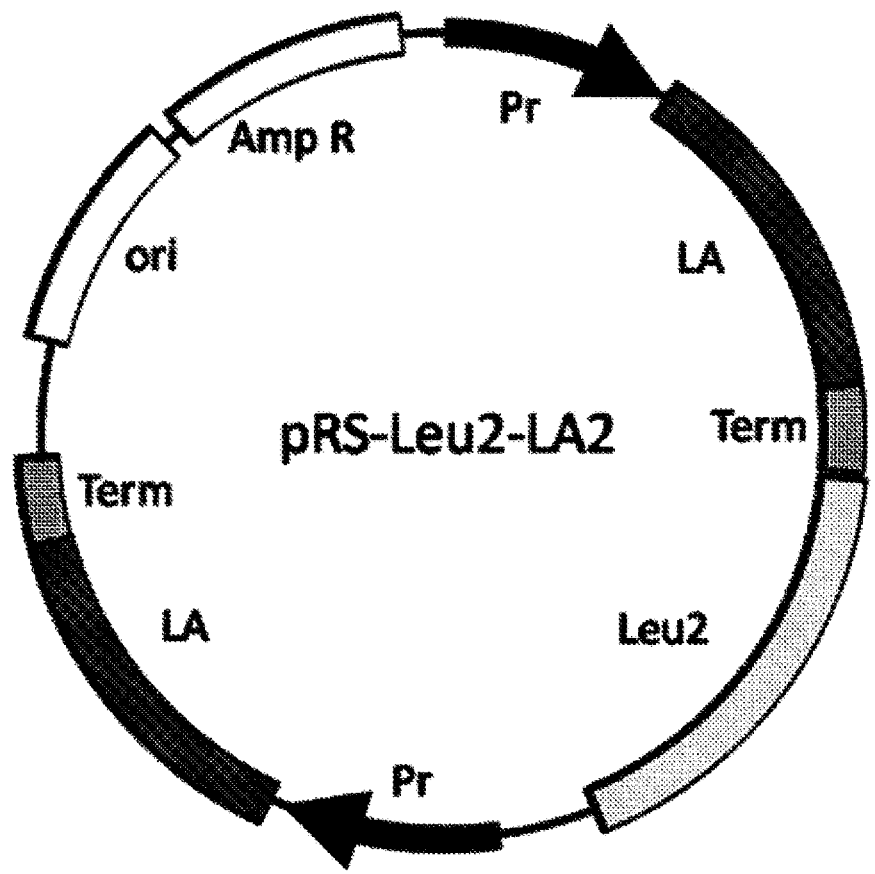
FIG. 25 shows the pRS-Leu2-LA2 constructed in Example 14.
Figure 26:
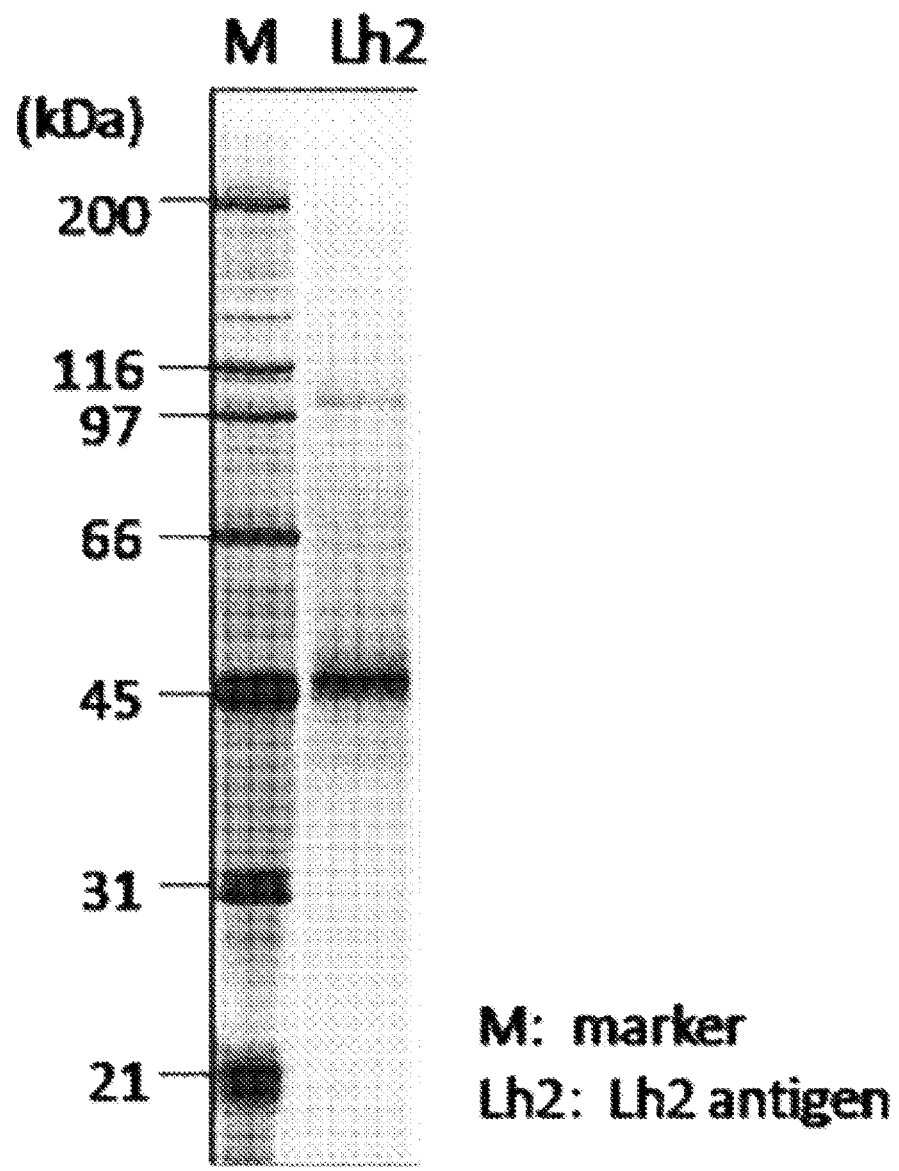
FIG. 26 shows the results of analysis of the Lh2 antigen produced in Example 14.

The genome-integrated La expression vector pRS-Leu2-LA2 shown in FIG. 25 was prepared in the same manner as in Example 5. Yeast strain AH22R-U was transformed using the vector; followed by screening according to a usual method, thereby obtaining La antigen expression strain. Subsequently, the resulting La antigen expression strain was transformed using the Ld expression vector pRS-His4-LD2 prepared in Example 11; followed by screening according to a usual method, thereby obtaining yeast strain expressing La protein and Ld protein. Lh2 antigen was purified from the cells obtained by culturing the strain in the same manner as in Example 2. After the purified Lh2 antigen was subjected to SDS-PAGE, silver staining was performed; as a result, as shown in FIG. 26, bands were observed at the positions of molecular weights near the monomer and dimer.

Example 15

Hybrid L Antigen (Lh3 Antigen) Comprising Lb And Lc Antigens

Figure 27:
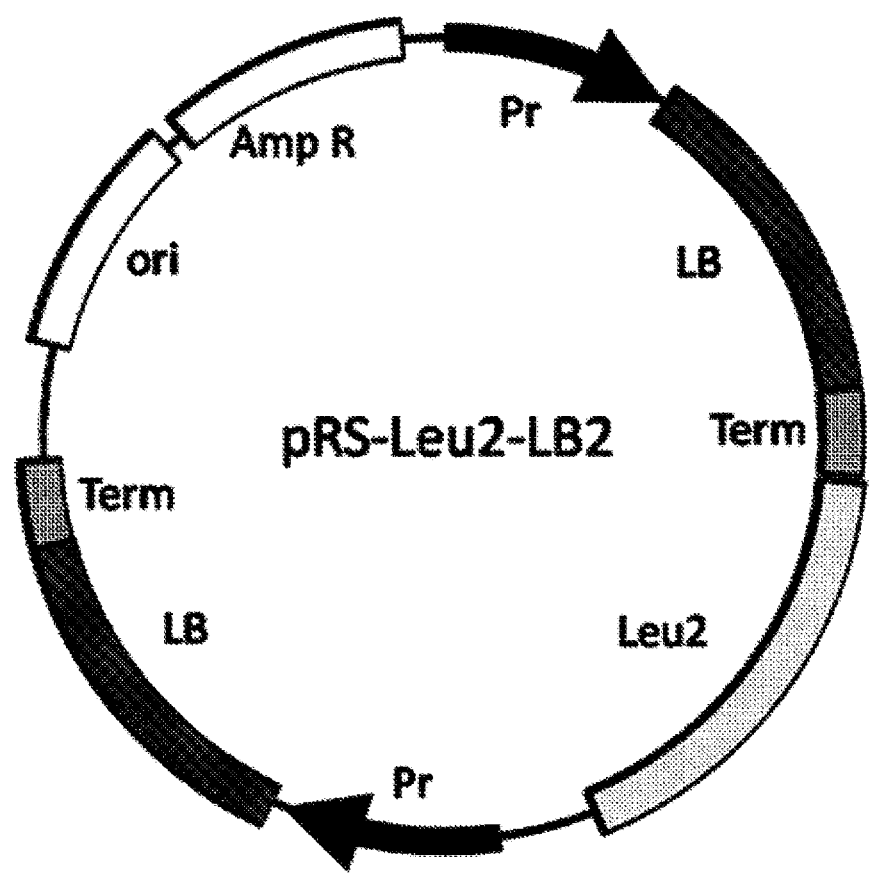
FIG. 27 shows the pRS-Leu2-LB2 constructed in Example 15.
Figure 28:
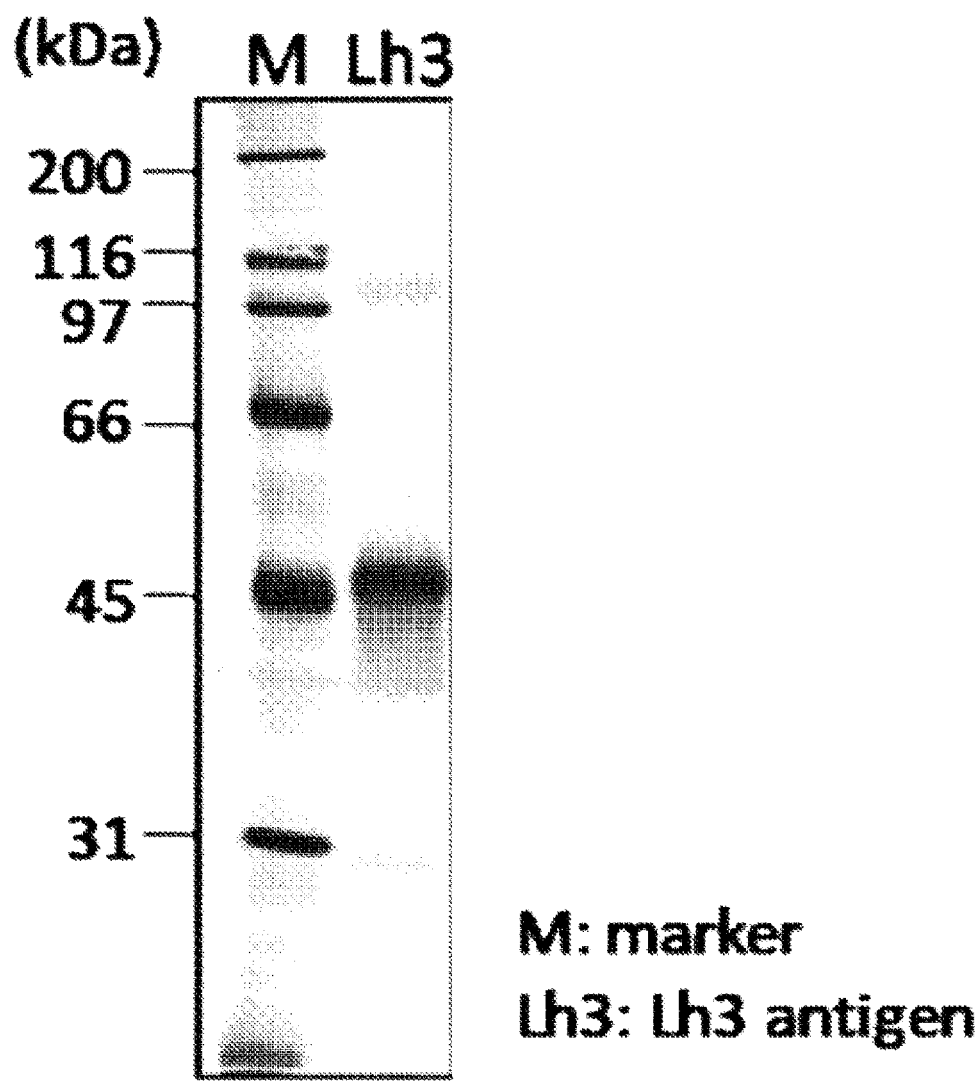
FIG. 28 shows the results of analysis of the Lh3 antigen produced in Example 15.

The genome-integrated Lb expression vector pRS-Leu2-LB2 shown in FIG. 27 was prepared in the same manner as in Example 5. The Lc antigen expression strain (AH22R-U/Ura3 strain) prepared in Example 6 was transformed using the vector; followed by screening according to a usual method, thereby obtaining yeast strain expressing Lb protein and Lc protein. Lh3 antigen was purified from the cells obtained by culturing the strain in the same manner as in Example 2. After the purified Lh3 antigen was subjected to SDS-PAGE, silver staining was performed; as a result, as shown in FIG. 28, bands were observed at the positions near the monomer and dimer.

Example 16

Hybrid L Antigen (Lh4 Antigen) Comprising Lb, Lc, and Ld Proteins

Figure 29:
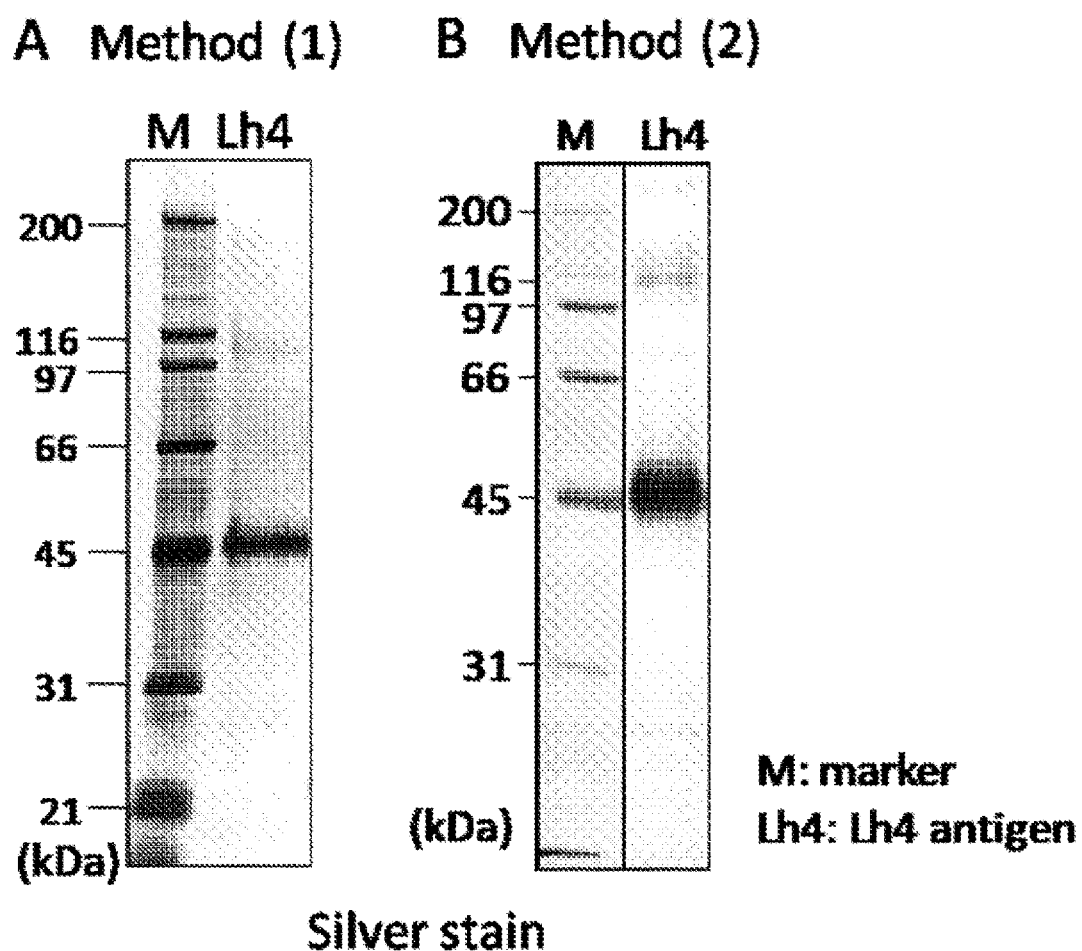
FIG. 29 shows the results of analysis of the Lh4 antigen produced in Example 16.

The Lh3 antigen (Lb and Lc proteins) expression strain produced in Example 15 was transformed using the genome-integrated Ld expression vector pRS-His4-LD2 prepared in Example 11(2); followed by screening according to a usual method, thereby obtaining yeast strain expressing Lb, Lc, and Ld proteins (Method 1). The Lh1 expression strain (Lc and Ld proteins) produced in Example 11(3) was transformed using the pGLD-His4-LB prepared in Example 4; followed by screening according to a usual method, thereby obtaining yeast strain expressing Lb, Lc, and Ld proteins (Method 2). Lh4 antigen was purified from the cells obtained by culturing the resulting two kinds of Lh4 antigen expression strains, in the same manner as in Example 2. After the purified Lh4 antigen was subjected to SDS-PAGE, silver staining was performed; as a result, as shown in FIG. 29, in all of the Lh4 antigens obtained by those expression strains, bands were observed at the positions near the monomer and dimer.

Example 17

Figure 30:
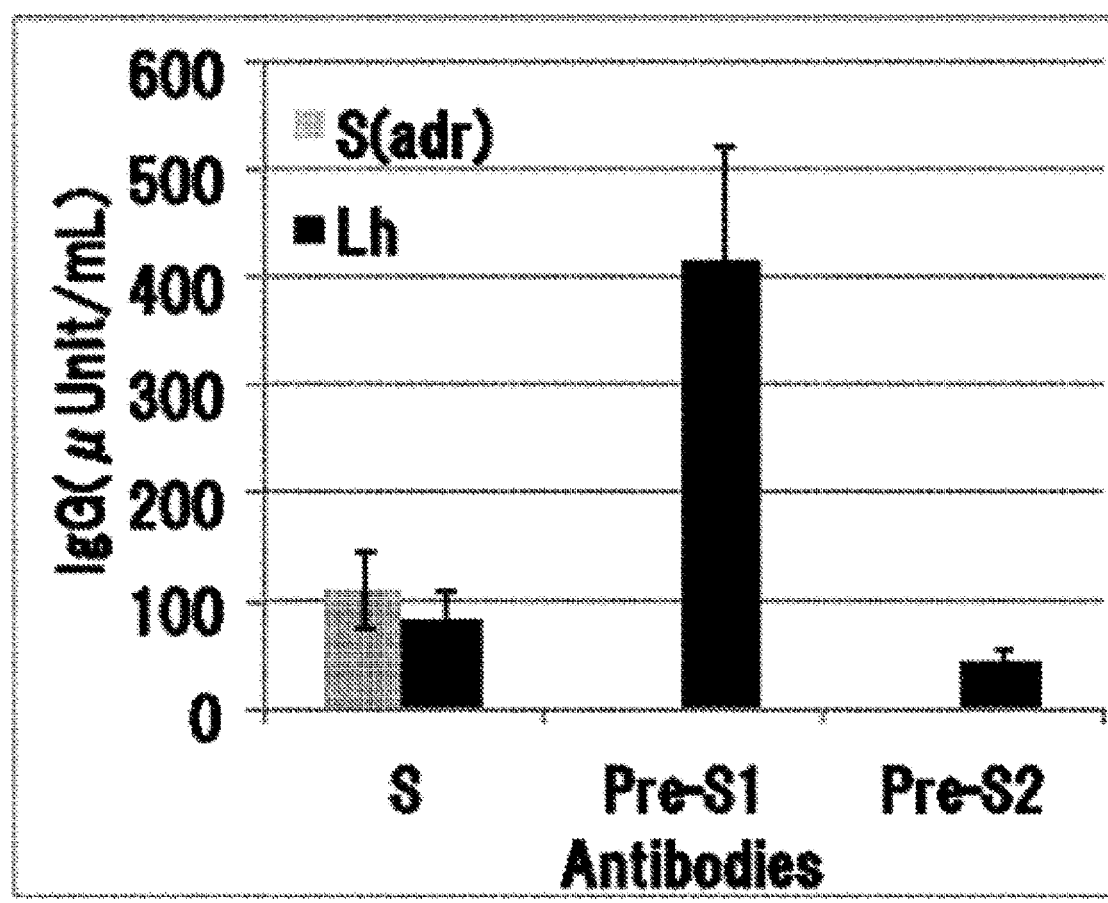
FIG. 30.

Production of Antibody Upon Administration of Lh1Antigen and Binding With Respect to La, Lb, Lc, and Ld Antigens Mice groups each consisting of four mice were immunized with Lh1antigen and S antigen particles (Fitzgerald)

produced in Example 12 in the same manner as in Example 9 to prepare antisera. The production amounts of the anti-Pre-S1 antibody, the anti-Pre-S2 antibody, and the anti-S antibody were measured in the same manner as in Example 7. FIG. 30 shows the results. Immunization with the S antigen as a control produced only anti-S antibody; in contrast, immunization with the Lh1antigen produced anti-S antibody, anti-Pre-S2 antibody, and anti-Pre-S1 antibody. In this case, the production amount of the anti-S antibody was almost equal to the production amount in the immunization with S antigen. The production amount of the anti-Pre-S2 antibody was slightly lower than that of the anti-S antibody. Moreover, the anti-Pre-S1 antibody was produced in an amount significantly greater than those of the other two antibodies. The production amount thereof was four times or more the amount of the anti-S antibody, and about 10 times the amount of the anti-Pre-S2 antibody.

Figure 31:
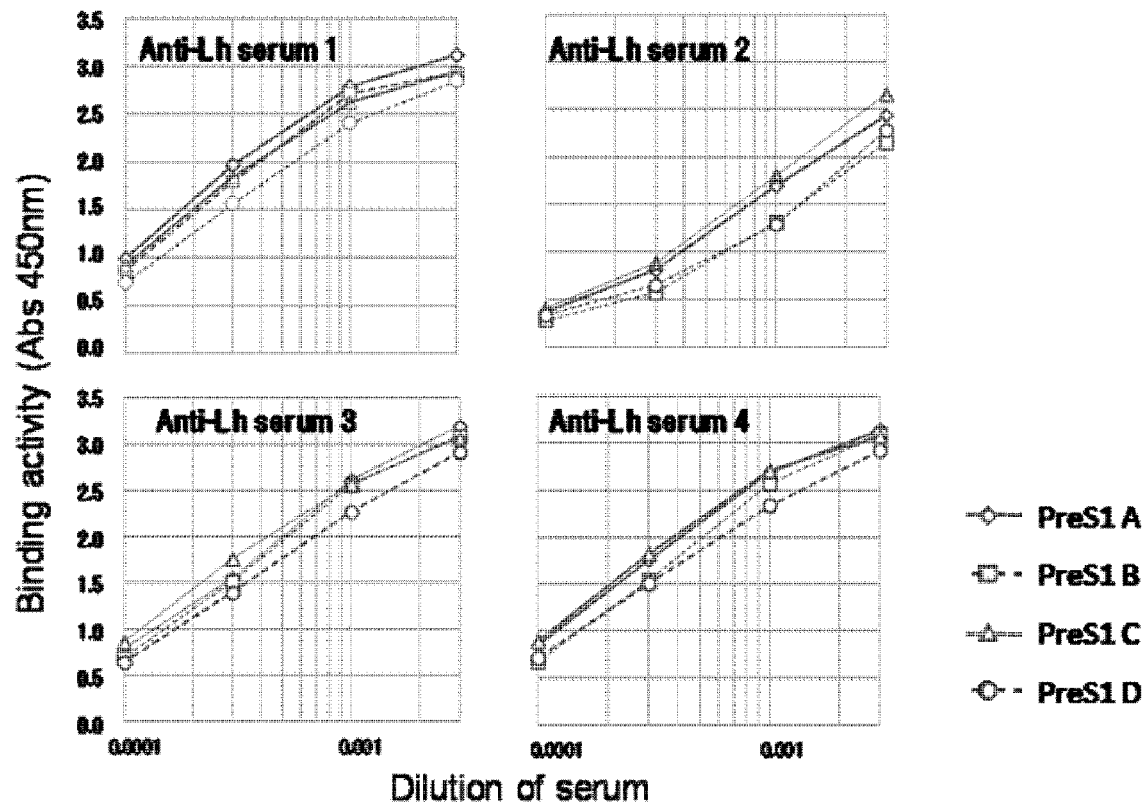
FIG. 31 shows the results of the test in Example 17. The vertical axis and the horizontal axis in the graph in FIG. 31 are the same as those in FIG. 14.

FIG. 31 shows the results obtained by examining the degree of binding of these antisera with respect to Pre-S1 of genotypes A, B, C, and D in the same manner as in Example 8. The antisera obtained by immunization with Lh1 antigen were bound to Pre-S1 of all genotypes with substantially the same strength. Although the effects of the antibody with respect to the Pre-S1 region for the prevention of HBV infection was described above, it is also concluded that Lh 1 antigen is an ideal antigen as a vaccine for inhibiting HBV infection because it produces a considerably large number of anti-Pre-S1 antibodies, and also enables binding to Pre-S1 of various genotypes.

Example 18

Time Course of Production of Antibody Upon Administration of Lh1 Antigen

Figure 32:
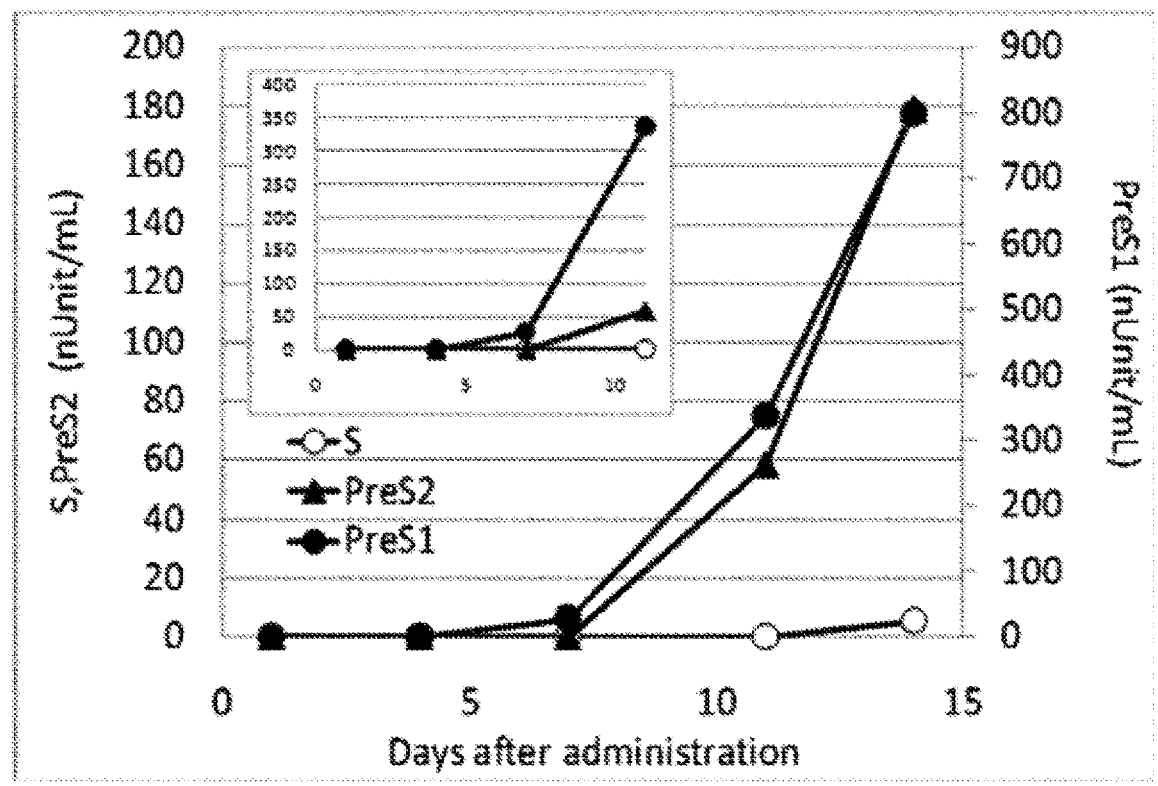
FIG. 32 shows the results of the test in Example 18. In each graph of FIG. 32, the vertical axis on the left denotes the production amounts of anti-S antibody and anti-Pre-S2 antibody, and the vertical axis on the right denotes the production amount of Pre-S1. The horizontal axis in the graph in FIG. 32 denotes the number of days after immunization with Lh1 antigen. The inserted figure shows three kinds of antibodies on the same vertical axis scale.

The mixture of 20 μg of Lh1antigen and alum adjuvant was subcutaneously administered to ICR mice once so as to immunize them. The time course of the production of the anti-Pre-S1 antibody, the anti-Pre-S2 antibody, and the anti-S antibody in the antisera obtained from the immunized mice was examined. The measurement for each antibody was performed in the same manner as in Example 7. FIG. 32 shows the results.

As can be seen from FIG. 32, the production amount of the anti-Pre-1 antibody was most rapidly increased; and the elevation of the anti-Pre-S1 antibody was confirmed on and after Day 7 of the immunization. The production of anti-Pre-S2 antibody was confirmed on and after Day 11 of the immunization. In contrast, the production of anti-S antibody was slow, and only slight production was observed on Day 14 of the immunization. On Day 14 of the immunization, the production amount of the anti-Pre-S1 antibody was about 4.4 times the amount of the anti-Pre-S2 antibody, and about 40 times the amount of the anti-S antibody.

The above results suggested that anti-Pre-S1 antibody is quickly produced in the body immunized with Lh1 antigen, and that the administration of Lh1 antigen is therefore expected to ensure rapid protective effects against infection by HBV.

Example 19

Detection of Escape Variant Antigen Using Anti-Lh1 Antibody

Figure 33:
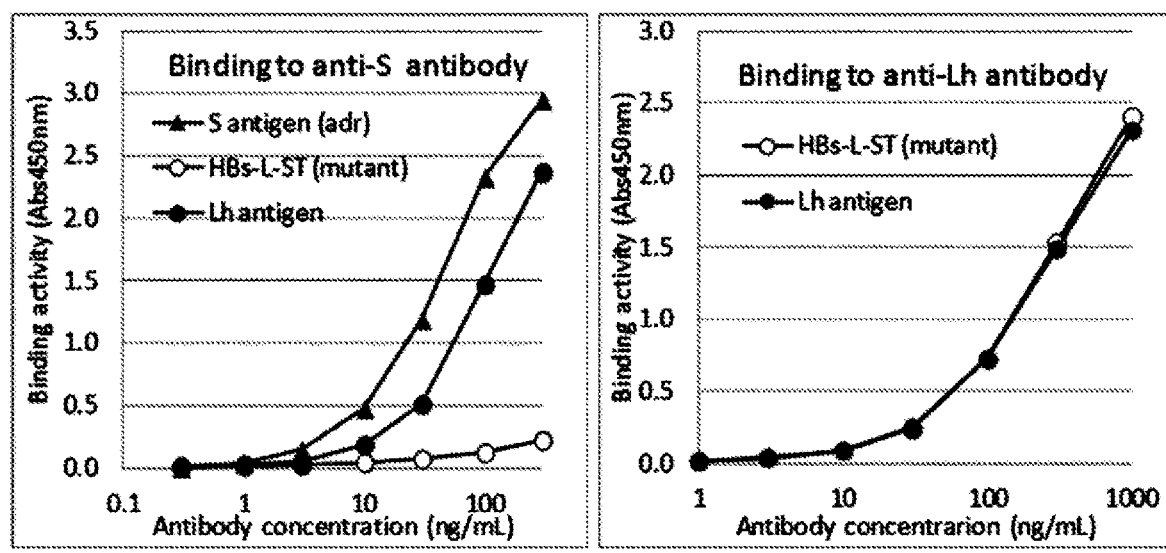
FIG. 33 shows the results of the test in Example 19. The left figure shows anti-S antibody, and the right figure shows the binding of anti-Lh1 antibody to various antigens.

The HBs-L-ST antigen (Beacle, Inc.: BCL-AGS-02), which is an escape variant obtained by introducing arginine into Position-129 and Position-145 of the S region of Lc antigen, was solid-phased; and the binding of the anti-S antibody used in Example 7 was observed. FIG. 33 shows the observation results. Although the HBs-L-ST antigen was hardly detected, the S antigen and the Lh1 antigen as the control were detected. More specifically, it was revealed that the HBs-L-ST antigen has properties of an escape variant that cannot be detected by a general anti-S antibody.

Subsequently, the HBs-L-ST antigen and the Lh antigen were solid-phased, and detection was performed using an anti-Lh1 antibody resulting from IgG purification of the antisera against the Lh1 antigen obtained in Example 17 using a protein A/G resin. As a result, all were detected at the same intensity. The above results revealed that the antibodies obtained by immunization with Lh1 antigen bind to an escape variant, as well; and that the antibodies are therefore expected to ensure infection preventing effects against escape variants, as well.

Example 20

Production of Antibody Using Lh1b, Lh2, Lh3, and Lh4

ICR mice were immunized with the Lh1b, Lh2, Lh3, and Lh4 antigens prepared in Examples 13 to 16 in the same manner as in Example 9, thereby obtaining antisera. The binding degrees of each of the obtained antisera with respect to Pre-S1 of genotypes A, B, C, and D were measured by the method shown in Example 8. While assuming that the binding degree with respect to Pre-S1 of genotype C is 100% for the Lh1b antisera, that the binding degree with respect to Pre-S1 of genotype A is 100% for the Lh2 antisera, that the binding degree with respect to Pre-S1 of genotype B is 100% for the Lh3 antisera, and that the binding degree with respect to Pre-S1 of genotype C is 100% for the Lh4 antisera, the relative values with respect to the binding degrees with respect to Pre-S1 of other genotypes were expressed. All values shown are average values of the measurement values of the antisera obtained from the three mice. Table 6 (binding of antisera obtained by immunization with various hybrid L antigens with respect to Pre-S1 of various genotypes) shows the results.

Since antisera prepared from Lh1b, Lh2, Lh3, and Lh4 antigens bind well to Pre-S1 of all genotypes, it was suggested that these hybrid L antigens are capable of producing antibodies that desirably bind to Pre-S1 of various genotypes; more specifically, it was suggested that they are capable of generating an immune reaction against several or more genotypes of HBV.

TABLE 6

| Antiserum against | Binding to Pre-S1 | | | |
|---|---|---|---|---|
| | genotype A | genotype B | genotype C | genotype D |
| Lh1b | 82 | 82 | 100 | 99 |
| Lh2 | 100 | 82 | 86 | 110 |
| Lh3 | 87 | 100 | 112 | 80 |
| Lh4 | 89 | 98 | 100 | 120 |

Example 21

HBV Infection Neutralization Activity of Antisera Obtained from Lh1 and Lh4 Antigens HBV infection neutralization activities of the antisera against the La, Lb, Lc, and Ld antigens prepared in Example 9, the antisera against Lh1 antigen prepared in Example 17, the antisera against Lh4 antigen prepared in Example 20, and sera (negative control) prepared from normal mice using HepG2-hNTCP-C4 cells (Non-patent Literature 2) were observed.

Each of the antisera described above was diluted 500-fold (the control sera were diluted 50-fold) with a predetermined culture medium, and HBV ($1.8 \times 10^4$ genome equivalent) of genotype A or C was added to the diluents to prepare samples. The samples were added to HepG2-hNTCP-C4 cells, and cultured for 16 hours; thereafter, the culture solution was removed and the cells were washed, and the culture was continued in normal medium for 12 days.

After the culture was completed, DNA was extracted from the cells, and HBV-DNA was quantified by RT-PCR. In RT-PCR, the primers of SEQ ID NOs: 63 and 64 were used, and the probe of SEQ ID NO: 65 was used. The measured amounts of HBV-DNA are shown as values relative to the amount of HBV-DNA obtained in the negative control sera. The results are shown in Table 7 (results of HBV infection neutralization test of antisera obtained by administration of various L antigens).

TABLE 7

| Antiserum | | Neutralizing Activity (% to control) | | | | | |
|---|---|---|---|---|---|---|---|
| | | Control | La | Lb | Lc | Ld | Lh1 | Lh4 |
| Infected HBV | A | 100.0 | 14.3 | 61.7 | 40.0 | 45.7 | 3.3 | 2.7 |
| | C | 100.0 | 34.3 | 73.3 | 10.7 | 75.7 | 2.7 | 4.3 |

In all antisera obtained by immunization with La, Lb, Lc, and Ld antigens, the HBV-DNA amount was reduced, and the activity to neutralize HBV infection was observed. The La antisera had the highest activity against HBV of genotype A. The Lb antisera was the weakest. On the other hand, the Lc antisera had the strongest activity against HBV of genotype C, and the Ld antisera was the weakest.

The antisera against the hybrid antigens, i.e., the Lh1 antigen (Lc and Ld proteins) and the Lh4 antigen (Lb, Lc, and Ld proteins), had strong neutralization activity against all genotypes of HBV. The above results revealed that immunization with a hybrid antigen produces an antibody that exhibits equally strong infection-preventing effects against HBV infection of several genotypes. The above results confirmed that hybrid antigens are useful as a vaccine against HBV of several genotypes.

Example 22

Production of Core Antigen

Figure 34:
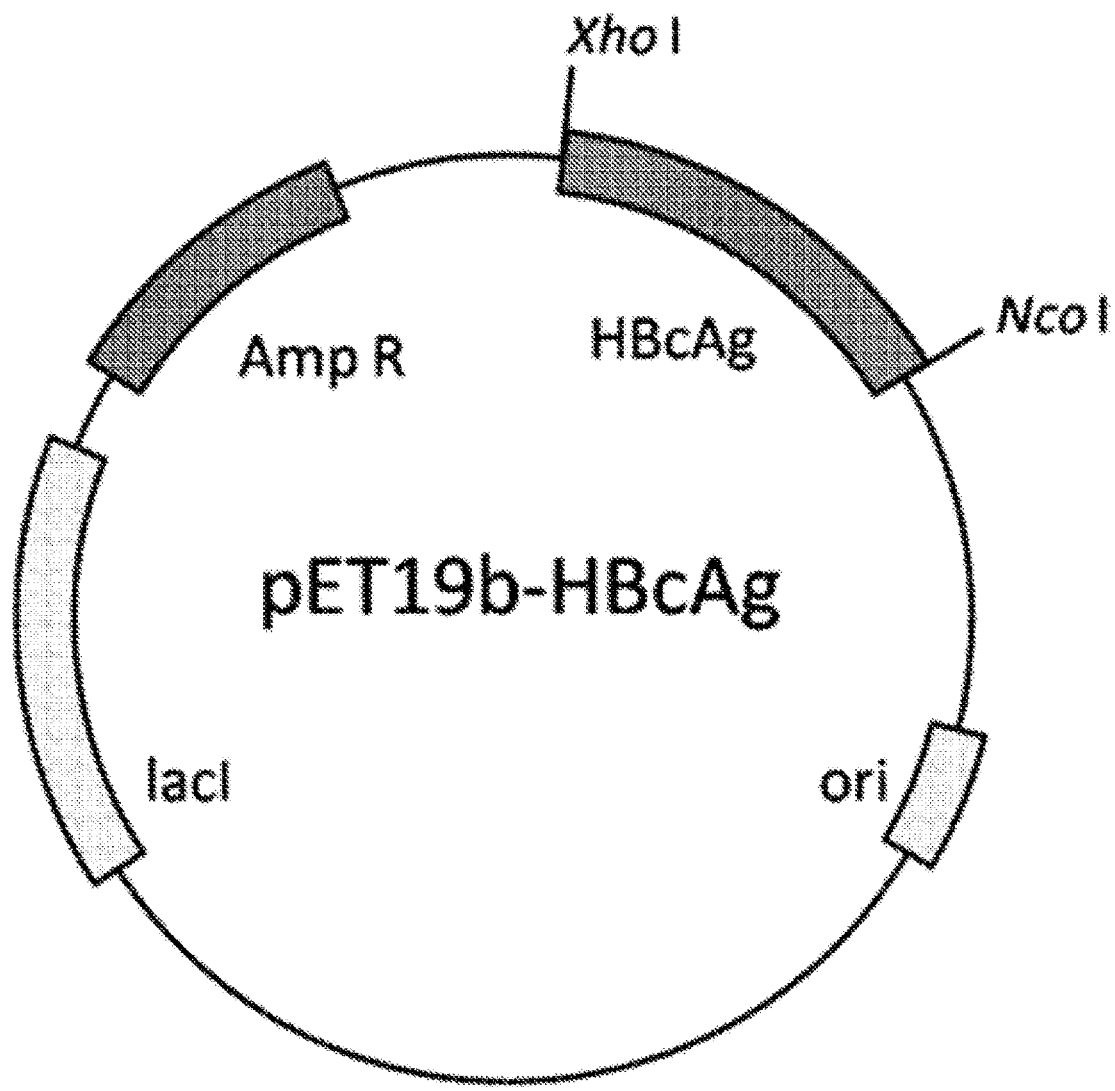
FIG. 34 shows pET19b-HBcAg constructed in Example 22.

The core antigen (C antigen) gene of hepatitis B virus was artificially synthesized based on the amino acid sequence of Accession No: LC090200 (SEQ ID NO: 66); and the synthesized gene was inserted into pET19b (Novagen), thereby producing the C antigen expression vector pET19b-HBcAg shown in FIG. 34. *Escherichia coli* strain BL21 (DE3) pLysS was transformed using this vector, thereby obtaining C antigen expression strain. C antigen was purified from the cells obtained by culturing the strain in the same manner as in Palenzuela (Palenzuela D O et al., Biotecnologia Aplicada, 2002, 19: 138-142) or other reports.

Figure 35:
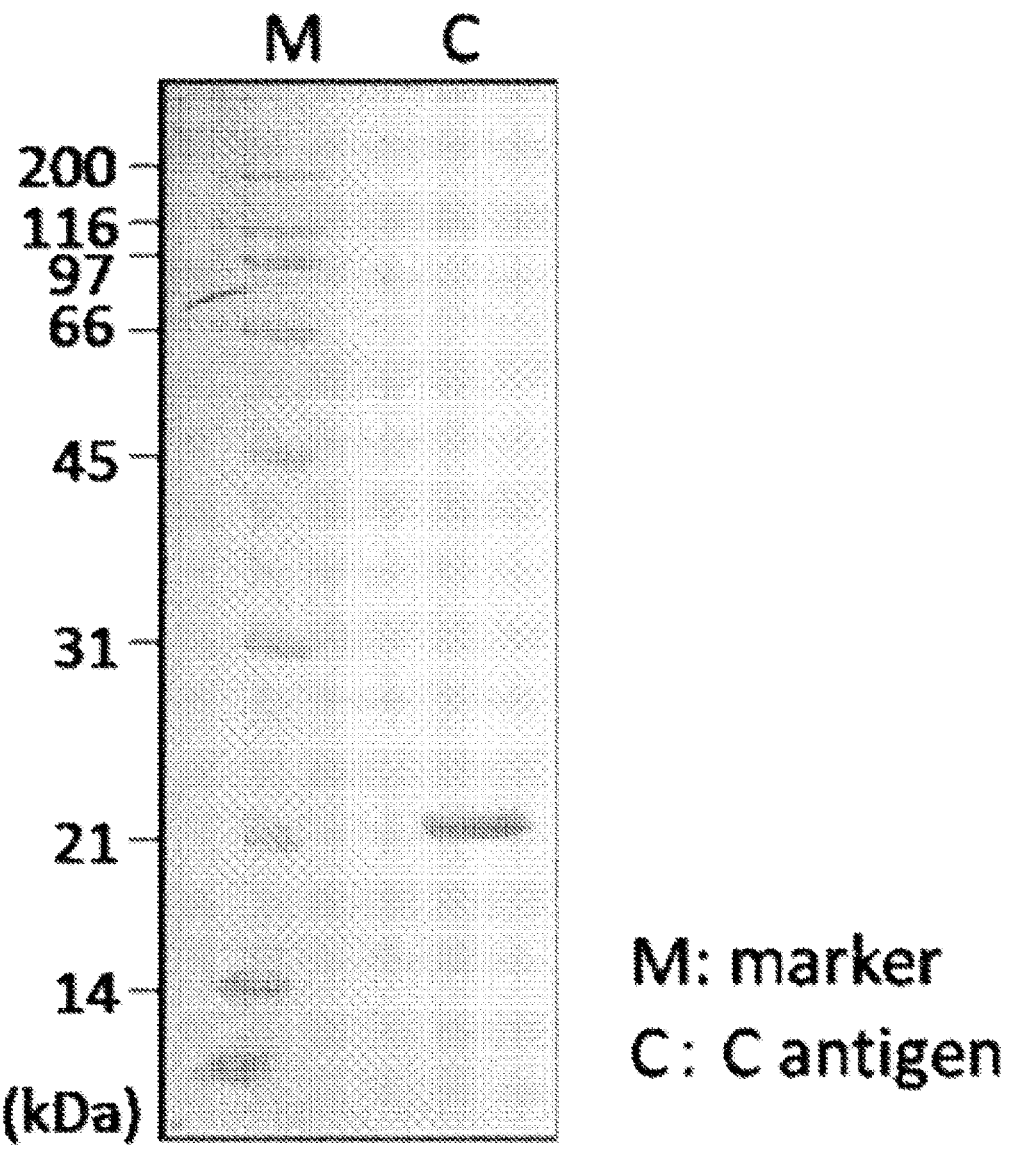
FIG. 35 shows the results of analysis of the C antigen produced in Example 22.

After the purified C antigen obtained above was subjected to electrophoresis, CBB staining was performed; as a result, as shown in FIG. 35, bands were observed at a position corresponding to a molecular weight of about 22 kDa, which is assumed to be a monomer position, and a position having a doubled molecular weight, which is assumed to be a dimer position. The particle size was measured by a dynamic light scattering method using a Zetasizer, and was found to be about 38.2 nm. It was thus found that the produced C antigen formed particles.

Example 23

Cell-Mediated Immunity Upon Administration of Lh Antigen and C Antigen

Figure 36:
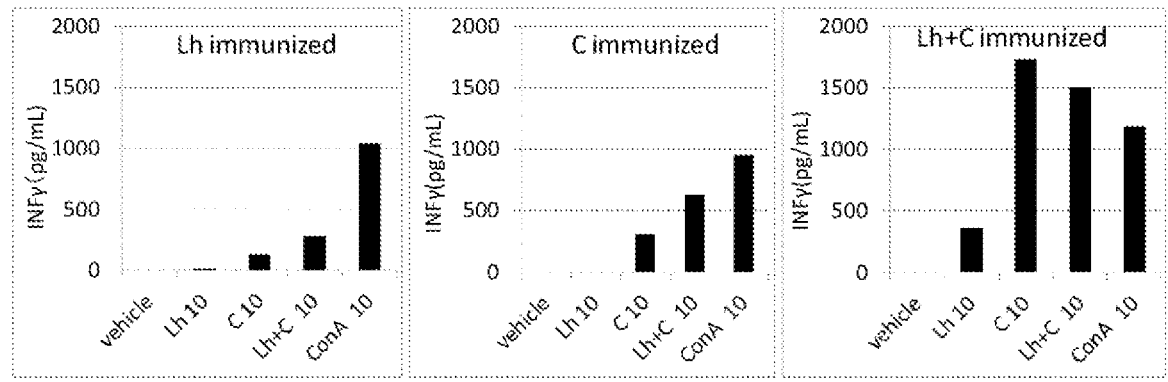
FIG. 36 shows the results of the test in Example 23.

Lh1 antigen prepared in Example 12 and the C antigen prepared in Example 22 in an amount of 5 µg each, or a mixture of these antigens in equal amounts (5 µg each) were formulated with Freund's adjuvant, and was immunized ICR mice by subcutaneous administration three times at 10-day intervals. One week after the final administration, the spleen cells were collected and cultured according to a usual method. On the next day of the collection, the cultured cells were stimulated by Lh1 antigen, C antigen, or a mixture thereof at a final concentration of 10 µg/mL. The amount of interferon-γ (INF-γ) in the culture supernatant was measured by ELISA (Murine INF-γ ELISA Kit, Diaclone) 4 days after the stimulation, thereby examining activation of cell-mediated immunity. Concanavalin A (10 µg/mL) stimulation was also performed as positive control stimulation so as to confirm the capability of spleen cells to release INF-γ. FIG. 36 shows the results.

In spleen cells obtained from mice immunized with Lh1 antigen or C antigen, the release of IFN-γ was not observed after the cells were stimulated with Lh1 antigen; however, when the cells were stimulated with C antigen or a mixture of Lh1 antigen and C antigen, the release of INF-γ was observed. These increase of INF-γ released was greater in the case of immunization with the C antigen than in the case of immunization with the Lh1 antigen, thereby confirming the facilitation effect by C antigen. In spleen cells obtained from mice immunized with mixture of Lh1 antigen and C antigen, the amount of IFN-γ released was significantly greater than that in the immunization with the Lh1 antigen or C antigen alone, indicating that a synergistic effects in the activation of cell-mediated immunity was observed when the immunization was performed with these two kinds of antigens. In the spleen cells obtained from the mice subjected to the mixed immunization, the release of INF-γ was observed even when the stimulation was performed with only Lh1 antigen. These results revealed that although the cell-mediated immunity-activating capacity by the immunization with Lh1 antigen alone is low, the cell-mediated immunity was activated by the immunization with C antigen alone, and was synergistically activated by the coexistence of C antigen with Lh1 antigen.

Example 24

Activation of Cell-Mediated Immunity when Immunization was Performed with Mixture of Lh1 Antigen and C Antigen, or S Antigen and C Antigen Mice were immunized with a mixture (5 µg each) of Lh1 antigen and C antigen, or a mixture of S antigen and C antigen, in the same manner as in Example 23; and the spleen cells were collected and cultured. On the next day of the collection, the cultured cells were stimulated with various antigens (final concentration: 10 µg/ml). Table 8 shows the results of measurement of the amount of INF-γ released (activation of cell-mediated immunity upon the immunization with a mixture of Lh1 antigen and C antigen, or S antigen and C antigen). The values in Table 8 denote the INF-γ release amounts (pg/ml).

TABLE 8

| | Stimulated antigen | | | | | | | |
|---|---|---|---|---|---|---|---|---|
| | none | C | La + C | Lb + C | Lc + C | Ld + C | Lh1 + C | S + C |
| Immunized antigen Lh1 + C | 67 | 956 | 2343 | 2722 | 2509 | 2157 | 3002 | 1125 |
| S + C | 62 | 311 | 955 | 418 | 502 | 398 | 811 | 592 |

Among the stimulation with all kinds of antigens, the spleen cells obtained from the mice immunized with Lh1 antigen and C antigen had an INF-γ release amount higher than that of the spleen cells obtained from the mice immunized with S antigen and C antigen, regardless of the genotype of the antigen used for the stimulation. The above results revealed that regardless of the genotype, when the immunization is performed with a mixture of L1 antigen and C antigen, the cell-mediated immunity is more intensively stimulated than in the case of immunization with a mixture of S antigen and C antigen; and that as the stimulating antigen, L antigen is stronger than S antigen, and Lh1 antigen is the strongest among the L antigens.

The invention claimed is:

1. A virus-like particle comprising two or more HBs-L antigen proteins having a genotype selected from the group consisting of genotypes A, B, C, and D, for use in the generation of humoral immunity or cell-mediated immunity against two or more genotypes of HBV, the HBs-L antigen protein contained in the virus-like particle comprising:

[1]
(a) genotype A HBs-L antigen protein; and
(b) genotype B HBs-L antigen protein, [2]
(a) genotype A HBs-L antigen protein; and
(b) genotype D HBs-L antigen protein, [3]
(a) genotype B HBs-L antigen protein; and
(b) genotype C HBs-L antigen protein, [4]
(a) genotype B HBs-L antigen protein; and
(b) genotype D HBs-L antigen protein, [5]
(a) genotype C HBs-L antigen protein; and
(b) genotype D HBs-L antigen protein, or
[6]
(a) genotype B HBs-L antigen protein,
(b) genotype C HBs-L antigen protein; and
(c) genotype D HBs-L antigen protein,
wherein
the genotype A HBs-L antigen protein has an amino acid sequence represented by any one of SEQ ID NOs: 1 to 9, or an amino acid sequence translated from a base sequence in which 8% or less mutation with respect to a base sequence encoding an amino acid sequence represented by any one of SEQ ID NOs: 1 to 9 is introduced;
the genotype B HBs-L antigen protein has an amino acid sequence represented by any one of SEQ ID NOs: 10 to 18, or an amino acid sequence translated from a base sequence in which 8% or less mutation with respect to a base sequence encoding an amino acid sequence represented by any one of SEQ ID NOs: 10 to 18 is introduced;
the genotype C HBs-L antigen protein has an amino acid sequence represented by any one of SEQ ID NOs: 19 to 28, or an amino acid sequence translated from a base sequence in which 8% or less mutation with respect to a base sequence encoding an amino acid sequence represented by any one of SEQ ID NOs: 19 to 28 is introduced; and
the genotype D HBs-L antigen protein has an amino acid sequence represented by any one of SEQ ID NOs: 29 to 38, or an amino acid sequence translated from a base sequence in which 8% or less mutation with respect to a base sequence encoding an amino acid sequence represented by any one of SEQ ID NOs: 29 to 38 is introduced.

2. A virus-like particle composition comprising:
a first virus-like particle which is the virus-like particle according to claim 1, and
a second virus-like particle having a single kind of HBs-L antigen protein having a genotype of A, B, C, or D, wherein, in the second virus-like particle,
the genotype A HBs-L antigen protein has an amino acid sequence represented by any one of SEQ ID NOs: 1 to 9, or an amino acid sequence translated from a base sequence in which 8% or less mutation with respect to a base sequence encoding an amino acid sequence represented by any one of SEQ ID NOs: 1 to 9 is introduced;
the genotype B HBs-L antigen protein has an amino acid sequence represented by any one of SEQ ID NOs: 10 to 18, or an amino acid sequence translated from a base sequence in which 8% or less mutation with respect to a base sequence encoding an amino acid sequence represented by any one of SEQ ID NOs: 10 to 18 is introduced;
the genotype C HBs-L antigen protein has an amino acid sequence represented by any one of SEQ ID NOs: 19 to 28, or an amino acid sequence translated from a base sequence in which 8% or less mutation with respect to a base sequence encoding an amino acid sequence represented by any one of SEQ ID NOs: 19 to 28 is introduced; and
the genotype D HBs-L antigen protein has an amino acid sequence represented by any one of SEQ ID NOs: 29 to 38, or an amino acid sequence translated from a base sequence in which 8% or less mutation with respect to a base sequence encoding an amino acid sequence represented by any one of SEQ ID NOs: 29 to 38 is introduced,
the virus-like particle composition being used in the generation of humoral immunity or a cell-mediated immune reaction against two or more genotypes of HBV.

3. A virus-like particle composition for use in the generation of humoral immunity or cell-mediated immunity against two or more genotypes of HBV,
the virus-like particle composition comprising two or more combinations of virus- like particles comprising a single kind of HBs-L antigen protein;
the combination being
[1] a combination of
(a) a virus-like particle comprising genotype A HBs-L antigen protein; and
(b) a virus-like particle comprising genotype B HBs-L antigen protein,
[2] a combination of
(a) a virus-like particle comprising genotype A HBs-L antigen protein; and
(b) a virus-like particle comprising genotype D HBs-L antigen protein,
[3] a combination of
(a) a virus-like particle comprising genotype B HBs-L antigen protein; and
(b) a virus-like particle comprising genotype C HBs-L antigen protein,
[4] a combination of
(a) a virus-like particle comprising genotype B HBs-L antigen protein; and
(b) a virus-like particle comprising genotype D HBs-L antigen protein,
[5] a combination of
(a) a virus-like particle comprising genotype C HBs-L antigen protein; and
(b) a virus-like particle comprising genotype D HBs-L antigen protein, or
[6] a combination of
(a) a virus-like particle comprising genotype B HBs-L antigen protein,
(b) a virus-like particle comprising genotype C HBs-L antigen protein; and
(c) a virus-like particle comprising genotype D HBs-L antigen protein,
wherein
the genotype A HBs-L antigen protein has an amino acid sequence represented by any one of SEQ ID NOs: 1 to 9, or an amino acid sequence translated from a base sequence in which 8% or less mutation with respect to a base sequence encoding an amino acid sequence represented by any one of SEQ ID NOs: 1 to 9 is introduced;

the genotype B HBs-L antigen protein has an amino acid sequence represented by any one of SEQ ID NOs: 10 to 18, or an amino acid sequence translated from a base sequence in which 8% or less mutation with respect to a base sequence encoding an amino acid sequence represented by any one of SEQ ID NOs: 10 to 18 is introduced;

the genotype C HBs-L antigen protein has an amino acid sequence represented by any one of SEQ ID NOs: 19 to 28, or an amino acid sequence translated from a base sequence in which 8% or less mutation with respect to a base sequence encoding an amino acid sequence represented by any one of SEQ ID NOs: 19 to 28 is introduced; and the genotype D HBs-L antigen protein has an amino acid sequence represented by any one of SEQ ID NOs: 29 to 38, or an amino acid sequence translated from a base sequence in which 8% or less mutation with respect to a base sequence encoding an amino acid sequence represented by any one of SEQ ID NOs: 29 to 38 is introduced.

4. A virus-like particle composition comprising:
a first virus-like particle which is the virus-like particle according to claim 1, and
a second virus-like particle containing a HBV core antigen,
the virus-like particle composition including the virus-like particle containing the HBV core antigen being used for the generation of humoral immunity or a cell-mediated immune reaction against two or more genotypes of HBV.

5. A vaccine for treating and/or inhibiting hepatitis B comprising the virus-like particle according to claim 1.

6. A virus-like particle composition comprising:
the virus-like particle composition according to claim 2, and
a virus-like particle containing a HBV core antigen,
the virus-like particle composition including the virus-like particle containing the HBV core antigen being used for the generation of humoral immunity or a cell-mediated immune reaction against two or more genotypes of HBV.

7. A virus-like particle composition comprising:
the virus-like particle composition according to claim 3, and
a virus-like particle containing a HBV core antigen,
the virus-like particle composition including the virus-like particle containing the HBV core antigen being used for the generation of humoral immunity or a cell-mediated immune reaction against two or more genotypes of HBV.

8. A vaccine for treating and/or inhibiting hepatitis B comprising the virus-like particle composition according to claim 2.

9. A vaccine for treating and/or inhibiting hepatitis B comprising the virus-like particle composition according to claim 3.

10. A vaccine for treating and/or inhibiting hepatitis B comprising the virus-like particle composition according to claim 4.

11. A vaccine for treating and/or inhibiting hepatitis B comprising the virus-like particle composition according to claim 6.

12. A vaccine for treating and/or inhibiting hepatitis B comprising the virus-like particle composition according to claim 7.

* * * * *